US012721727B2

(12) United States Patent
Guidotti et al.

(10) Patent No.: US 12,721,727 B2
(45) **Date of Patent: *Sep. 1, 2026**

(54) CARDIAC LEAFLET COAPTERS

(71) Applicant: MTEX CARDIO AG, Pfaffikon (CH)

(72) Inventors: Andrea Guidotti, Zollikon (CH); Karl Heinz Kuck, Hamburg (DE); Michael Butscheid, Wilen bei Wollerau (CH); David Zarbatany, Laguna Niguel, CA (US); Ricardo Roman, Chula Vista, CA (US); Idan Tobis, Beit Hashmonai (IL); Monica Tocchi, Zurich (CH); Yaniv Marmur, Yokneam Moshava (IL)

(73) Assignee: MTEX CARDIO AG, Pfaffikon (CH)

( * ) Notice: Subject to any disclaimer, the term of this patent is extended or adjusted under 35 U.S.C. 154(b) by 721 days.

This patent is subject to a terminal disclaimer.

(21) Appl. No.: 17/422,900

(22) PCT Filed: Jan. 14, 2020

(86) PCT No.: PCT/IL2020/050057

§ 371 (c)(1),
(2) Date: Jul. 14, 2021

(87) PCT Pub. No.: WO2020/148755

PCT Pub. Date: Jul. 23, 2020

(65) Prior Publication Data

US 2022/0096236 A1 Mar. 31, 2022

Related U.S. Application Data

(60) Provisional application No. 62/792,092, filed on Jan. 14, 2019.

(51) Int. Cl.
*A61F 2/24* (2006.01)
*A61B 17/00* (2006.01)

(52) U.S. Cl.
CPC .......... *A61F 2/2463* (2013.01); *A61F 2/2418* (2013.01); *A61F 2/2454* (2013.01);
(Continued)

(58) Field of Classification Search
CPC ............ A61F 2/2463; A61F 2220/0008; A61F 2/2454; A61F 2/246
See application file for complete search history.

(56) References Cited

U.S. PATENT DOCUMENTS

| | | | |
|---|---|---|---|
| 5,607,445 | A | 3/1997 | Summers |
| 5,810,882 | A | 9/1998 | Bolduc et al. |

(Continued)

FOREIGN PATENT DOCUMENTS

| | | | |
|---|---|---|---|
| CN | 104055600 | A | 9/2014 |
| CN | 106572910 | A | 4/2017 |

(Continued)

OTHER PUBLICATIONS

International Search Report and Written Opinion dated Feb. 5, 2015, issued in International Application No. PCT/IB2014/002155.

(Continued)

*Primary Examiner* — David H Willse
(74) *Attorney, Agent, or Firm* — Sughrue Mion, PLLC

(57) ABSTRACT

A coaptation-assist device is provided for treating a native atrioventricular valve. The coaptation-assist device includes a ventricular anchor and a neo-leaflet. The ventricular anchor includes a subannular anchor and a ventricular wall anchor. The subannular anchor is configured to be anchored in position in a subannular space of a target native leaflet of the native atrioventricular valve. The ventricular wall anchor includes one or more anchor-loop wire loops, which are configured to be anchored in position against a ventricular wall outside the subannular space. The neo-leaflet is supported by the ventricular anchor and is configured to at least (Continued)

partially replace function of the target native leaflet by providing a surface of coaptation for one or more opposing native leaflets that oppose the target native leaflet, when the ventricular anchor is positioned in the ventricle. Other embodiments are also described.

37 Claims, 43 Drawing Sheets

(52) U.S. Cl.
CPC .. *A61F 2/2466* (2013.01); *A61B 2017/00783* (2013.01); *A61F 2220/0008* (2013.01); *A61F 2230/0008* (2013.01); *A61F 2230/0056* (2013.01)

(56) References Cited

U.S. PATENT DOCUMENTS 6,419,695 B1 7/2002 Gabbay
6,478,776 B1 11/2002 Rosenman et al.
6,629,534 B1 10/2003 St. Goar et al.
6,663,633 B1 12/2003 Pierson, III
6,752,813 B2 6/2004 Goldfarb et al.
6,869,444 B2 3/2005 Gabbay
6,986,775 B2 1/2006 Morales et al.
7,070,618 B2 7/2006 Streeter
7,160,322 B2 1/2007 Gabbay
7,374,572 B2 5/2008 Gabbay
7,527,646 B2 5/2009 Rahdert et al.
7,544,198 B2 6/2009 Parodi
7,635,329 B2 12/2009 Goldfarb et al.
7,988,725 B2 8/2011 Gross et al.
8,216,303 B2 7/2012 Navia
8,449,599 B2 5/2013 Chau et al.
8,870,936 B2 10/2014 Rowe
8,870,950 B2 10/2014 Hacohen
8,876,894 B2 11/2014 Tuval et al.
9,232,999 B2 1/2016 Maurer et al.
9,445,893 B2 9/2016 Vaturi
9,592,121 B1 3/2017 Khairkhahan
10,166,098 B2 1/2019 Khairkhahan et al.
10,226,341 B2 3/2019 Gross et al.
10,751,180 B2 8/2020 Schewel
2001/0021872 A1 9/2001 Bailey et al.
2003/0120340 A1 6/2003 Liska et al.
2003/0199975 A1 10/2003 Gabbay
2005/0004668 A1 1/2005 Aklog et al.
2005/0010287 A1 1/2005 Macoviak et al.
2005/0038509 A1 2/2005 Ashe
2005/0107871 A1 5/2005 Realyvasquez et al.
2005/0159810 A1 7/2005 Filsoufi
2005/0235511 A1 10/2005 Tkachyk
2006/0195183 A1 8/2006 Navia et al.
2006/0235511 A1 10/2006 Osborne
2006/0293698 A1 12/2006 Douk
2007/0185571 A1 8/2007 Kapadia et al.
2009/0048668 A1 2/2009 Wilson et al.
2009/0132036 A1 5/2009 Navia
2009/0138079 A1 5/2009 Tuval et al.
2010/0036479 A1 2/2010 Hill et al.
2010/0298929 A1 11/2010 Thornton et al.
2011/0166644 A1 7/2011 Keeble et al.
2011/0319990 A1 12/2011 Macoviak et al.
2012/0150290 A1 6/2012 Gabbay
2012/0179247 A1 7/2012 Navia
2012/0197388 A1 8/2012 Khairkhahan et al.
2012/0245678 A1 9/2012 Solem
2013/0023985 A1 1/2013 Khairkhahan et al.
2013/0103140 A1 4/2013 Subramanian et al.
2013/0261737 A1 10/2013 Costello
2014/0025163 A1 1/2014 Padala et al.
2014/0031928 A1* 1/2014 Murphy ................ A61F 2/2418
623/2.37
2014/0067048 A1 3/2014 Chau et al.
2014/0067054 A1* 3/2014 Chau ..................... A61F 2/2466
623/2.36
2014/0121763 A1 5/2014 Duffy et al.
2014/0207231 A1 7/2014 Hacohen et al.
2014/0257467 A1 9/2014 Lane et al.
2014/0316516 A1 10/2014 Vidlund et al.
2014/0350662 A1 11/2014 Vaturi
2014/0358223 A1 12/2014 Rafiee et al.
2015/0119981 A1 4/2015 Khairkhahan et al.
2015/0119982 A1 4/2015 Quill et al.
2015/0127097 A1* 5/2015 Neumann ............... A61F 2/246
623/2.17
2015/0142103 A1 5/2015 Vidlund
2015/0265404 A1 9/2015 Rankin
2016/0074164 A1 3/2016 Naor
2016/0166382 A1* 6/2016 Nguyen .................. A61F 2/246
623/2.17
2016/0184098 A1 6/2016 Vaturi
2016/0324639 A1* 11/2016 Nguyen ................ A61F 2/2409
2017/0065418 A1 3/2017 Skarsgard
2017/0112618 A1 4/2017 Li et al.
2017/0128203 A1 5/2017 Zhang et al.
2017/0209265 A1 7/2017 Karapetian et al.
2018/0289473 A1 10/2018 Rajagopal et al.
2019/0029826 A1 1/2019 Zeitani
2019/0060072 A1 2/2019 Zeng
2019/0201191 A1 7/2019 Mclean et al.
2019/0201192 A1 7/2019 Kruse et al.
2019/0254817 A1 8/2019 Centola et al.
2019/0282364 A1 9/2019 Khairkhahan et al.
2019/0290431 A1 9/2019 Genovese et al.
2019/0290432 A1 9/2019 Duffy et al.
2019/0298332 A1 10/2019 Khairkhahan et al.
2019/0350705 A1 11/2019 Schewel et al.
2020/0188109 A1 6/2020 Fatemi Far et al.
2020/0205969 A1 7/2020 Hacohen
2020/0222185 A1 7/2020 Kappetein et al.
2020/0275974 A1 9/2020 Gifford, III et al.
2020/0289265 A1 9/2020 Gifford, III et al.
2021/0085462 A1* 3/2021 Gifford, III ........... A61F 2/2445
2021/0196462 A1 7/2021 Khairkhahan

FOREIGN PATENT DOCUMENTS

EP 3 620 133 A1 3/2020
WO 2005/112827 A2 12/2005
WO 2006/097931 A2 9/2006
WO 2007/131513 A1 11/2007
WO 2008/035337 A2 3/2008
WO 2009/116041 A2 9/2009
WO 2012/102928 A1 8/2012
WO 2013/021375 A2 2/2013
WO 2013/150512 A1 10/2013
WO 2013/192107 A1 12/2013
WO 2014/114796 A1 7/2014
WO 2014/144937 A2 9/2014
WO 2014/188412 A2 11/2014
WO 2014/189974 A1 11/2014
WO 2014/207575 A2 12/2014
WO 2015/017689 A1 2/2015
WO 2015/057407 A1 4/2015
WO 2015/061533 A1 4/2015
WO 2015/195823 A1 12/2015
WO 2015/200497 A1 12/2015
WO 2016/098104 A2 6/2016
WO 2017/079279 A1 5/2017
WO 2017/115123 A1 7/2017
WO 2017/156133 A1 9/2017
WO 2018/142217 A2 8/2018
WO 2018/169878 A1 9/2018
WO 2019/045910 A1 3/2019
WO 2020/055433 A1 3/2020
WO 2020/101676 A1 5/2020
WO 2020/186106 A1 9/2020
WO 2020/236757 A1 11/2020
WO 2021/055983 A1 3/2021

(56) References Cited

FOREIGN PATENT DOCUMENTS

OTHER PUBLICATIONS

International Search Report and Written Opinion dated Apr. 22, 2020, issued in International Application No. PCT/IL2020/050057.
International Search Report and Written Opinion dated Apr. 20, 2021, issued in International Application No. PCT/IB2020/056926.
International Search Report and Written Opinion dated Dec. 2, 2020, issued in International Application No. PCT/IB2020/057429.
International Search Report and Written Opinion dated Apr. 28, 2022, issued in International Application No. PCT/IB2022/050669.
Office Action dated Jan. 21, 2021 for U.S. Appl. No. 16/529,247.
Office Action dated Aug. 25, 2021 for U.S. Appl. No. 16/529,247.
Office Action dated Feb. 13, 2017 for U.S. Appl. No. 14/901,468.
Office Action dated Jun. 1, 2017 for U.S. Appl. No. 14/901,468.
Office Action dated Mar. 8, 2018 for U.S. Appl. No. 14/901,468.
Examiner Interview Summary dated Aug. 16, 2018 for U.S. Appl. No. 14/901,468.
Office Action dated Sep. 26, 2018 for U.S. Appl. No. 14/901,468.
Examiner Interview Summary dated Oct. 30, 2018 for U.S. Appl. No. 14/901,468.
Office Action dated Mar. 7, 2019 for U.S. Appl. No. 14/901,468.
Examiner Interview Summary dated Jul. 15, 2019 for U.S. Appl. No. 14/901,468.
Office Action dated Nov. 5, 2019 for U.S. Appl. No. 14/901,468.
Examiner Interview Summary dated Mar. 25, 2020 for U.S. Appl. No. 14/901,468.
Notice of Allowance dated May 13, 2020 for U.S. Appl. No. 14/901,468.
Office Action dated Jan. 20, 2023 for U.S. Appl. No. 16/921,687.
Translation of Office Action dated Jun. 28, 2024 for Chinese Application No. 202080021065.8.

* cited by examiner

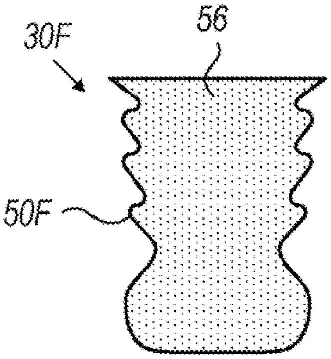
FIG. 3F
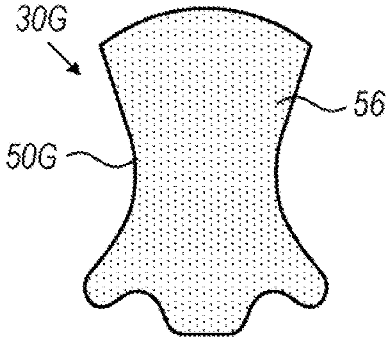
FIG. 3G
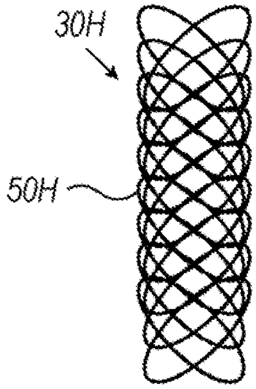
FIG. 3H
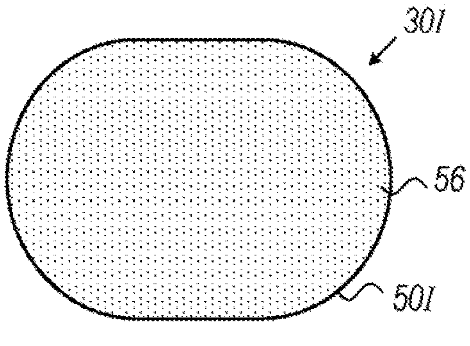
FIG. 3I
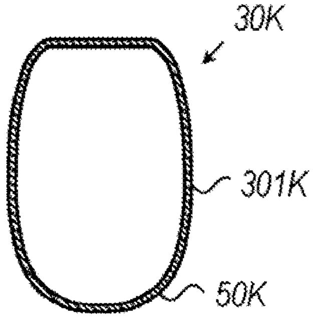
FIG. 3K
FIG. 3J
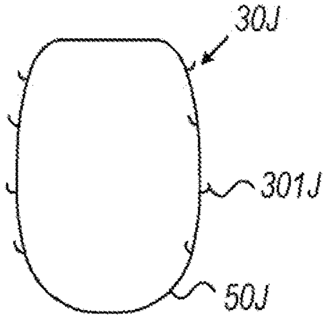

FIG. 10D
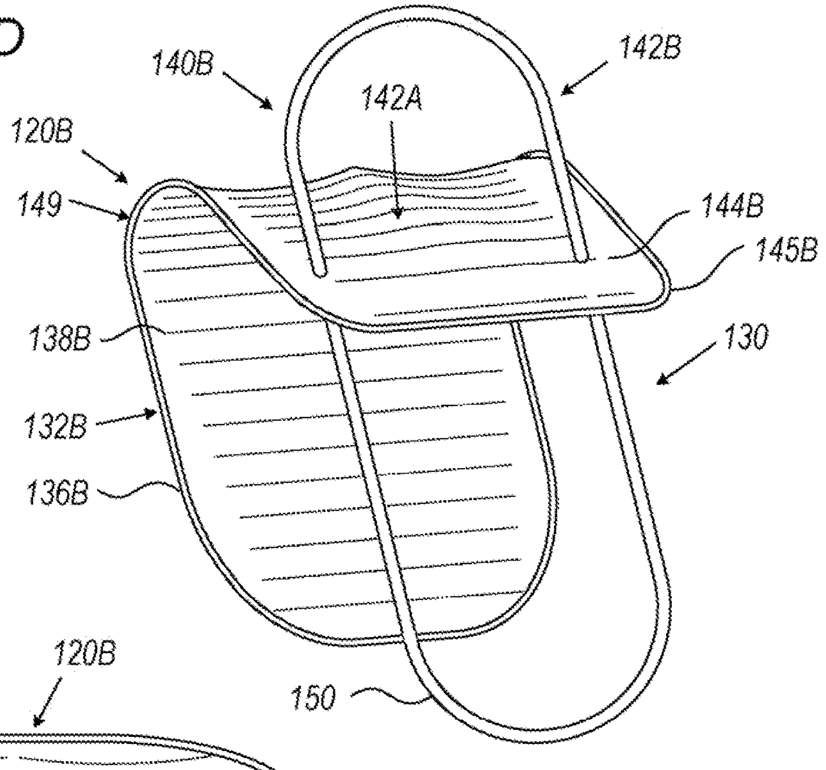
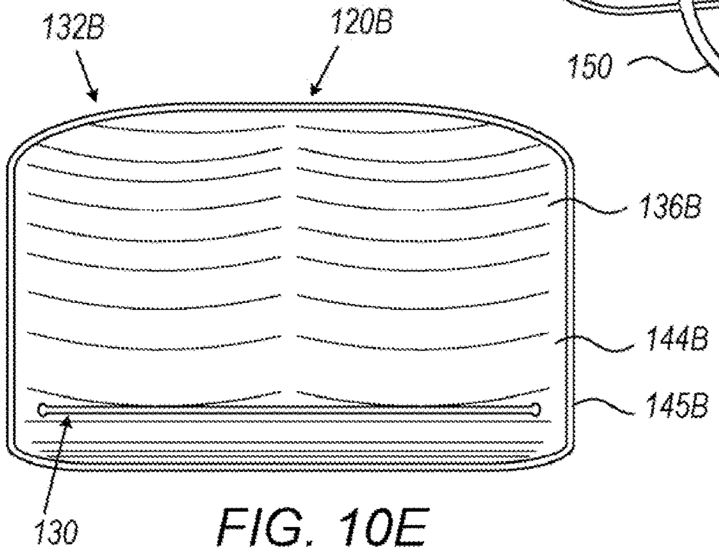
FIG. 10E
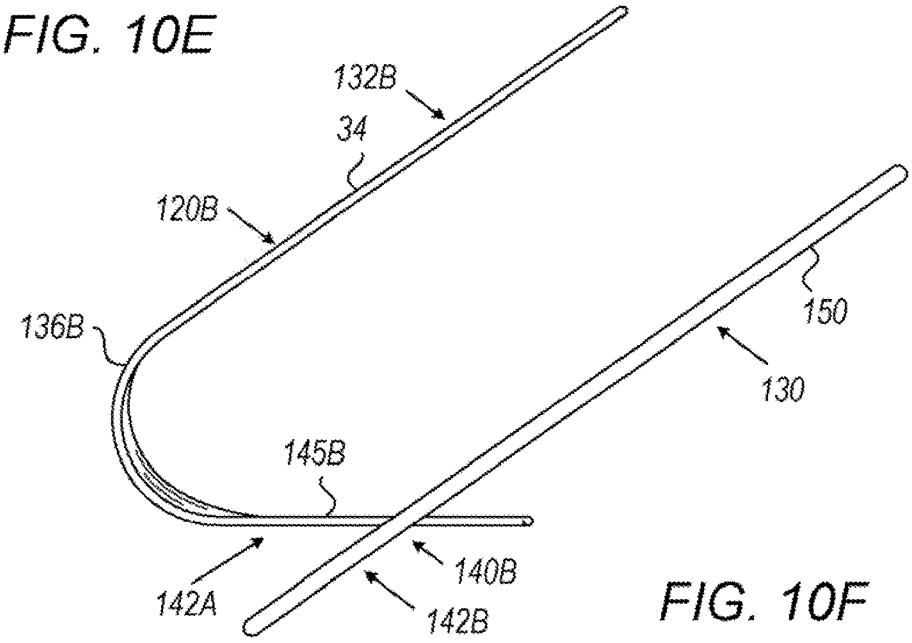
FIG. 10F

FIG. 13B
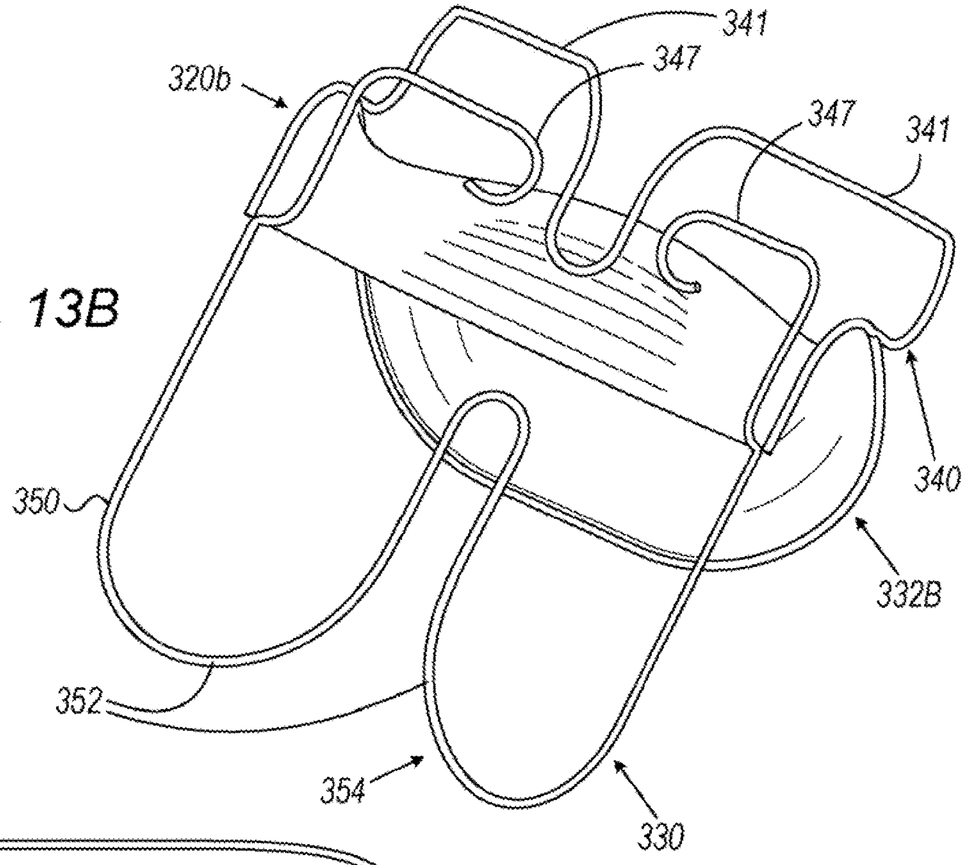
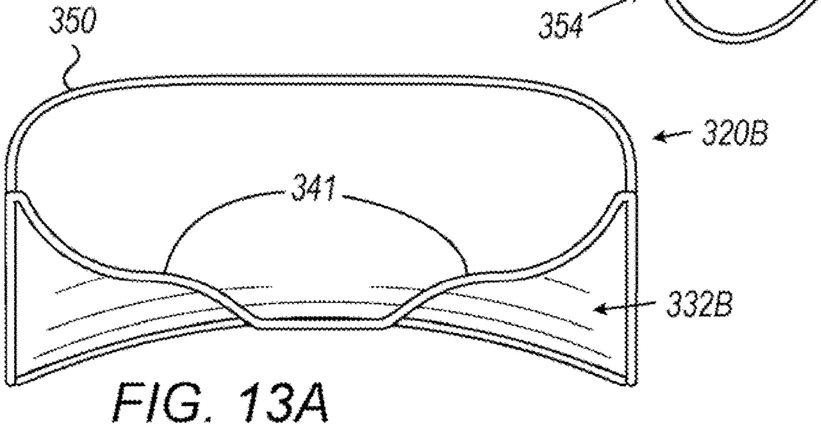
FIG. 13A

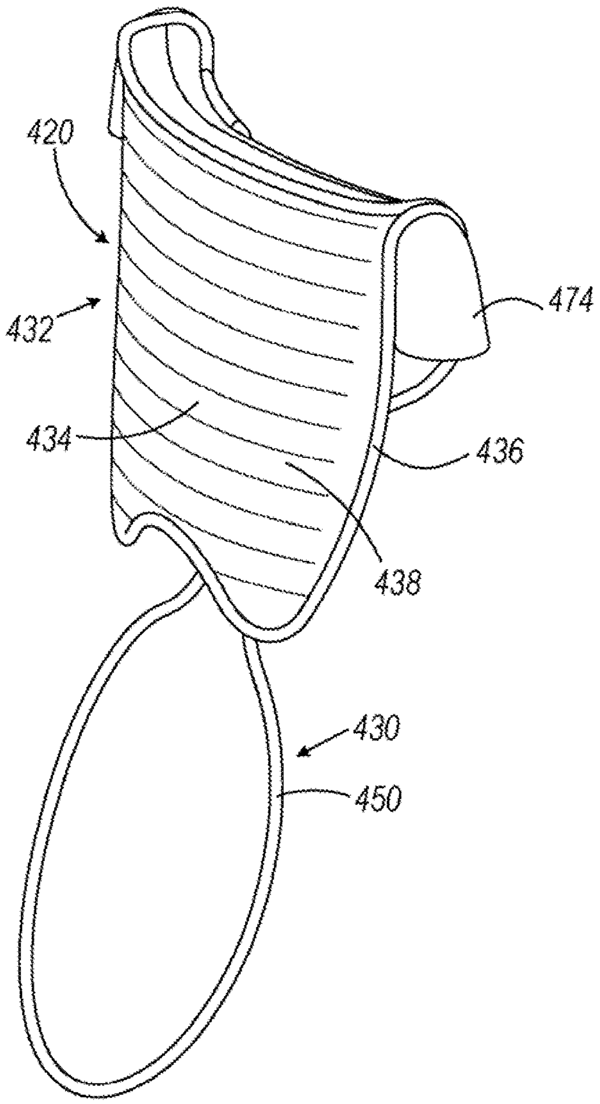
FIG. 16A
FIG. 16B
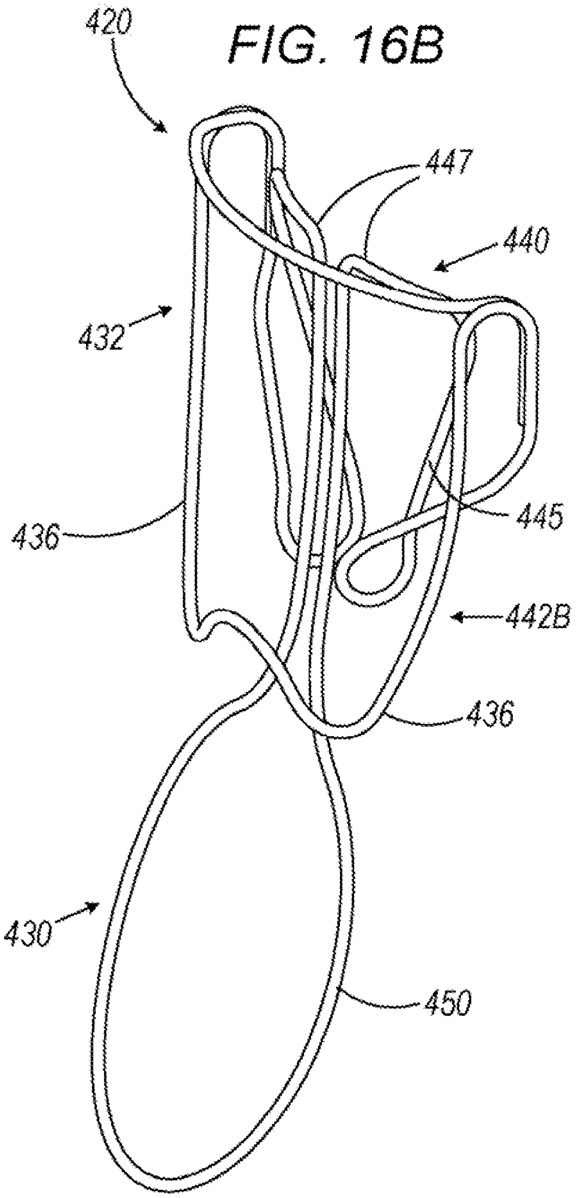

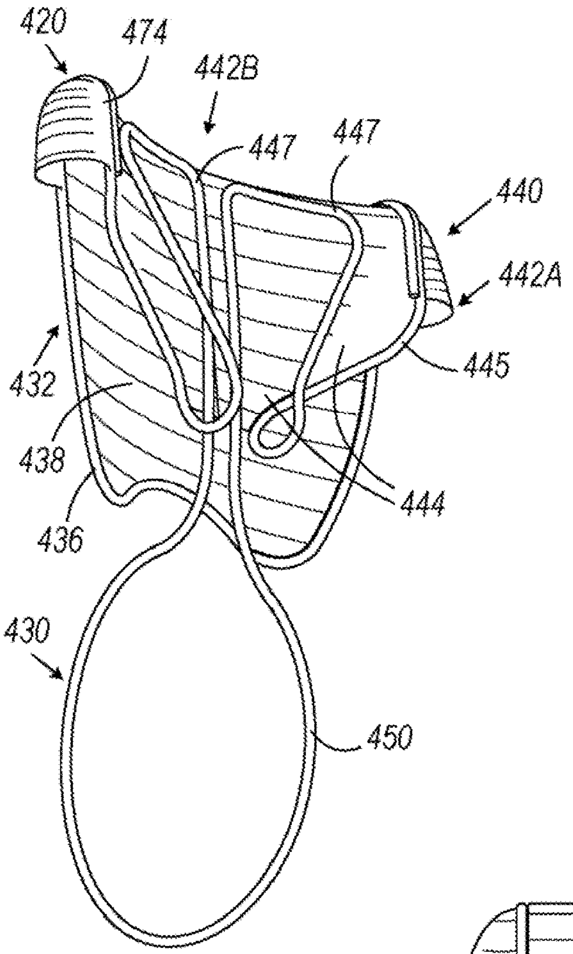
FIG. 16C
FIG. 16D
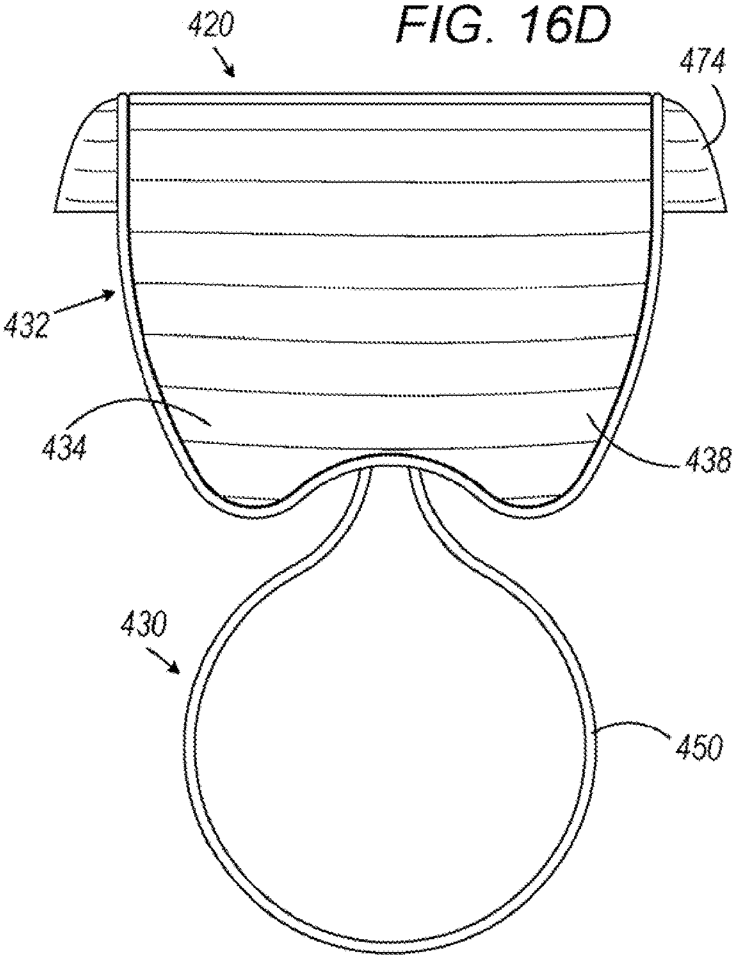

FIG. 20B
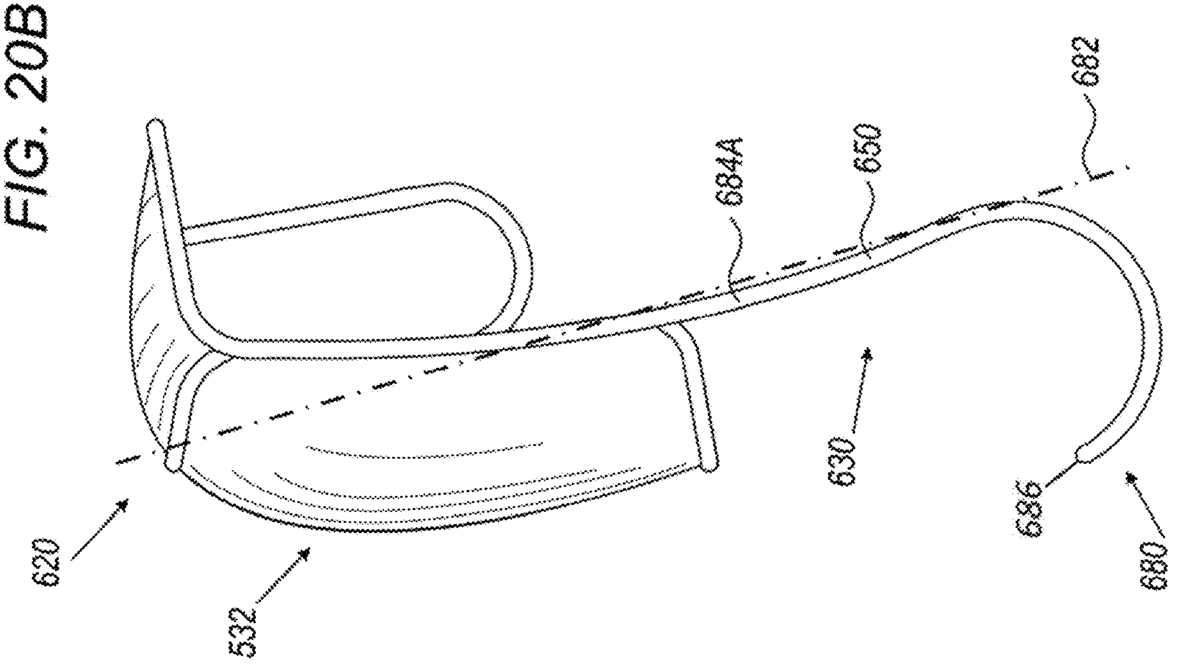
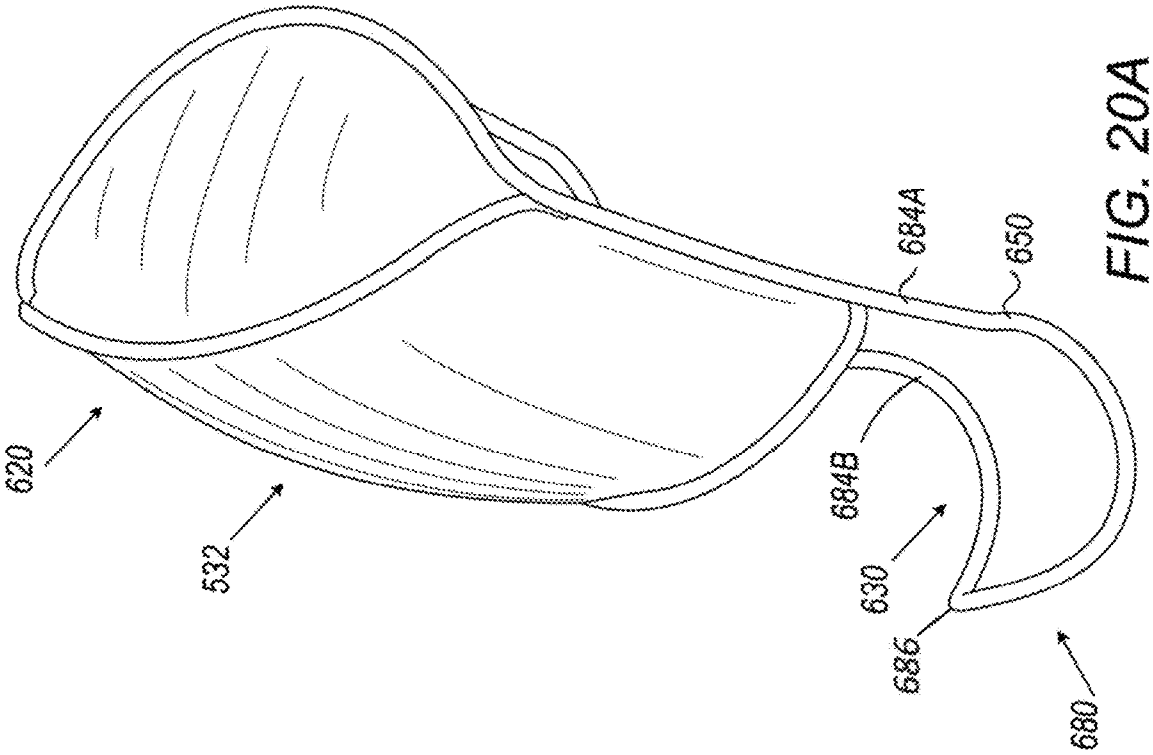
FIG. 20A

CARDIAC LEAFLET COAPTERS

CROSS-REFERENCE TO RELATED APPLICATIONS

The present patent application is the U.S. national stage of International Application PCT/IL2020/050057, filed Jan. 14, 2020, which claims priority from U.S. Provisional Application 62/792,092, filed Jan. 14, 2019, which is assigned to the assignee of the present application and is incorporated herein by reference.

FIELD OF THE INVENTION

The present invention relates generally to medical devices and methods. More particularly, this invention relates to prosthetic devices and methods for improving the function of regurgitating heart valves and other circulatory valves.

BACKGROUND OF THE INVENTION

Valvular regurgitation (VR) is a disease in which the heart's native valve does not close properly, causing blood to flow backward into the atrium when the ventricle contracts, reducing its efficiency. Severe regurgitation affects more than 5 million patients in the U.S. today and is estimated to affect 8% of the world population.

SUMMARY OF THE INVENTION

Embodiments of the present invention provide coaptation-assist devices for treating a native valve of a subject. Typically, the native valve suffers from a valvular pathology, such as functional mitral or tricuspid regurgitation, often characterized by lack of mobility of the leaflets in the valve. The native valve is typically an atrioventricular valve, i.e., the tricuspid or the mitral valve.

Each of the coaptation-assist devices comprises a loop-shaped ventricular anchor, which is configured to be positioned in a ventricle, extending between a ventricular apical area of a target native leaflet of the native atrioventricular valve, and to remain anchored in position against surrounding anatomy, including a ventricular wall and the ventricular apical area. In some applications, each of the loop-shaped ventricular anchors comprises an anchor-loop wire loop, which defines at least a portion of a border of the loop-shaped ventricular anchor, and, optionally, an anchor-loop cover attached to the anchor-loop wire loop.

Each of the coaptation-assist devices further comprises a neo-leaflet, which is supported by the loop-shaped ventricular anchor and is configured to at least partially replace function of the target native leaflet by providing a surface of coaptation for one or more opposing native leaflets that oppose the target native leaflet, when the loop-shaped ventricular anchor is positioned in the ventricle.

There is therefore provided, in accordance with an Inventive Concept 1 of the present invention, a coaptation-assist device for treating a native atrioventricular valve of a subject, the coaptation-assist device comprising:

- a loop-shaped ventricular anchor, which comprises an anchor-loop wire loop, which (i) defines at least a portion of a border of the loop-shaped ventricular anchor, and (ii) is configured (a) to be positioned in a ventricle, extending between a ventricular apical area and a subannular surface of a target native leaflet of the native atrioventricular valve, and (b) to remain anchored in position against surrounding anatomy, including the subannular surface, a ventricular wall, and the ventricular apical area; and
- a neo-leaflet, which is supported by the loop-shaped ventricular anchor and is configured to at least partially replace function of the target native leaflet by providing a surface of coaptation for one or more opposing native leaflets that oppose the target native leaflet, when the anchor-loop wire loop is positioned in the ventricle.

Inventive Concept 2. The coaptation-assist device according to Inventive Concept 1, wherein the loop-shaped ventricular anchor is configured to remain anchored in position by force applied by the anchor-loop wire loop to the surrounding anatomy.

Inventive Concept 3. The coaptation-assist device according to Inventive Concept 2, wherein the loop-shaped ventricular anchor is configured to remain anchored in position by radially-outwardly-directed force applied by the anchor-loop wire loop to the surrounding anatomy.

Inventive Concept 4. The coaptation-assist device according to Inventive Concept 1, wherein the loop-shaped ventricular anchor is configured to remain anchored in position by friction between the anchor-loop wire loop and the surrounding anatomy.

Inventive Concept 5. The coaptation-assist device according to Inventive Concept 1, wherein the loop-shaped ventricular anchor is configured to be atraumatic so as not to penetrate tissue of the surrounding anatomy.

Inventive Concept 6. The coaptation-assist device according to Inventive Concept 1, wherein the coaptation-assist device does not comprise any elements that are configured to penetrate tissue.

Inventive Concept 7. The coaptation-assist device according to Inventive Concept 1, wherein the anchor-loop wire loop is shaped as a closed loop that defines an entirety of the border of the loop-shaped ventricular anchor.

Inventive Concept 8. The coaptation-assist device according to Inventive Concept 1, wherein the anchor-loop wire loop comprises metal.

Inventive Concept 9. The coaptation-assist device according to Inventive Concept 1, wherein the anchor-loop wire loop, when unconstrained, is curved along at least 50% of a length of the anchor-loop wire loop, the length measured around the anchor-loop wire loop.

Inventive Concept 10. The coaptation-assist device according to Inventive Concept 9, wherein the anchor-loop wire loop, when unconstrained, is curved along at least 75% of the length of the anchor-loop wire loop.

Inventive Concept 11. The coaptation-assist device according to Inventive Concept 1, wherein the anchor-loop wire loop is shaped as at least 75% of an oval when unconstrained.

Inventive Concept 12. The coaptation-assist device according to Inventive Concept 1, wherein the loop-shaped ventricular anchor further comprises at least one supporting wire, which is coupled to the anchor-loop wire loop at two sites on the anchor-loop wire loop.

Inventive Concept 13. The coaptation-assist device according to Inventive Concept 1, wherein the anchor-loop wire loop is configured to remain anchored in position against the subannular surface, the ventricular wall, and one or more ventricular papillary muscles of the ventricular apical area, when the anchor-loop wire loop is positioned in the ventricle.

Inventive Concept 14. The coaptation-assist device according to Inventive Concept 1, wherein the anchor-loop wire loop is shaped so as to define two or more lobes.

Inventive Concept 15. The coaptation-assist device according to Inventive Concept 14, wherein the anchor-loop wire loop is shaped so as to define exactly two lobes.

Inventive Concept 16. The coaptation-assist device according to Inventive Concept 1, wherein the neo-leaflet is configured such that the coaptation surface is generally static throughout a cardiac cycle of the subject upon implantation of the coaptation-assist device in a heart of the subject.

Inventive Concept 17. The coaptation-assist device according to Inventive Concept 1, wherein the neo-leaflet is configured such that the coaptation surface moves toward and away from the one or more opposing native leaflets during a cardiac cycle of the subject upon implantation of the coaptation-assist device in a heart of the subject.

Inventive Concept 18. The coaptation-assist device according to Inventive Concept 1, wherein the neo-leaflet extends directly from the loop-shaped ventricular anchor.

Inventive Concept 19. The coaptation-assist device according to Inventive Concept 1, wherein the coaptation surface has an area of between 2 and 20 cm2.

Inventive Concept 20. The coaptation-assist device according to Inventive Concept 1, wherein the anchor-loop wire loop, when unconstrained, includes a distal-most portion that is curved away from a best-fit plane defined by lateral portions of the anchor-loop wire loop.

Inventive Concept 21. The coaptation-assist device according to Inventive Concept 1, wherein the anchor-loop wire loop includes a distal-most portion that is configured to curve away from the ventricular wall when the anchor-loop wire loop is positioned in ventricle.

Inventive Concept 22. The coaptation-assist device according to any one of Inventive Concepts 1-21, further comprising a native-leaflet grasper, which is configured to grasp atrial and ventricular surfaces of the target native leaflet, in order to support the neo-leaflet, and to orient the neo-leaflet with respect to the native atrioventricular valve.

Inventive Concept 23. The coaptation-assist device according to Inventive Concept 22, wherein the neo-leaflet is coupled to the loop-shaped ventricular anchor via the native-leaflet grasper.

Inventive Concept 24. The coaptation-assist device according to Inventive Concept 23, comprising a wire loop that is shaped so as to at least partially define the neo-leaflet and the native-leaflet grasper.

Inventive Concept 25. The coaptation-assist device according to Inventive Concept 22, wherein the native-leaflet grasper is shaped so as to define first and second portions that are configured to grasp the atrial and the ventricular surfaces of the target native leaflet by sandwiching at least a portion of the atrial and the ventricular surfaces of the target native leaflet between the first and the second portions of the native-leaflet grasper.

Inventive Concept 26. The coaptation-assist device according to Inventive Concept 25, wherein the first and the second portions are configured to fold toward each other so as to grasp the atrial and the ventricular surfaces of the target native leaflet by sandwiching the at least a portion of the atrial and the ventricular surfaces of the target native leaflet between the first and the second portions of the native-leaflet grasper.

Inventive Concept 27. The coaptation-assist device according to Inventive Concept 26, wherein the native-leaflet grasper is shaped so as to further define a third portion at a fold between the first and the second portions of the native-leaflet grasper, and wherein the third portion of the native-leaflet grasper is configured to extend around the free edge of the target native leaflet when the first and the second portions of the native-leaflet grasper sandwich the at least a portion of the atrial and the ventricular surfaces of the target native leaflet.

Inventive Concept 28. The coaptation-assist device according to Inventive Concept 25, wherein the coaptation-assist device is configured such that:

the first portion of the native-leaflet grasper is pivotably coupled to the loop-shaped ventricular anchor, the first portion of the native-leaflet grasper is pivotably coupled to the second portion of the native-leaflet grasper, and the second portion of the native-leaflet grasper is pivotably coupled to the neo-leaflet.

Inventive Concept 29. The coaptation-assist device according to Inventive Concept 22, wherein the native-leaflet grasper comprises one or more sub-native-leaflet supports, which are configured to press against one or more portions of the ventricular surface of the target native leaflet when the anchor-loop wire loop is positioned in the ventricle.

Inventive Concept 30. The coaptation-assist device according to Inventive Concept 29, wherein the native-leaflet grasper further comprises one or more supra-annular supports, which are configured to press against an atrial surface of the target native leaflet, such that the one or more sub-native-leaflet supports and the one or more supra-annular supports sandwich and grasp the target native leaflet when the anchor-loop wire loop is positioned in the ventricle.

Inventive Concept 31. The coaptation-assist device according to Inventive Concept 22, wherein the native-leaflet grasper comprises one or more supra-annular supports, which are configured to press against an atrial surface of the target native leaflet when the anchor-loop wire loop is positioned in the ventricle.

Inventive Concept 32. The coaptation-assist device according to any one of Inventive Concepts 1-21, wherein the ventricular wall is a ventricular septal wall, and wherein the anchor-loop wire loop is configured to be remain anchored in position against the surrounding anatomy, including the subannular surface, the ventricular septal wall, and the ventricular apical area.

Inventive Concept 33. The coaptation-assist device according to any one of Inventive Concepts 1-21, wherein the native atrioventricular valve is a tricuspid valve, and wherein the neo-leaflet is configured to at least partially replace function of the target native leaflet by providing a surface of coaptation for the one or more opposing native leaflets of the tricuspid valve, when the anchor-loop wire loop is positioned in the ventricle.

Inventive Concept 34. The coaptation-assist device according to Inventive Concept 33, wherein the target native leaflet is a native septal leaflet of the tricuspid valve, wherein the ventricular wall is a ventricular septal wall, and wherein the neo-leaflet is configured to at least partially replace function of the septal leaflet by providing a surface of coaptation for one or more of the opposing native posterior and anterior leaflets of the tricuspid valve, when the anchor-loop wire loop is positioned in the ventricle and remains anchored in position against the surrounding anatomy, including the subannular surface, the ventricular septal wall, and the ventricular apical area.

Inventive Concept 35. The coaptation-assist device according to any one of Inventive Concepts 1-21, wherein the native atrioventricular valve is a mitral valve, and wherein the neo-leaflet is configured to at least partially replace function of the target native leaflet by providing a surface of coaptation for the opposing native leaflet of the mitral valve, when the anchor-loop wire loop is positioned in the ventricle.

Inventive Concept 36. The coaptation-assist device according to Inventive Concept 35, wherein the target native leaflet is a native anterior leaflet of the mitral valve, wherein the ventricular wall is a ventricular septal wall, and wherein the neo-leaflet is configured to at least partially replace function of the native anterior leaflet by providing a surface of coaptation for an opposing native posterior leaflet of the mitral valve, when the anchor-loop wire loop is positioned in the ventricle and remains anchored in position against the surrounding anatomy, including the subannular surface, the ventricular septal wall, and the ventricular apical area.

Inventive Concept 37. The coaptation-assist device according to any one of Inventive Concepts 1-21, wherein the coaptation-assist device is configured such that the coaptation surface of the neo-leaflet crosses from an atrial side to a ventricular side of a native valvular plane, when the anchor-loop wire loop is positioned in the ventricle.

Inventive Concept 38. The coaptation-assist device according to any one of Inventive Concepts 1-21, wherein the loop-shaped ventricular anchor further comprises an anchor-loop cover attached to the anchor-loop wire loop.

Inventive Concept 39. The coaptation-assist device according to Inventive Concept 38, wherein the anchor-loop cover comprises one or more thin sheets of material that extend across a space at least partially surrounded by the anchor-loop wire loop.

Inventive Concept 40. The coaptation-assist device according to Inventive Concept 38, wherein the anchor-loop cover comprises braided wires.

Inventive Concept 41. The coaptation-assist device according to Inventive Concept 38, wherein the anchor-loop cover comprises a coating on the anchor-loop wire loop.

Inventive Concept 42. The coaptation-assist device according to any one of Inventive Concepts 1-21, comprising a coaptation-assist-device wire loop that is shaped so as to at least partially define the neo-leaflet and the anchor-loop wire loop.

Inventive Concept 43. The coaptation-assist device according to Inventive Concept 42, wherein the coaptation-assist-device wire loop is shaped so as to further at least partially define a native-leaflet grasper, which is configured to grasp atrial and ventricular surfaces of the target native leaflet, in order to support the neo-leaflet, and to orient the neo-leaflet with respect to the native atrioventricular valve.

Inventive Concept 44. The coaptation-assist device according to Inventive Concept 43, wherein the coaptation-assist-device wire loop is shaped so as to at least partially define the native-leaflet grasper along the coaptation-assist-device wire loop between the neo-leaflet and the loop-shaped ventricular anchor.

Inventive Concept 45. The coaptation-assist device according to any one of Inventive Concepts 1-21, wherein the neo-leaflet comprises a neo-leaflet wire loop that defines at least a portion of a border of the neo-leaflet, and a neo-leaflet cover, which is attached to the neo-leaflet wire loop and provides the surface of coaptation.

Inventive Concept 46. The coaptation-assist device according to Inventive Concept 45, wherein the coaptation-assist device is configured such that when unconstrained, an angle is defined between (a) an anchor-loop best-fit plane defined by the anchor-loop wire loop and (b) a neo-leaflet best-fit plane defined by the neo-leaflet wire loop, the angle between 60 and 100 degrees.

Inventive Concept 47. The coaptation-assist device according to Inventive Concept 46, wherein the angle is between 80 and 90 degrees.

Inventive Concept 48. The coaptation-assist device according to Inventive Concept 45, wherein the coaptation-assist device is configured such that when unconstrained, an angle is defined between (a) an anchor-loop best-fit plane defined by the anchor-loop wire loop and (b) a neo-leaflet best-fit plane defined by the neo-leaflet wire loop, the angle between 15 and 50 degrees.

Inventive Concept 49. The coaptation-assist device according to Inventive Concept 48, wherein the angle is between 35 and 45 degrees.

Inventive Concept 50. The coaptation-assist device according to any one of Inventive Concepts 1-21, further comprising a pouch, which is configured to inflate by blood flow during a cardiac cycle of a heart of the subject, so as to push the coaptation-assist device against one or more of: a ventricular surface of the target native leaflet and an annulus of the native atrioventricular valve, thereby stabilizing the coaptation-assist device with respect to the native atrioventricular valve.

Inventive Concept 51. The coaptation-assist device according to Inventive Concept 50, wherein the coaptation-assist device further comprises a native-leaflet grasper, which is configured to grasp atrial and ventricular surfaces of the target native leaflet, in order to support the neo-leaflet, and to orient the neo-leaflet with respect to the native atrioventricular valve, and wherein the pouch is defined by the native-leaflet grasper.

Inventive Concept 52. The coaptation-assist device according to Inventive Concept 51, wherein the native-leaflet grasper is shaped so as to define first and second portions that are configured to grasp the atrial and the ventricular surfaces of the target native leaflet by sandwiching at least a portion of the atrial and the ventricular surfaces of the target native leaflet between the first and the second portions of the native-leaflet grasper, and wherein the pouch is defined by a ventricularly-facing surface of the second portion of the native-leaflet grasper.

Inventive Concept 53. The coaptation-assist device according to any one of Inventive Concepts 1-21, wherein the coaptation-assist device further comprises a native-leaflet-crossing portion, which is configured to be positioned passing through a puncture through the target native leaflet, and wherein the neo-leaflet is coupled to the loop-shaped ventricular anchor via the native-leaflet-crossing portion.

Inventive Concept 54. The coaptation-assist device according to Inventive Concept 53, wherein the coaptation-assist device comprises a coaptation-assist-device wire loop that is shaped so as to at least partially define the neo-leaflet, the loop-shaped ventricular anchor, and the native-leaflet-crossing portion.

Inventive Concept 55. A system comprising the coaptation-assist device according to any one of Inventive Concepts 1-21, the system further comprising a delivery tube in which the coaptation-assist device is removably disposed in a compressed configuration for minimally-invasive or percutaneous delivery to a heart of the subject.

There is further provided, in accordance with an Inventive Concept 56 of the present invention, a coaptation-assist device for treating a native atrioventricular valve of a subject, the coaptation-assist device comprising:

- a loop-shaped ventricular anchor, which comprises an anchor-loop wire loop, which (i) defines at least a portion of a border of the loop-shaped ventricular anchor, and (ii) is configured (a) to be positioned in a ventricle, extending to a ventricular apical area, and (b) to remain anchored in position against surrounding anatomy, including the ventricular apical area; and
- a neo-leaflet, which extends directly from and is supported by the loop-shaped ventricular anchor and is configured to at least partially replace function of a target native leaflet of the native atrioventricular valve by providing a surface of coaptation for one or more opposing native leaflets that oppose the target native leaflet, when the anchor-loop wire loop is positioned in the ventricle.

Inventive Concept 57. The coaptation-assist device according to Inventive Concept 56, wherein the loop-shaped ventricular anchor is configured to remain anchored in position by force applied by the anchor-loop wire loop to the surrounding anatomy.

Inventive Concept 58. The coaptation-assist device according to Inventive Concept 57, wherein the loop-shaped ventricular anchor is configured to remain anchored in position by radially-outwardly-directed force applied by the anchor-loop wire loop to the surrounding anatomy.

Inventive Concept 59. The coaptation-assist device according to Inventive Concept 56, wherein the loop-shaped ventricular anchor is configured to remain anchored in position by friction between the anchor-loop wire loop and the surrounding anatomy.

Inventive Concept 60. The coaptation-assist device according to Inventive Concept 56, wherein the coaptation-assist device is configured such that when the anchor-loop wire loop is positioned in the ventricle, the anchor-loop wire loop does not extend to a subannular surface of the target native leaflet.

Inventive Concept 61. The coaptation-assist device according to Inventive Concept 56, wherein the loop-shaped ventricular anchor is configured to be atraumatic so as not to penetrate tissue of the surrounding anatomy.

Inventive Concept 62. The coaptation-assist device according to Inventive Concept 56, wherein the coaptation-assist device does not comprise any elements that are configured to penetrate tissue.

Inventive Concept 63. The coaptation-assist device according to Inventive Concept 56, wherein the anchor-loop wire loop comprises metal.

Inventive Concept 64. The coaptation-assist device according to Inventive Concept 56, wherein the anchor-loop wire loop, when unconstrained, is curved along at least 50% of a length of the anchor-loop wire loop, the length measured around the anchor-loop wire loop.

Inventive Concept 65. The coaptation-assist device according to Inventive Concept 64, wherein the anchor-loop wire loop, when unconstrained, is curved along at least 75% of the length of the anchor-loop wire loop.

Inventive Concept 66. The coaptation-assist device according to Inventive Concept 56, wherein the anchor-loop wire loop is shaped as at least 75% of an oval when unconstrained.

Inventive Concept 67. The coaptation-assist device according to Inventive Concept 56, wherein the loop-shaped ventricular anchor further comprises at least one supporting wire, which is coupled to the anchor-loop wire loop at two sites on the anchor-loop wire loop.

Inventive Concept 68. The coaptation-assist device according to Inventive Concept 56, wherein the anchor-loop wire loop is configured to remain anchored in position against one or more ventricular papillary muscles of the ventricular apical area, when the anchor-loop wire loop is positioned in the ventricle.

Inventive Concept 69. The coaptation-assist device according to Inventive Concept 56, wherein the anchor-loop wire loop is shaped so as to define two or more lobes.

Inventive Concept 70. The coaptation-assist device according to Inventive Concept 69, wherein the anchor-loop wire loop is shaped so as to define exactly two lobes.

Inventive Concept 71. The coaptation-assist device according to Inventive Concept 56, wherein the neo-leaflet is configured such that the coaptation surface is generally static throughout a cardiac cycle of the subject upon implantation of the coaptation-assist device in a heart of the subject.

Inventive Concept 72. The coaptation-assist device according to Inventive Concept 56, wherein the coaptation surface has an area of between 2 and 20 cm2.

Inventive Concept 73. The coaptation-assist device according to Inventive Concept 56, wherein the neo-leaflet is configured such that the coaptation surface moves toward and away from the one or more opposing native leaflets during a cardiac cycle of the subject upon implantation of the coaptation-assist device in a heart of the subject.

Inventive Concept 74. The coaptation-assist device according to any one of Inventive Concepts 56-73, further comprising a native-leaflet grasper, which is configured to grasp atrial and ventricular surfaces of the target native leaflet, in order to support the neo-leaflet, and to orient the neo-leaflet with respect to the native atrioventricular valve.

Inventive Concept 75. The coaptation-assist device according to Inventive Concept 74, wherein the native-leaflet grasper is coupled to the loop-shaped ventricular anchor via the neo-leaflet.

Inventive Concept 76. The coaptation-assist device according to Inventive Concept 74, wherein the native-leaflet grasper comprises one or more sub-native-leaflet supports, which are configured to press against one or more portions of the ventricular surface of the target native leaflet when the anchor-loop wire loop is positioned in the ventricle.

Inventive Concept 77. The coaptation-assist device according to Inventive Concept 76, wherein the native-leaflet grasper further comprises one or more supra-annular supports, which are configured to press against an atrial surface of the target native leaflet, such that the one or more sub-native-leaflet supports and the one or more supra-annular supports sandwich and grasp the target native leaflet when the anchor-loop wire loop is positioned in the ventricle.

Inventive Concept 78. The coaptation-assist device according to Inventive Concept 74, wherein the coaptation-assist device is configured such that when the anchor-loop wire loop is positioned in the ventricle and the native-leaflet grasper grasps the atrial and the ventricular surfaces of the target native leaflet, the anchor-loop wire loop does not extend to a subannular surface of the target native leaflet.

Inventive Concept 79. The coaptation-assist device according to any one of Inventive Concepts 56-73, wherein the native atrioventricular valve is a tricuspid valve, and wherein the neo-leaflet is configured to at least partially replace function of the target native leaflet by providing a surface of coaptation for the one or more opposing native leaflets of the tricuspid valve, when the anchor-loop wire loop is positioned in the ventricle.

Inventive Concept 80. The coaptation-assist device according to Inventive Concept 79, wherein the target native leaflet is a native septal leaflet of the tricuspid valve, and wherein the neo-leaflet is configured to at least partially replace function of the septal leaflet by providing a surface of coaptation for one or more of the opposing native posterior and anterior leaflets of the tricuspid valve, when the anchor-loop wire loop is positioned in the ventricle and remains anchored in position against the surrounding anatomy, including the ventricular apical area.

Inventive Concept 81. The coaptation-assist device according to any one of Inventive Concepts 56-73, wherein the native atrioventricular valve is a mitral valve, and wherein the neo-leaflet is configured to at least partially replace function of the target native leaflet by providing a surface of coaptation for the opposing native leaflet of the mitral valve, when the anchor-loop wire loop is positioned in the ventricle.

Inventive Concept 82. The coaptation-assist device according to Inventive Concept 81, wherein the target native leaflet is a native anterior leaflet of the mitral valve, and wherein the neo-leaflet is configured to at least partially replace function of the native anterior leaflet by providing a surface of coaptation for an opposing native posterior leaflet of the mitral valve, when the anchor-loop wire loop is positioned in the ventricle and remains anchored in position against the surrounding anatomy, including the ventricular apical area.

Inventive Concept 83. The coaptation-assist device according to any one of Inventive Concepts 56-73, wherein the coaptation-assist device is configured such that the coaptation surface of the neo-leaflet crosses from an atrial side to a ventricular side of a native valvular plane, when the anchor-loop wire loop is positioned in the ventricle.

Inventive Concept 84. The coaptation-assist device according to any one of Inventive Concepts 56-73, wherein the loop-shaped ventricular anchor further comprises an anchor-loop cover attached to the anchor-loop wire loop.

Inventive Concept 85. The coaptation-assist device according to Inventive Concept 84, wherein the anchor-loop cover comprises one or more thin sheets of material that extend across a space at least partially surrounded by the anchor-loop wire loop.

Inventive Concept 86. The coaptation-assist device according to Inventive Concept 84, wherein the anchor-loop cover comprises braided wires.

Inventive Concept 87. The coaptation-assist device according to Inventive Concept 84, wherein the anchor-loop cover comprises a coating on the anchor-loop wire loop.

Inventive Concept 88. The coaptation-assist device according to any one of Inventive Concepts 56-73, comprising a neo-leaflet wire loop that is shaped so as to at least partially define the neo-leaflet and the loop-shaped ventricular anchor.

Inventive Concept 89. The coaptation-assist device according to any one of Inventive Concepts 56-73, wherein the neo-leaflet comprises a neo-leaflet wire loop that defines at least a portion of a border of the neo-leaflet, and a neo-leaflet cover, which is attached to the neo-leaflet wire loop and provides the surface of coaptation.

Inventive Concept 90. A system comprising the coaptation-assist device according to any one of Inventive Concepts 56-73, the system further comprising a delivery tube in which the coaptation-assist device is removably disposed in a compressed configuration for minimally-invasive or percutaneous delivery to a heart of the subject.

There is still further provided, in accordance with an Inventive Concept 91 of the present invention, a coaptation-assist device for treating a native atrioventricular valve of a subject, the coaptation-assist device comprising:

- a loop-shaped ventricular anchor, which (i) comprises a braided flat sheet comprising braided wires, and (ii) is configured (a) to be positioned in a ventricle, extending between a ventricular apical area and a subannular surface of a target native leaflet of the native atrioventricular valve, and (b) to remain anchored in position by force applied by the loop-shaped ventricular anchor to surrounding anatomy, including the subannular surface, a ventricular wall, and the ventricular apical area; and
- a neo-leaflet, which is supported by the loop-shaped ventricular anchor and is configured to at least partially replace function of the target native leaflet by providing a surface of coaptation for one or more opposing native leaflets that oppose the target native leaflet, when the loop-shaped ventricular anchor is positioned in the ventricle.

Inventive Concept 92. The coaptation-assist device according to Inventive Concept 91, wherein the loop-shaped ventricular anchor is configured to remain anchored in position by radially-outwardly-directed force applied by the loop-shaped ventricular anchor to the surrounding anatomy.

Inventive Concept 93. The coaptation-assist device according to Inventive Concept 91, wherein the loop-shaped ventricular anchor is configured to remain anchored in position by friction between the loop-shaped ventricular anchor and the surrounding anatomy.

Inventive Concept 94. The coaptation-assist device according to Inventive Concept 91, wherein the loop-shaped ventricular anchor is configured to be atraumatic so as not to penetrate tissue of the surrounding anatomy.

Inventive Concept 95. The coaptation-assist device according to Inventive Concept 91, wherein the coaptation-assist device does not comprise any elements that are configured to penetrate tissue.

Inventive Concept 96. The coaptation-assist device according to Inventive Concept 91, wherein the braided wires comprise metal.

Inventive Concept 97. The coaptation-assist device according to Inventive Concept 91, wherein the loop-shaped ventricular anchor is shaped as at least 75% of an oval when unconstrained.

Inventive Concept 98. The coaptation-assist device according to Inventive Concept 91, wherein the loop-shaped ventricular anchor is configured to remain anchored in position against the subannular surface, the ventricular wall, and one or more ventricular papillary muscles of the ventricular apical area, when the loop-shaped ventricular anchor is positioned in the ventricle.

Inventive Concept 99. The coaptation-assist device according to Inventive Concept 91, wherein the neo-leaflet is configured such that the coaptation surface is generally static throughout a cardiac cycle of the subject upon implantation of the coaptation-assist device in a heart of the subject.

Inventive Concept 100. The coaptation-assist device according to Inventive Concept 91, wherein the coaptation surface has an area of between 2 and 20 cm2.

Inventive Concept 101. The coaptation-assist device according to Inventive Concept 91, wherein the coaptation-assist device is configured such that when unconstrained, either:

an angle is defined between (a) an anchor-loop best-fit plane defined by the anchor-loop wire loop and (b) a neo-leaflet best-fit plane defined by the coaptation surface, the angle less than 20 degrees, or the anchor-loop best-fit plane and the neo-leaflet best-fit plane are parallel with each other.

Inventive Concept 102. The coaptation-assist device according to Inventive Concept 91, wherein the neo-leaflet is configured such that the coaptation surface moves toward and away from the one or more opposing native leaflets during a cardiac cycle of the subject upon implantation of the coaptation-assist device in a heart of the subject.

Inventive Concept 103. The coaptation-assist device according to any one of Inventive Concepts 91-102, further comprising a native-leaflet grasper, which is configured to grasp atrial and ventricular surfaces of the target native leaflet, in order to support the neo-leaflet, and to orient the neo-leaflet with respect to the native atrioventricular valve.

Inventive Concept 104. The coaptation-assist device according to Inventive Concept 103, wherein the neo-leaflet is coupled to the loop-shaped ventricular anchor via the native-leaflet grasper.

Inventive Concept 105. The coaptation-assist device according to Inventive Concept 103, wherein the native-leaflet grasper is shaped so as to define first and second portions that are configured to grasp the atrial and the ventricular surfaces of the target native leaflet by sandwiching at least a portion of the atrial and the ventricular surfaces of the target native leaflet between the first and the second portions of the native-leaflet grasper.

Inventive Concept 106. The coaptation-assist device according to Inventive Concept 105, wherein the first and the second portions are configured to fold toward each other so as to grasp the atrial and the ventricular surfaces of the target native leaflet by sandwiching the at least a portion of the atrial and the ventricular surfaces of the target native leaflet between the first and the second portions of the native-leaflet grasper.

Inventive Concept 107. The coaptation-assist device according to any one of Inventive Concepts 91-102, wherein the ventricular wall is a ventricular septal wall, and wherein the loop-shaped ventricular anchor is configured to be remain anchored in position against the surrounding anatomy, including the subannular surface, the ventricular septal wall, and the ventricular apical area.

Inventive Concept 108. The coaptation-assist device according to any one of Inventive Concepts 91-102, wherein the native atrioventricular valve is a tricuspid valve, and wherein the neo-leaflet is configured to at least partially replace function of the target native leaflet by providing a surface of coaptation for the one or more opposing native leaflets of the tricuspid valve, when the loop-shaped ventricular anchor is positioned in the ventricle.

Inventive Concept 109. The coaptation-assist device according to Inventive Concept 108, wherein the target native leaflet is a native septal leaflet of the tricuspid valve, wherein the ventricular wall is a ventricular septal wall, and wherein the neo-leaflet is configured to at least partially replace function of the septal leaflet by providing a surface of coaptation for one or more of the opposing native posterior and anterior leaflets of the tricuspid valve, when the loop-shaped ventricular anchor is positioned in the ventricle and remains anchored in position against the surrounding anatomy, including the subannular surface, the ventricular septal wall, and the ventricular apical area.

Inventive Concept 110. The coaptation-assist device according to any one of Inventive Concepts 91-102, wherein the native atrioventricular valve is a mitral valve, and wherein the neo-leaflet is configured to at least partially replace function of the target native leaflet by providing a surface of coaptation for the opposing native leaflet of the mitral valve, when the loop-shaped ventricular anchor is positioned in the ventricle.

Inventive Concept 111. The coaptation-assist device according to Inventive Concept 110, wherein the target native leaflet is a native anterior leaflet of the mitral valve, wherein the ventricular wall is a ventricular septal wall, and wherein the neo-leaflet is configured to at least partially replace function of the native anterior leaflet by providing a surface of coaptation for an opposing native posterior leaflet of the mitral valve, when the loop-shaped ventricular anchor is positioned in the ventricle and remains anchored in position against the surrounding anatomy, including the subannular surface, the ventricular septal wall, and the ventricular apical area.

Inventive Concept 112. The coaptation-assist device according to any one of Inventive Concepts 91-102, wherein the coaptation-assist device is configured such that the coaptation surface of the neo-leaflet crosses from an atrial side to a ventricular side of a native valvular plane, when the loop-shaped ventricular anchor is positioned in the ventricle.

Inventive Concept 113. The coaptation-assist device according to any one of Inventive Concepts 91-102, wherein the loop-shaped ventricular anchor further comprises an anchor cover, which is attached to and covers all or a portion of the braided flat sheet.

Inventive Concept 114. The coaptation-assist device according to Inventive Concept 113, wherein the anchor-loop cover comprises one or more thin sheets of material attached to the braided flat sheet.

Inventive Concept 115. A system comprising the coaptation-assist device according to any one of Inventive Concepts 91-102, the system further comprising a delivery tube in which the coaptation-assist device is removably disposed in a compressed configuration for minimally-invasive or percutaneous delivery to a heart of the subject.

There is additionally provided, in accordance with an Inventive Concept 116 of the present invention, a method for treating a native atrioventricular valve of a subject, the method comprising:

positioning a loop-shaped ventricular anchor of a coaptation-assist device in a ventricle, such that an anchor-loop wire loop of the loop-shaped ventricular anchor extends between a ventricular apical area and a subannular surface of a target native leaflet of the native atrioventricular valve, such that the anchor-loop wire loop remains anchored in position against surrounding anatomy, including the subannular surface, a ventricular wall, and the ventricular apical area, wherein the anchor-loop wire loop defines at least a portion of a border of the loop-shaped ventricular anchor; and positioning a neo-leaflet of the coaptation-assist device such that the neo-leaflet at least partially replaces function of the target native leaflet by providing a surface of coaptation for one or more opposing native leaflets that oppose the target native leaflet, when the anchor-loop wire loop is positioned in the ventricle, wherein the neo-leaflet is supported by the loop-shaped ventricular anchor.

Inventive Concept 117. The method according to Inventive Concept 116, wherein positioning the loop-shaped ventricular anchor comprises positioning the loop-shaped ventricular anchor such that the anchor-loop wire loop remains anchored in position by force applied by the anchor-loop wire loop to the surrounding anatomy.

Inventive Concept 118. The method according to Inventive Concept 117, wherein positioning the loop-shaped ventricular anchor comprises positioning the loop-shaped ventricular anchor such that the anchor-loop wire loop remains anchored in position by radially-outwardly-directed force applied by the anchor-loop wire loop to the surrounding anatomy.

Inventive Concept 119. The method according to Inventive Concept 116, wherein positioning the loop-shaped ventricular anchor comprises positioning the anchor-loop wire loop such that the anchor-loop wire loop remains anchored in position by friction between the anchor-loop wire loop and the surrounding anatomy.

Inventive Concept 120. The method according to Inventive Concept 116, wherein the loop-shaped ventricular anchor is configured to be atraumatic, and wherein positioning the loop-shaped ventricular anchor does not comprise penetrating tissue of the surrounding anatomy with the loop-shaped ventricular anchor.

Inventive Concept 121. The method according to Inventive Concept 116, wherein the method does not comprise penetrating tissue with any elements of the coaptation-assist device.

Inventive Concept 122. The method according to Inventive Concept 116, further comprising positioning a native-leaflet grasper of the coaptation-assist device to grasp atrial and ventricular surfaces of the target native leaflet, in order to support the neo-leaflet, and to orient the neo-leaflet with respect to the native atrioventricular valve.

Inventive Concept 123. The method according to Inventive Concept 122, wherein the neo-leaflet is coupled to the loop-shaped ventricular anchor via the native-leaflet grasper.

Inventive Concept 124. The method according to Inventive Concept 123, comprising a wire loop that is shaped so as to at least partially define the neo-leaflet and the native-leaflet grasper.

Inventive Concept 125. The method according to Inventive Concept 122, wherein positioning the native-leaflet grasper to grasp atrial and ventricular surfaces of the target native leaflet comprises sandwiching at least a portion of the atrial and the ventricular surfaces of the target native leaflet between the first and the second portions of the native-leaflet grasper.

Inventive Concept 126. The method according to Inventive Concept 125, wherein sandwiching at least a portion of the atrial and the ventricular surfaces of the target native leaflet comprises folding the first and the second portions of the native-leaflet grasper toward each other so as to grasp the atrial and the ventricular surfaces of the target native leaflet.

Inventive Concept 127. The method according to Inventive Concept 126, wherein folding the first and the second portions of the native-leaflet grasper toward each other comprises extending, around the free edge of the target native leaflet, a third portion defined by the native-leaflet grasper at a fold between the first and the second portions of the native-leaflet grasper.

Inventive Concept 128. The method according to Inventive Concept 122, wherein positioning the native-leaflet grasper to grasp the ventricular surface of the target native leaflet comprises pressing one or more sub-native-leaflet supports of the native-leaflet grasper against one or more portions of the ventricular surface of the target native leaflet when the anchor-loop wire loop is positioned in the ventricle.

Inventive Concept 129. The method according to Inventive Concept 128, wherein positioning the native-leaflet grasper to grasp the atrial surface of the target native leaflet comprises pressing one or more supra-annular supports of the native-leaflet grasper against an atrial surface of the target native leaflet, such that the one or more sub-native-leaflet supports and the one or more supra-annular supports sandwich and grasp the target native leaflet when the anchor-loop wire loop is positioned in the ventricle.

Inventive Concept 130. The method according to Inventive Concept 122, wherein positioning the native-leaflet grasper to grasp the atrial surface of the target native leaflet comprises pressing one or more supra-annular supports of the native-leaflet grasper against an atrial surface of the target native leaflet when the anchor-loop wire loop is positioned in the ventricle.

Inventive Concept 131. The method according to Inventive Concept 116, wherein positioning the loop-shaped ventricular anchor comprises positioning the loop-shaped ventricular anchor such that the anchor-loop wire loop remains anchored in position against the subannular surface, the ventricular wall, and one or more ventricular papillary muscles of the ventricular apical area.

Inventive Concept 132. The method according to Inventive Concept 116, wherein the anchor-loop wire loop is shaped so as to define two or more lobes.

Inventive Concept 133. The method according to Inventive Concept 132, wherein the anchor-loop wire loop is shaped so as to define exactly two lobes.

Inventive Concept 134. The method according to Inventive Concept 116, wherein the ventricular wall is a ventricular septal wall, and wherein positioning the loop-shaped ventricular anchor comprises positioning the loop-shaped ventricular anchor such that the anchor-loop wire loop remains anchored in position against the surrounding anatomy, including the subannular surface, the ventricular septal wall, and the ventricular apical area.

Inventive Concept 135. The method according to Inventive Concept 116, wherein the native atrioventricular valve is a tricuspid valve, and wherein positioning the neo-leaflet comprises positioning the neo-leaflet such that the neo-leaflet at least partially replaces function of the target native leaflet by providing a surface of coaptation for one or more opposing native leaflets of the tricuspid valve, when the anchor-loop wire loop is positioned in the ventricle.

Inventive Concept 136. The method according to Inventive Concept 135, wherein the target native leaflet is a native septal leaflet of the tricuspid valve, wherein the ventricular wall is a ventricular septal wall, and wherein positioning the neo-leaflet comprises positioning the neo-leaflet such that the neo-leaflet at least partially replaces function of the septal leaflet by providing a surface of coaptation for one or more of the opposing native posterior and anterior leaflets of the tricuspid valve, when the anchor-loop wire loop is positioned in the ventricle and remains anchored in position against the surrounding anatomy, including the subannular surface, the ventricular septal wall, and the ventricular apical area.

Inventive Concept 137. The method according to Inventive Concept 116, wherein the native atrioventricular valve is a mitral valve, and wherein positioning the neo-leaflet comprises positioning the neo-leaflet such that the neo-leaflet at least partially replaces function of the target native leaflet by providing a surface of coaptation for the opposing native leaflet of the mitral valve, when the anchor-loop wire loop is positioned in the ventricle.

Inventive Concept 138. The method according to Inventive Concept 137, wherein the target native leaflet is a native anterior leaflet of the mitral valve, wherein the ventricular wall is a ventricular septal wall, and wherein positioning the neo-leaflet comprises positioning the neo-leaflet such that the neo-leaflet at least partially replaces function of the native anterior leaflet by providing a surface of coaptation for an opposing native posterior leaflet of the mitral valve, when the anchor-loop wire loop is positioned in the ventricle and remains anchored in position against the surrounding anatomy, including the subannular surface, the ventricular septal wall, and the ventricular apical area.

Inventive Concept 139. The method according to Inventive Concept 116, wherein positioning the neo-leaflet comprises positioning the neo-leaflet such that the coaptation surface of the neo-leaflet crosses from an atrial side to a ventricular side of a native valvular plane, when the anchor-loop wire loop is positioned in the ventricle.

Inventive Concept 140. The method according to Inventive Concept 116, wherein positioning the neo-leaflet comprises positioning the neo-leaflet such that the coaptation surface is generally static throughout a cardiac cycle of the subject upon implantation of the coaptation-assist device in a heart of the subject.

Inventive Concept 141. The method according to Inventive Concept 116, wherein positioning the neo-leaflet comprises positioning the neo-leaflet such that the coaptation surface moves toward and away from the one or more opposing native leaflets during a cardiac cycle of the subject upon implantation of the coaptation-assist device in a heart of the subject.

Inventive Concept 142. The method according to Inventive Concept 116, wherein the anchor-loop wire loop is shaped as a closed loop.

Inventive Concept 143. The method according to Inventive Concept 116, wherein the anchor-loop wire loop comprises metal.

Inventive Concept 144. The method according to Inventive Concept 116, wherein the loop-shaped ventricular anchor further comprises an anchor-loop cover attached to the anchor-loop wire loop.

Inventive Concept 145. The method according to Inventive Concept 144, wherein the anchor-loop cover comprises one or more thin sheets of material that extend across a space at least partially surrounded by the anchor-loop wire loop.

Inventive Concept 146. The method according to Inventive Concept 144, wherein the anchor-loop cover comprises braided wires.

Inventive Concept 147. The method according to Inventive Concept 144, wherein the anchor-loop cover comprises a coating on the anchor-loop wire loop.

Inventive Concept 148. The method according to Inventive Concept 116, wherein the loop-shaped ventricular anchor further comprises at least one supporting wire, which is coupled to the anchor-loop wire loop at two sites on the anchor-loop wire loop.

Inventive Concept 149. The method according to Inventive Concept 116, comprising a coaptation-assist-device wire loop that is shaped so as to at least partially define the neo-leaflet and the loop-shaped ventricular anchor.

Inventive Concept 150. The method according to Inventive Concept 149, wherein the coaptation-assist-device wire loop is shaped so as to further at least partially define a native-leaflet grasper, which is configured to grasp atrial and ventricular surfaces of the target native leaflet, in order to support the neo-leaflet, and to orient the neo-leaflet with respect to the native atrioventricular valve.

Inventive Concept 151. The method according to Inventive Concept 150, wherein the coaptation-assist-device wire loop is shaped so as to at least partially define the native-leaflet grasper along the coaptation-assist-device wire loop between the neo-leaflet and the loop-shaped ventricular anchor.

Inventive Concept 152. The method according to Inventive Concept 116, wherein the neo-leaflet comprises a neo-leaflet wire loop that defines at least a portion of a border of the neo-leaflet, and a neo-leaflet cover, which is attached to the neo-leaflet wire loop and provides the surface of coaptation.

Inventive Concept 153. The method according to Inventive Concept 116, wherein the coaptation-assist device further comprises a native-leaflet-crossing portion, and wherein the neo-leaflet is coupled to the loop-shaped ventricular anchor via the native-leaflet-crossing portion, and wherein the method further comprises forming a puncture through the target native leaflet, and positioning the native-leaflet-crossing portion passing through the puncture.

Inventive Concept 154. The method according to Inventive Concept 153, wherein the coaptation-assist device comprises a coaptation-assist-device wire loop that is shaped so as to at least partially define the neo-leaflet, the loop-shaped ventricular anchor, and the native-leaflet-crossing portion.

Inventive Concept 155. The method according to Inventive Concept 116, further comprising, before positioning the loop-shaped ventricular anchor and the neo-leaflet, minimally-invasively or percutaneously delivering the coaptation-assist device to a heart of the subject while the coaptation-assist device is removably disposed in a delivery tube in a compressed configuration.

There is yet additionally provided, in accordance with an Inventive Concept 156 of the present invention, a method for treating a native atrioventricular valve of a subject, the method comprising:

positioning a loop-shaped ventricular anchor of a coaptation-assist device in a ventricle, such that an anchor-loop wire loop of the loop-shaped ventricular anchor extends to a ventricular apical area, such that the anchor-loop wire remains anchored in position against surrounding anatomy, including the ventricular apical area, wherein the anchor-loop wire loop defines at least a portion of a border of the loop-shaped ventricular anchor; and positioning a neo-leaflet of the coaptation-assist device such that the neo-leaflet at least partially replaces function of a target native leaflet of the native atrioventricular valve by providing a surface of coaptation for one or more opposing native leaflets that oppose the target native leaflet, when the anchor-loop wire loop is positioned in the ventricle, wherein the neo-leaflet extends directly from and is supported by the loop-shaped ventricular anchor.

Inventive Concept 157. The method according to Inventive Concept 156, wherein positioning the loop-shaped ventricular anchor comprises positioning the loop-shaped ventricular anchor such that the anchor-loop wire loop remains anchored in position by force applied by the anchor-loop wire loop to the surrounding anatomy.

Inventive Concept 158. The method according to Inventive Concept 157, wherein positioning the loop-shaped ventricular anchor comprises positioning the loop-shaped ventricular anchor such that the anchor-loop wire loop remains anchored in position by radially-outwardly-directed force applied by the anchor-loop wire loop to the surrounding anatomy.

Inventive Concept 159. The method according to Inventive Concept 156, wherein positioning the loop-shaped ventricular anchor comprises positioning the loop-shaped ventricular anchor such that the anchor-loop wire loop remains anchored in position by friction between the anchor-loop wire loop and the surrounding anatomy.

Inventive Concept 160. The method according to Inventive Concept 156, wherein positioning the loop-shaped ventricular anchor in the ventricle comprises positioning the loop-shaped ventricular anchor in the ventricle such that the anchor-loop wire loop does not extend to a subannular surface of the target native leaflet.

Inventive Concept 161. The method according to Inventive Concept 156, wherein the loop-shaped ventricular anchor is configured to be atraumatic, and wherein positioning the loop-shaped ventricular anchor does not comprise penetrating tissue of the surrounding anatomy with the loop-shaped ventricular anchor.

Inventive Concept 162. The method according to Inventive Concept 156, wherein the method does not comprise penetrating tissue with any elements of the coaptation-assist device.

Inventive Concept 163. The method according to Inventive Concept 156, further comprising positioning a native-leaflet grasper of the coaptation-assist device to grasp atrial and ventricular surfaces of the target native leaflet, in order to support the neo-leaflet, and to orient the neo-leaflet with respect to the native atrioventricular valve.

Inventive Concept 164. The method according to Inventive Concept 163, wherein the native-leaflet grasper is coupled to the loop-shaped ventricular anchor via the neo-leaflet.

Inventive Concept 165. The method according to Inventive Concept 163, wherein positioning the native-leaflet grasper to grasp the ventricular surface of the target native leaflet comprises pressing one or more sub-native-leaflet supports of the native-leaflet grasper against one or more portions of the ventricular surface of the target native leaflet when the anchor-loop wire loop is positioned in the ventricle.

Inventive Concept 166. The method according to Inventive Concept 165, wherein positioning the native-leaflet grasper to grasp the atrial surface of the target native leaflet comprises pressing one or more supra-annular supports of the native-leaflet grasper against an atrial surface of the target native leaflet, such that the one or more sub-native-leaflet supports and the one or more supra-annular supports sandwich and grasp the target native leaflet when the anchor-loop wire loop is positioned in the ventricle.

Inventive Concept 167. The method according to Inventive Concept 163, wherein positioning the native-leaflet grasper to grasp the atrial surface of the target native leaflet comprises pressing one or more supra-annular supports of the native-leaflet grasper against an atrial surface of the target native leaflet when the anchor-loop wire loop is positioned in the ventricle.

Inventive Concept 168. The method according to Inventive Concept 156, wherein positioning the loop-shaped ventricular anchor comprises positioning the loop-shaped ventricular anchor such that the anchor-loop wire loop remains anchored in position against one or more ventricular papillary muscles of the ventricular apical area.

Inventive Concept 169. The method according to Inventive Concept 156, wherein the anchor-loop wire loop is shaped so as to define two or more lobes.

Inventive Concept 170. The method according to Inventive Concept 169, wherein the anchor-loop wire loop is shaped so as to define exactly two lobes.

Inventive Concept 171. The method according to Inventive Concept 156, wherein the native atrioventricular valve is a tricuspid valve, and wherein positioning the neo-leaflet comprises positioning the neo-leaflet such that the neo-leaflet at least partially replaces function of the target native leaflet by providing a surface of coaptation for one or more opposing native leaflets of the tricuspid valve, when the anchor-loop wire loop is positioned in the ventricle.

Inventive Concept 172. The method according to Inventive Concept 171, wherein the target native leaflet is a native septal leaflet of the tricuspid valve, and wherein positioning the neo-leaflet comprises positioning the neo-leaflet such that the neo-leaflet at least partially replaces function of the septal leaflet by providing a surface of coaptation for one or more of the opposing native posterior and anterior leaflets of the tricuspid valve, when the anchor-loop wire loop is positioned in the ventricle and remains anchored in position against the surrounding anatomy, including the ventricular apical area.

Inventive Concept 173. The method according to Inventive Concept 156, wherein the native atrioventricular valve is a mitral valve, and wherein positioning the neo-leaflet comprises positioning the neo-leaflet such that the neo-leaflet at least partially replaces function of the target native leaflet by providing a surface of coaptation for the opposing native leaflet of the mitral valve, when the anchor-loop wire loop is positioned in the ventricle.

Inventive Concept 174. The method according to Inventive Concept 173, wherein the target native leaflet is a native anterior leaflet of the mitral valve, and wherein positioning the neo-leaflet comprises positioning the neo-leaflet such that the neo-leaflet at least partially replaces function of the native anterior leaflet by providing a surface of coaptation for an opposing native posterior leaflet of the mitral valve, when the anchor-loop wire loop is positioned in the ventricle and remains anchored in position against the surrounding anatomy, including the ventricular apical area.

Inventive Concept 175. The method according to Inventive Concept 156, wherein positioning the neo-leaflet comprises positioning the neo-leaflet such that the coaptation surface of the neo-leaflet crosses from an atrial side to a ventricular side of a native valvular plane, when the anchor-loop wire loop is positioned in the ventricle.

Inventive Concept 176. The method according to Inventive Concept 156, wherein positioning the neo-leaflet comprises positioning the neo-leaflet such that the coaptation surface is generally static throughout a cardiac cycle of the subject upon implantation of the coaptation-assist device in a heart of the subject.

Inventive Concept 177. The method according to Inventive Concept 156, wherein positioning the neo-leaflet comprises positioning the neo-leaflet such that the coaptation surface moves toward and away from the one or more opposing native leaflets during a cardiac cycle of the subject upon implantation of the coaptation-assist device in a heart of the subject.

Inventive Concept 178. The method according to Inventive Concept 156, wherein the anchor-loop wire loop comprises metal.

Inventive Concept 179. The method according to Inventive Concept 156, wherein the loop-shaped ventricular anchor further comprises an anchor-loop cover attached to the anchor-loop wire loop.

Inventive Concept 180. The method according to Inventive Concept 179, wherein the anchor-loop cover comprises one or more thin sheets of material that extend across a space at least partially surrounded by the anchor-loop wire loop.

Inventive Concept 181. The method according to Inventive Concept 179, wherein the anchor-loop cover comprises braided wires.

Inventive Concept 182. The method according to Inventive Concept 179, wherein the anchor-loop cover comprises a coating on the anchor-loop wire loop.

Inventive Concept 183. The method according to Inventive Concept 156, wherein the loop-shaped ventricular anchor further comprises at least one supporting wire, which is coupled to the anchor-loop wire loop at two sites on the anchor-loop wire loop.

Inventive Concept 184. The method according to Inventive Concept 156, comprising a coaptation-assist-device wire loop that is shaped so as to at least partially define the neo-leaflet and the loop-shaped ventricular anchor.

Inventive Concept 185. The method according to Inventive Concept 156, wherein the neo-leaflet comprises a neo-leaflet wire loop that defines at least a portion of a border of the neo-leaflet, and a neo-leaflet cover, which is attached to the neo-leaflet wire loop and provides the surface of coaptation.

Inventive Concept 186. The method according to Inventive Concept 156, further comprising, before positioning the loop-shaped ventricular anchor and the neo-leaflet, minimally-invasively or percutaneously delivering the coaptation-assist device to a heart of the subject while the coaptation-assist device is removably disposed in a delivery tube in a compressed configuration.

There is also provided, in accordance with an Inventive Concept 187 of the present invention, a method for treating a native atrioventricular valve of a subject, the method comprising:

- positioning a loop-shaped ventricular anchor of a coaptation-assist device in a ventricle, such that the loop-shaped ventricular anchor extends between a ventricular apical area and a subannular surface of a target native leaflet of the native atrioventricular valve, and remains anchored in position by force applied by the loop-shaped ventricular anchor to surrounding anatomy, including the subannular surface, a ventricular wall, and the ventricular apical area, wherein the loop-shaped ventricular anchor comprises a braided flat sheet comprising braided wires; and
- positioning a neo-leaflet of the coaptation-assist device such that the neo-leaflet at least partially replaces function of the target native leaflet by providing a surface of coaptation for one or more opposing native leaflets that oppose the target native leaflet, when the loop-shaped ventricular anchor is positioned in the ventricle, wherein the neo-leaflet is supported by the loop-shaped ventricular anchor.

Inventive Concept 188. The method according to Inventive Concept 187, wherein positioning the loop-shaped ventricular anchor comprises positioning the loop-shaped ventricular anchor such that the loop-shaped ventricular anchor remains anchored in position by radially-outwardly-directed force applied by the loop-shaped ventricular anchor to the surrounding anatomy.

Inventive Concept 189. The method according to Inventive Concept 187, wherein positioning the loop-shaped ventricular anchor comprises positioning the loop-shaped ventricular anchor such that the loop-shaped ventricular anchor remains anchored in position by friction between the loop-shaped ventricular anchor and the surrounding anatomy.

Inventive Concept 190. The method according to Inventive Concept 187, wherein the loop-shaped ventricular anchor is configured to be atraumatic, and wherein positioning the loop-shaped ventricular anchor does not comprise penetrating tissue of the surrounding anatomy with the loop-shaped ventricular anchor.

Inventive Concept 191. The method according to Inventive Concept 187, wherein the method does not comprise penetrating tissue with any elements of the coaptation-assist device.

Inventive Concept 192. The method according to Inventive Concept 187, wherein the braided wires comprise metal.

Inventive Concept 193. The method according to Inventive Concept 187, wherein the loop-shaped ventricular anchor is shaped as at least 75% of an oval when unconstrained.

Inventive Concept 194. The method according to Inventive Concept 187, wherein positioning the neo-leaflet comprises positioning the neo-leaflet such that the coaptation surface is generally static throughout a cardiac cycle of the subject upon implantation of the coaptation-assist device in a heart of the subject.

Inventive Concept 195. The method according to Inventive Concept 187, wherein positioning the neo-leaflet comprises positioning the neo-leaflet such that the coaptation surface moves toward and away from the one or more opposing native leaflets during a cardiac cycle of the subject upon implantation of the coaptation-assist device in a heart of the subject.

Inventive Concept 196. The method according to Inventive Concept 187, further comprising positioning a native-leaflet grasper of the coaptation-assist device to grasp atrial and ventricular surfaces of the target native leaflet, in order to support the neo-leaflet, and to orient the neo-leaflet with respect to the native atrioventricular valve.

Inventive Concept 197. The method according to Inventive Concept 196, wherein the neo-leaflet is coupled to the loop-shaped ventricular anchor via the native-leaflet grasper.

Inventive Concept 198. The method according to Inventive Concept 196, wherein positioning the native-leaflet grasper to grasp atrial and ventricular surfaces of the target native leaflet comprises sandwiching at least a portion of the atrial and the ventricular surfaces of the target native leaflet between first and second portions of the native-leaflet grasper.

Inventive Concept 199. The method according to Inventive Concept 198, wherein sandwiching at least a portion of the atrial and the ventricular surfaces of the target native leaflet comprising folding the first and the second portions toward each other so as to grasp the atrial and the ventricular surfaces of the target native leaflet.

Inventive Concept 200. The method according to Inventive Concept 187, wherein positioning the loop-shaped ventricular anchor comprises positioning the loop-shaped ventricular anchor such that the loop-shaped ventricular anchor remains anchored in position against the subannular surface, the ventricular wall, and one or more ventricular papillary muscles of the ventricular apical area.

Inventive Concept 201. The method according to Inventive Concept 187, wherein the ventricular wall is a ventricular septal wall, and wherein positioning the loop-shaped ventricular anchor comprises positioning the loop-shaped ventricular anchor such that the loop-shaped ventricular anchor remains anchored in position against the surrounding anatomy, including the subannular surface, the ventricular septal wall, and the ventricular apical area.

Inventive Concept 202. The method according to Inventive Concept 187, wherein the native atrioventricular valve is a tricuspid valve, and wherein positioning the neo-leaflet comprises positioning the neo-leaflet such that the neo-leaflet at least partially replaces function of the target native leaflet by providing a surface of coaptation for one or more opposing native leaflets of the tricuspid valve, when the loop-shaped ventricular anchor is positioned in the ventricle.

Inventive Concept 203. The method according to Inventive Concept 202, wherein the target native leaflet is a native septal leaflet of the tricuspid valve, wherein the ventricular wall is a ventricular septal wall, and wherein positioning the neo-leaflet comprises positioning the neo-leaflet such that the neo-leaflet at least partially replaces function of the septal leaflet by providing a surface of coaptation for one or more of the opposing native posterior and anterior leaflets of the tricuspid valve, when the loop-shaped ventricular anchor is positioned in the ventricle and remains anchored in position against the surrounding anatomy, including the subannular surface, the ventricular septal wall, and the ventricular apical area.

Inventive Concept 204. The method according to Inventive Concept 187, wherein the native atrioventricular valve is a mitral valve, and wherein positioning the neo-leaflet comprises positioning the neo-leaflet such that the neo-leaflet at least partially replaces function of the target native leaflet by providing a surface of coaptation for the opposing native leaflet of the mitral valve, when the loop-shaped ventricular anchor is positioned in the ventricle.

Inventive Concept 205. The method according to Inventive Concept 204, wherein the target native leaflet is a native anterior leaflet of the mitral valve, wherein the ventricular wall is a ventricular septal wall, and wherein positioning the neo-leaflet comprises positioning the neo-leaflet such that the neo-leaflet at least partially replaces function of the native anterior leaflet by providing a surface of coaptation for an opposing native posterior leaflet of the mitral valve, when the loop-shaped ventricular anchor is positioned in the ventricle and remains anchored in position against the surrounding anatomy, including the subannular surface, the ventricular septal wall, and the ventricular apical area.

Inventive Concept 206. The method according to Inventive Concept 187, wherein positioning the neo-leaflet comprises positioning the neo-leaflet such that the coaptation surface of the neo-leaflet crosses from an atrial side to a ventricular side of a native valvular plane, when the loop-shaped ventricular anchor is positioned in the ventricle.

Inventive Concept 207. The method according to Inventive Concept 187, wherein the loop-shaped ventricular anchor further comprises an anchor-loop cover, which is attached to and covers all or a portion of the braided flat sheet.

Inventive Concept 208. The method according to Inventive Concept 207, wherein the anchor-loop cover comprises one or more thin sheets of material attached to the braided flat sheet.

Inventive Concept 209. The method according to Inventive Concept 187, further comprising, before positioning the loop-shaped ventricular anchor and the neo-leaflet, minimally-invasively or percutaneously delivering the coaptation-assist device to a heart of the subject while the coaptation-assist device is removably disposed in a delivery tube in a compressed configuration.

The present invention will be more fully understood from the following detailed description of embodiments thereof, taken together with the drawings, in which:

BRIEF DESCRIPTION OF THE DRAWINGS

FIGS. 3A-K are highly schematic illustrations of loop-shaped ventricular anchors, respectively, in accordance with respective applications of the present invention:

FIGS. 10D-F are schematic illustrations of another coaptation-assist device, in accordance with an application of the present invention:

FIGS. 13A-E are schematic illustrations of another coaptation-assist device, in accordance with an application of the present invention;

FIGS. 16A-F are schematic illustrations of another coaptation-assist device, in accordance with an application of the present invention;

FIGS. 20A-B are schematic illustrations of yet another coaptation-assist device, in accordance with an application of the present invention:

DETAILED DESCRIPTION OF EMBODIMENTS

FIGS. 1A-E are schematic illustrations of a coaptation-assist device 20 for treating a native valve 22 of a subject, in accordance with an application of the present invention. Typically, the native valve suffers from a valvular pathology, such as functional mitral or tricuspid regurgitation, often characterized by lack of mobility of the leaflets in the valve. The native valve is typically an atrioventricular valve, i.e., the tricuspid or the mitral valve.

Figure 2:
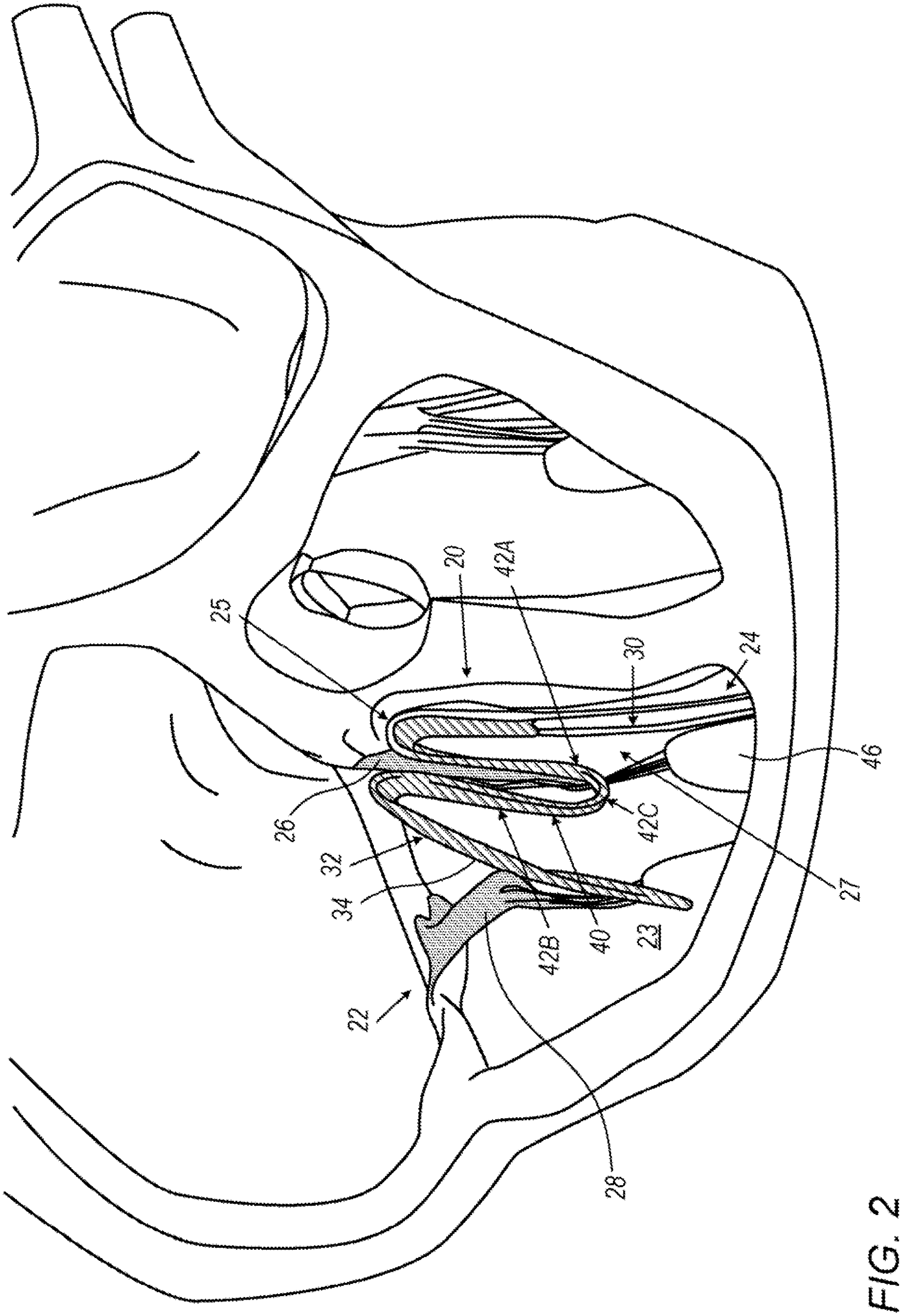
FIG. 2 is a schematic illustration of the coaptation-assist device of FIGS. 1A-E and 2 implanted in a native valve, in accordance with an application of the present invention.

Reference is additionally made to FIG. 2, which is a schematic illustration of coaptation-assist device 20 implanted in native valve 22, in accordance with an application of the present invention. In the particular implantation shown in FIG. 2, native valve 22 is the tricuspid valve. FIG. 2 is a cross-sectional view of the heart, with an anterior portion of the heart, including the native anterior leaflet of the tricuspid valve, removed, such that only the septal and posterior leaflets are shown. (A native "valve" is also known in the art as a native "valvular apparatus.")

Coaptation-assist device 20 comprises a loop-shaped ventricular anchor 30, i.e., a ventricular anchor that has a loop-shaped border, and a neo-leaflet 32, which is supported by loop-shaped ventricular anchor 30. Loop-shaped ventricular anchor 30 is disposed distally to neo-leaflet 32. As used in the present application, including in the claims and Inventive concepts, the term "neo-leaflet" means "prosthetic leaflet."

Typically, loop-shaped ventricular anchor 30 comprises an anchor-loop wire loop 50 that defines at least a portion of the border of the loop-shaped ventricular anchor. Anchor-loop wire loop 50 comprises metal or another semi-rigid material. The material of anchor-loop wire loop 50 is either self-expanding or mechanically expandable. For example, anchor-loop wire loop 50 may comprise a shape-memory alloy, such as Nitinol. For some applications, anchor-loop wire loop 50 is fabricated by shaping a wire. For other applications, anchor-loop wire loop 50 is fabricated by wire coiling featuring fixed or variable characteristics along the loop length: the variable characteristics may include one or more of outside diameter, pitch spacing, and stiffness. For other applications, anchor-loop wire loop 50 is fabricated by laser-cutting and shaping a tube or a flat shape sheet of metal, such as a shape memory alloy, e.g., Nitinol.

Anchor-loop wire loop 50 is configured to be positioned in a ventricle 23, extending between a ventricular apical area 24 (at the bottom of ventricle 23) and a subannular surface 25 of a target native leaflet 26 of native valve 22. Anchor-loop wire loop 50 is configured to remain anchored in position against surrounding anatomy, including subannular surface 25, a ventricular wall 27, and ventricular apical area 24, such as shown in FIG. 2. In other words, anchor-loop wire loop 50 is configured to be secured underneath and behind target native leaflet 26, in contact with subannular surface 25, to be seated apically, and to be stabilized by ventricular wall 27. Typically, anchor-loop wire loop 50 is configured to pass behind or across ventricular papillary muscles 46 of ventricular apical area 24. Optionally, the surrounding anatomy against which anchor-loop wire loop 50 is anchored further includes one or more of the following: a moderator band, one or more chordae tendineae, and one or more papillary muscles on the opposite side of ventricle 23.

For some applications, coaptation-assist device 20 does not comprise any elements that are configured to penetrate (e.g., pierce) tissue. For other applications, coaptation-assist device 20 comprises at least one element that is configured to penetrate tissue, such as described hereinbelow with reference to FIGS. 21 and 22.

Neo-leaflet 32 is configured to at least partially replace function of target native leaflet 26 by providing a surface of coaptation 34 for one or more opposing native leaflets 28 that oppose target native leaflet 26, when anchor-loop wire loop 50 is positioned in ventricle 23, such as shown in FIG. 2. Neo-leaflet 32 is typically configured to cover at least a portion of target native leaflet 26.

For some applications, coaptation surface 34 has an area of at least 2 cm2 (e.g., at least 10 $cm^2$), no more than 20 cm2 (e.g., no more than 15 cm2), and/or between 2 cm (e.g., 10 $cm^2$) and 20 cm2 (e.g., 15 cm2). The other coaptation surfaces described hereinbelow may also have these areas.

For some applications, neo-leaflet 32 comprises a neo-leaflet wire loop 36 that defines at least a portion of a border of the neo-leaflet, and a neo-leaflet cover 38 attached to neo-leaflet wire loop 36. Typically, neo-leaflet cover 38 provides the above-mentioned coaptation surface 34. For some applications, neo-leaflet cover 38 comprises one or more biocompatible thin sheets of material, which may comprise a synthetic material or a biological tissue material, such as, for example, a fabric comprising of a polymer or biomaterial (e.g., polyethylene terephthalate (PET), expanded polytetrafluoroethylene (ePTFE), silicone, urethane, or pericardium). Neo-leaflet wire loop 36 may be shaped as a closed loop or an open loop, which is open on a proximal side in the direction of loop-shaped ventricular anchor 30 and native-leaflet grasper 40, if provided. Neo-leaflet wire loop 36 comprises metal or another semi-rigid material. The material of neo-leaflet wire loop 36 is either self-expanding or mechanically expandable. For example, neo-leaflet wire loop 36 may comprise a shape-memory alloy, such as Nitinol. For some applications, neo-leaflet wire loop 36 is fabricated by shaping one or more wires. For other applications, neo-leaflet wire loop 36 is fabricated by wire coiling featuring fixed or variable characteristics along the loop length, including one or more of outside diameter, pitch spacing, and stiffness. For some applications, the wire of neo-leaflet wire loop 36 is circular in cross-section: alternatively, the wire has another cross-sectional shape, such as elliptical, rectangular, or generally flat. For still other applications, neo-leaflet wire loop 36 is fabricated by laser-cutting and shaping a tube or a flat shape sheet of metal, such as a shape memory alloy, e.g., Nitinol.

For some applications, neo-leaflet 32 has an intrinsic stiffness provided by the material of neo-leaflet wire loop 36 and/or neo-leaflet cover 38. Alternatively or additionally, neo-leaflet 32 comprises one or more stiffening elements within neo-leaflet cover 38 of the neo-leaflet to prevent the neo-leaflet from prolapsing in the atrial chamber as a result of an increase of backflow pressure over the neo-leaflet's ventricular surface during the cardiac cycle.

Typically, anchor-loop wire loop 50 is configured to remain anchored in position by force (typically radially-outwardly-directed force) applied by anchor-loop wire loop 50 to the surrounding anatomy, and/or by friction between anchor-loop wire loop 50 and the surrounding anatomy. For some applications, anchor-loop wire loop 50 comprises a self-expandable material, such as a shape-memory alloy (e.g., Nitinol) that causes the anchor-loop wire loop 50 to expand radially outwardly so as to apply the force. For these applications, anchor-loop wire loop 50 typically is configured to have a shape in its resting (relaxed) state that is larger than the surrounding anatomy, such that the surrounding anatomy limits expansion of anchor-loop wire loop 50 and anchor-loop wire loop 50 applies a force to the surrounding anatomy (and vice versa). In addition, the narrowing of ventricular wall 27 in a subannular-to-apical direction compresses anchor-loop wire loop 50, creating a counter-radial force, and directing anchor-loop wire loop 50 to stabilize itself at the sub-leaflet ventricular hinge level (i.e., at the level of subannular surface 25) (where, optionally, loop-shaped ventricular anchor 30 (such as anchor-loop wire loop 50) also functions to grasp target native leaflet 26 in some configurations, optionally in conjunction with native-leaflet grasper 40, described hereinbelow with reference to FIGS. 1A-E and 2).

Typically, loop-shaped ventricular anchor 30 is configured to be atraumatic so as not to penetrate (e.g., pierce) tissue of the surrounding anatomy. To this end, loop-shaped ventricular anchor 30 typically does not comprise any exposed sharp elements that might penetrate tissue.

As mentioned above, for some applications native valve 22 is the tricuspid valve. For these applications, neo-leaflet 32 is configured to at least partially replace function of target native leaflet 26 by providing coaptation surface 34 for one or more opposing native leaflets 28 of the tricuspid valve, when anchor-loop wire loop 50 is positioned in ventricle 23. For some of these applications, target native leaflet 26 is a native septal leaflet of the tricuspid valve, ventricular wall 27 is a ventricular septal wall, and neo-leaflet 32 is configured to at least partially replace function of the septal leaflet by providing coaptation surface 34 for one or more of the opposing native posterior and anterior leaflets of the tricuspid valve, when anchor-loop wire loop 50 is positioned in ventricle 23 and remains anchored in position against the surrounding anatomy, including subannular surface 25, ventricular septal wall 27, and ventricular apical area 24, i.e., generally in a sub-septal ventricular area. Although in the cross-sectional view of the heart in FIG. 2, the only opposing native leaflet 28 that is shown is the posterior native leaflet, the opposing anterior native leaflet also coapts with coaptation surface 34 when it partially replaces the septal leaflet.

Figure 23:
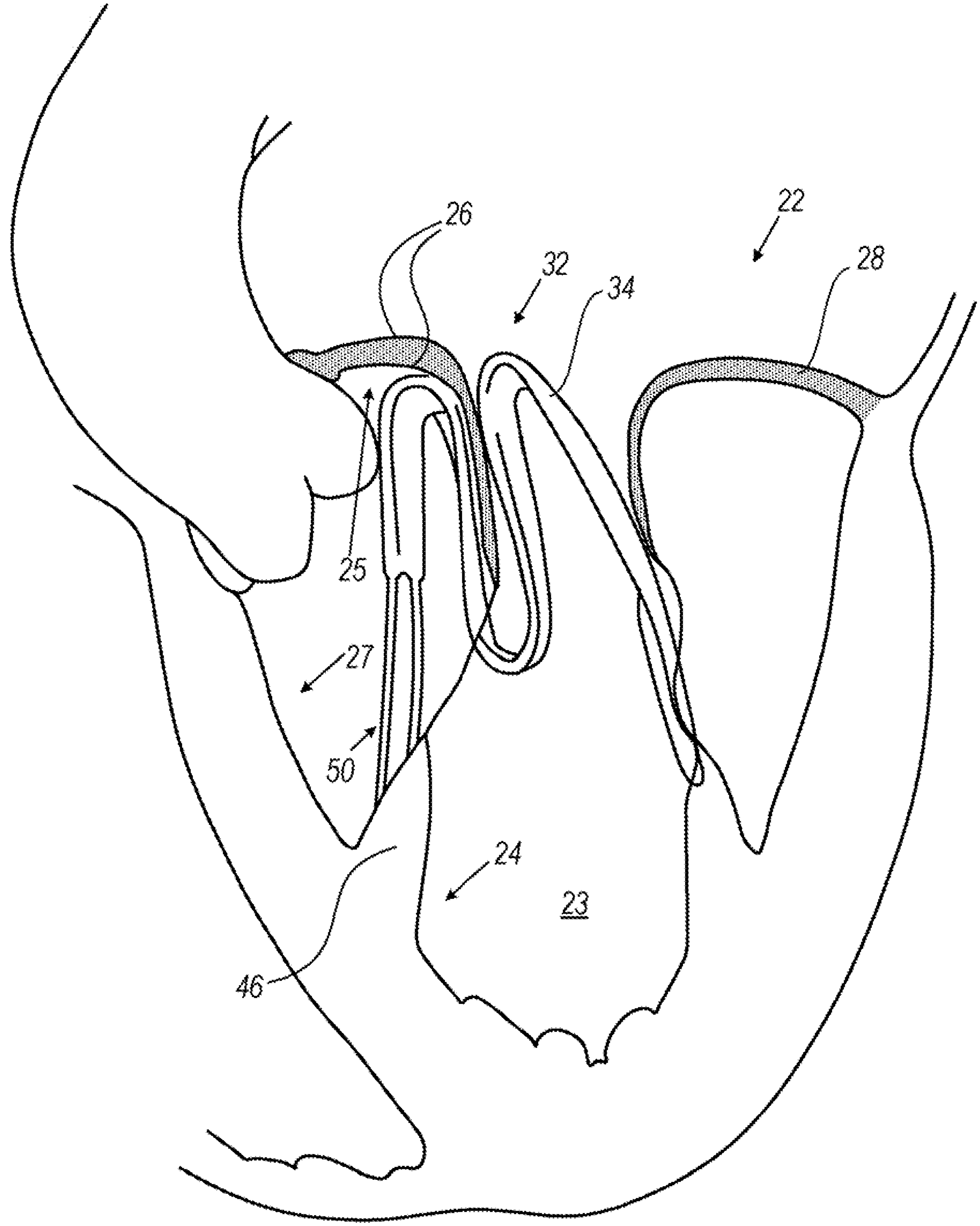
FIG. 23 is a schematic illustration of a coaptation-assist device implanted in a native mitral valve, in accordance with an application of the present invention.

For other applications (as shown in FIG. 23, described hereinbelow), native valve 22 is a mitral valve, and neo-leaflet 32 is configured to at least partially replace function of target native leaflet 26 (either a native posterior leaflet or a native anterior leaflet) by providing a coaptation surface 34 for the opposing native leaflet of the mitral valve, when anchor-loop wire loop 50 is positioned in the ventricle. For some of these applications, target native leaflet 26 is the native anterior leaflet of the mitral valve, ventricular wall 27 is a ventricular septal wall, and neo-leaflet 32 is configured to at least partially replace function of the native anterior leaflet by providing coaptation surface 34 for the opposing native posterior leaflet of the mitral valve, when anchor-loop wire loop 50 is positioned in ventricle 23 and remains anchored in position against the surrounding anatomy, including subannular surface 25, ventricular septal wall 27, and ventricular apical area 24.

For some applications, anchor-loop wire loop 50 is configured to remain anchored in position against subannular surface 25, ventricular septal wall 27, and one or more ventricular papillary muscles 46 of ventricular apical area 24, when anchor-loop wire loop 50 is positioned in ventricle 23, such as shown in FIG. 2.

For some applications, anchor-loop wire loop 50 is shaped as a closed loop that defines an entirety of the border of loop-shaped ventricular anchor 30, such as shown in FIGS. 1A-E. For other applications, anchor-loop wire loop 50 is shaped as an open loop, which is shaped so as to have a proximal opening facing neo-leaflet 32 and native-leaflet grasper 40, if provided, such as shown, for example, in FIGS. 5A, 10A-F, 11A-D, 12A-E, 13A-E, and 16A-F. For these latter applications, a proximal side of loop-shaped ventricular anchor 30 is defined by another element of coaptation-assist device 20, such as grasper covers 144A, 144B, 144C, and 444, respectively, of native-leaflet grasper 40, as shown in FIGS. 10A-C, 10D-F, 11A-D, and 16A-F, or neo-leaflet covers 338A and 338B of neo-leaflets 332A and 332B, respectively, as shown in FIGS. 12A-E, and 13A-E.

For some applications, anchor-loop wire loop 50 has one or more of the following dimensions:

- an enclosed (surrounded) area of at least 2 cm2, no more than 60 cm2, and/or between 2 and 60 cm2,
- a perimeter of at least 4 cm, no more than 15 cm, and/or between 4 and 15 cm,
- a length of at least 2 cm, no more than 12 cm, and/or between 2 and 12 cm, and/or
- a width of at least 1 cm, no more than 12 cm, and/or between 1 and 12 cm.

Anchor-loop wire loop 50 may define a plane or a curved surface.

For some applications, anchor-loop wire loop 50, when unconstrained (by application of any external forces, including by the anatomy or the delivery system), is curved along at least 50% (e.g., at least 75%, such as at least 90%, e.g., 100%) of a length of anchor-loop wire loop 50, the length measured around anchor-loop wire loop 50.

Alternatively or additionally, for some applications, anchor-loop wire loop 50 is shaped as at least 75% of an oval, e.g., as at least 90%, such as 100%, of an oval, when unconstrained (by application of any external forces, including by the anatomy or the delivery system).

Reference is now made to FIGS. 3A-K, which are highly schematic illustrations of loop-shaped ventricular anchors 30A-K, respectively, in accordance with respective applications of the present invention. In these figures, the proximal ends of the loop-shaped ventricular anchors are shown above the distal ends on the sheet (the proximal ends are the ends closer to the neo-leaflet).

Figure 3A:
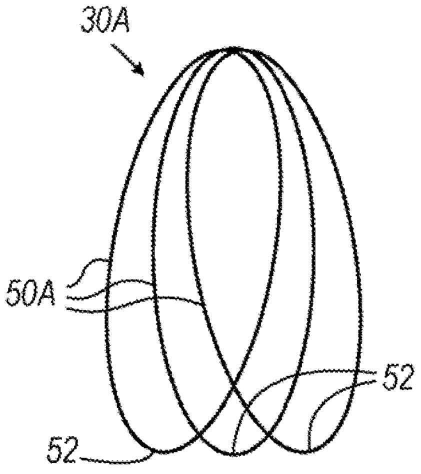

Loop-shaped ventricular anchor 30A of FIG. 3A comprises a plurality of linked anchor-loop wire loops 50A, such as three anchor-loop wire loops 50A, which define a respectively plurality of loop-lobes 52 that are configured to be positioned in ventricular apical area 24.

Figure 3B:
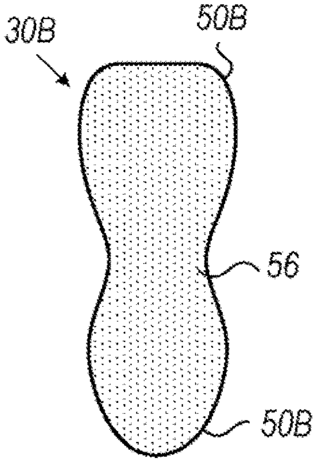
Figure 3C:
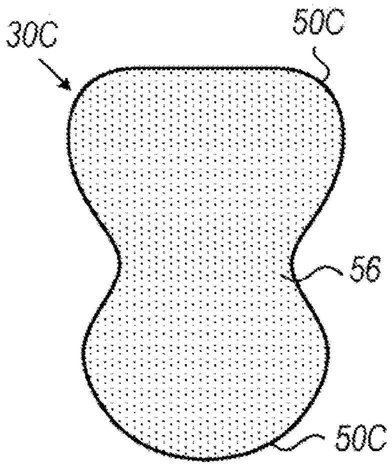

Loop-shaped ventricular anchor 30B and 30C of FIGS. 3B and 3C, respectively, comprise anchor-loop wire loops 50B and 50C, respectively. Anchor-loop wire loop 50B has a near-hourglass shape, and anchor-loop wire loop 50B has a full-hourglass shape. Loop-shaped ventricular anchor 30C of FIG. 3C comprises an anchor-loop wire loop 50C that is shaped as a figure-eight.

Figure 3D:
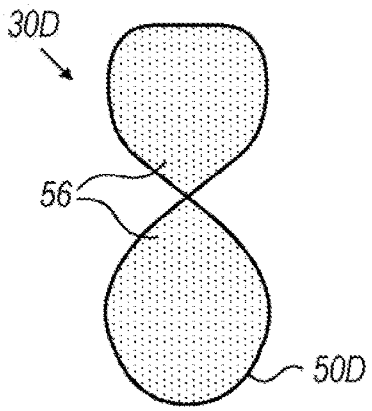

Loop-shaped ventricular anchor 30D of FIG. 3D comprises an anchor-loop wire loop 50D that is twisted so as to define an hourglass shape.

Figure 3E:
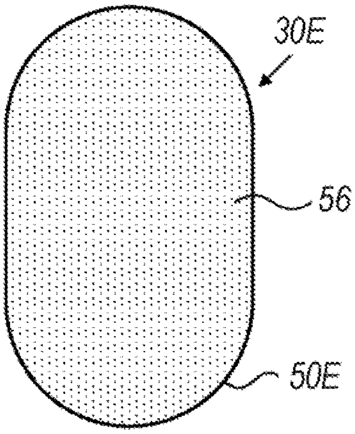

Loop-shaped ventricular anchor 30E of FIG. 3E comprises an anchor-loop wire loop 50E that has a stadium shape. As used in the present application, including in the claims and Inventive concepts, a stadium shape is a two-dimensional geometric shape constructed of a rectangle with semicircles at a pair of opposite sides. The same shape is known also as a discorectangle, obround, or sausage body.

Loop-shaped ventricular anchor 30F of FIG. 3F comprises an anchor-loop wire loop 50F having wavy lateral edges.

Loop-shaped ventricular anchor 30G of FIG. 3G comprises an anchor-loop wire loop 50G shaped as to define a plurality of lobes (e.g., three, as shown).

Loop-shaped ventricular anchor 30H of FIG. 3H comprises a plurality (e.g., at least 5, such as at least 10) braided anchor-loop wire loops 50H that are shaped so as to define a loop-shape space (it is the braid itself that is formed so that its edges define a loop).

Loop-shaped ventricular anchor 301 of FIG. 3I has a width greater than a height.

Loop-shaped ventricular anchor 30J of FIG. 3J comprises one or more barbs 301J.

Loop-shaped ventricular anchor 30K of FIG. 3K comprises a tightly-coiled wire 301K.

For some applications, any of the loop-shaped ventricular anchors described herein, including with reference to FIGS. 1A-E, FIGS. 3A-G, and FIGS. 3I-K, may further comprise an anchor-loop cover attached to the anchor-loop wire loop. For some of these applications, the anchor-loop cover comprises one or more biocompatible thin sheets of material 56 that extend across and partially or entirely occupy a space at least partially surrounded by the anchor-loop wire loop. Typically, the one or more biocompatible thin sheets of material 56 are soft and atraumatic. For some applications, the one or more biocompatible thin sheets of material 56 are configured to promote endothelization. The one or more biocompatible thin sheets of material 56 may comprise a synthetic material or a biological tissue material, such as, for example, a fabric comprising of a polymer or biomaterial (e.g., polyethylene terephthalate (PET), expanded polytetrafluoroethylene (ePTFE), silicone, urethane, or pericardium). For still other applications, the anchor-loop cover comprises a coating on the anchor-loop wire loop, e.g., tissue, polyethylene terephthalate (PET), expanded polytetrafluoroethylene (ePTFE), or a foam. Alternatively or additionally, the anchor-loop wire loop surface may be mechanically or chemically treated, e.g., by electropolishing or sandblasting, or provided with barbs (such as barbs 301J, shown in FIG. 3J), in order to create friction to help maintain the loop in place.

For other applications, the anchor-loop cover comprises braided wires, which optionally are additionally covered by one or more biocompatible thin sheets of material, such as described immediately above.

Reference is again made to FIGS. 1A-E and 2. For some applications, coaptation-assist device 20 further comprises a native-leaflet grasper 40, which is configured to grasp atrial and ventricular surfaces of target native leaflet 26, in order to support and/or stabilize neo-leaflet 32, and to orient neo-leaflet 32 with respect to native valve 22. For example, native-leaflet grasper 40 may help prevent neo-leaflet 32 from tilting toward one of the native commissures, and/or may help orient neo-leaflet 32 at a desired angle with respect to the native valvular plane. Alternatively, the coaptation-assist devices described herein do not comprise a native-leaflet grasper, such as, for example, described hereinbelow with reference to FIGS. 21-22, For some applications, neo-leaflet 32 is coupled to loop-shaped ventricular anchor 30 via native-leaflet grasper 40, such as shown in FIGS. 1A-E and 2. For some of these applications, coaptation-assist device 20 comprises a wire loop that is shaped so as to at least partially define neo-leaflet 32 and native-leaflet grasper 40, such as shown.

For some applications, coaptation-assist device 20 comprises a coaptation-assist-device wire loop that is shaped so as to at least partially define neo-leaflet 32, native-leaflet grasper 40, and anchor-loop wire loop 50, such as shown. For some of these applications, the wire loop is shaped so as to at least partially define native-leaflet grasper 40 along the wire loop between neo-leaflet 32 and anchor-loop wire loop 50, such as shown.

For some applications, native-leaflet grasper 40 is shaped so as to define first and second portions 42A and 42B that are configured to fold toward each other so as to grasp the atrial and the ventricular surfaces, respectively, of target native leaflet 26 by sandwiching at least a portion of the atrial and the ventricular surfaces of target native leaflet 26 between the first and the second portions of native-leaflet grasper 40.

For some applications, coaptation-assist device is configured such that:

- first portion 42A of native-leaflet grasper 40 is pivotably coupled to loop-shaped ventricular anchor 30,
- first portion 42A of native-leaflet grasper 40 is pivotably coupled to second portion 42B of native-leaflet grasper 40, and/or
- second portion 42B of native-leaflet grasper 40 is pivotably coupled to neo-leaflet 32.

For some applications, native-leaflet grasper 40 comprises one or more grasper covers 44, which collectively comprise one or more biocompatible thin sheets of material (optionally, the same one or more sheets of material (e.g., the same exactly one sheet of material) define both neo-leaflet cover 38, described above, and the one or more grasper covers 44: alternatively, separate sheets of material define neo-leaflet cover 38 and the one or more grasper covers 44). Typically, at least one of the one or more grasper covers 44 pushes against the ventricular and/or atrial surfaces of target native leaflet 26 to prevent blood flow between the target native leaflet and the coaptation-assist device. For some of these applications, the one or more grasper covers 44 extend across and partially or entirely occupy a space at least partially surrounded by a frame 45 of native-leaflet grasper 40, which may comprise one or more wires, which may be part of the wire loop described above. For some applications, the one or more grasper covers 44 extend across and partially or entirely cover a space at least partially surrounded by the portion of frame 45 that defines first portion 42A of native-leaflet grasper 40 (which is configured to grasp the atrial surface of target native leaflet 26), and the one or more grasper covers 44 do not at least partially cover a space at least partially surrounded by the portion of frame 45 that defines second portion 42B of native-leaflet grasper 40 (which is configured to grasp the ventricular surface of target native leaflet 26).

Typically, the one or more biocompatible thin sheets of material are soft and atraumatic. The one or more biocompatible thin sheets of material may comprise a synthetic material or a biological tissue material, such as, for example, a fabric comprising of a polymer or biomaterial (e.g., polyethylene terephthalate (PET), expanded polytetrafluoroethylene (ePTFE), silicone, urethane, or pericardium).

For some of these applications, native-leaflet grasper 40 is shaped so as to further define a third portion 42C at a fold between first and second portions 42A and 42B of native-leaflet grasper 40, and third portion 42C is configured to extend around the free edge of target native leaflet 26 when first and second portions 42A and 42B sandwich the at least a portion of the atrial and the ventricular surfaces of target native leaflet 26.

For some applications, neo-leaflet 32 is configured to surround target native leaflet 26 completely, including the lateral sides of the target native leaflet, enclosing the target native leaflet from the ventricular native leaflet hinge to the atrial hinge, in the proximity of the valvular annulus, and from commissure to commissure. For other applications, neo-leaflet 32 is configured to surround the target native leaflet 26 partially, covering and enclosing part of the target native leaflet, typically at least the free edge of the target native leaflet.

Figure 1A:
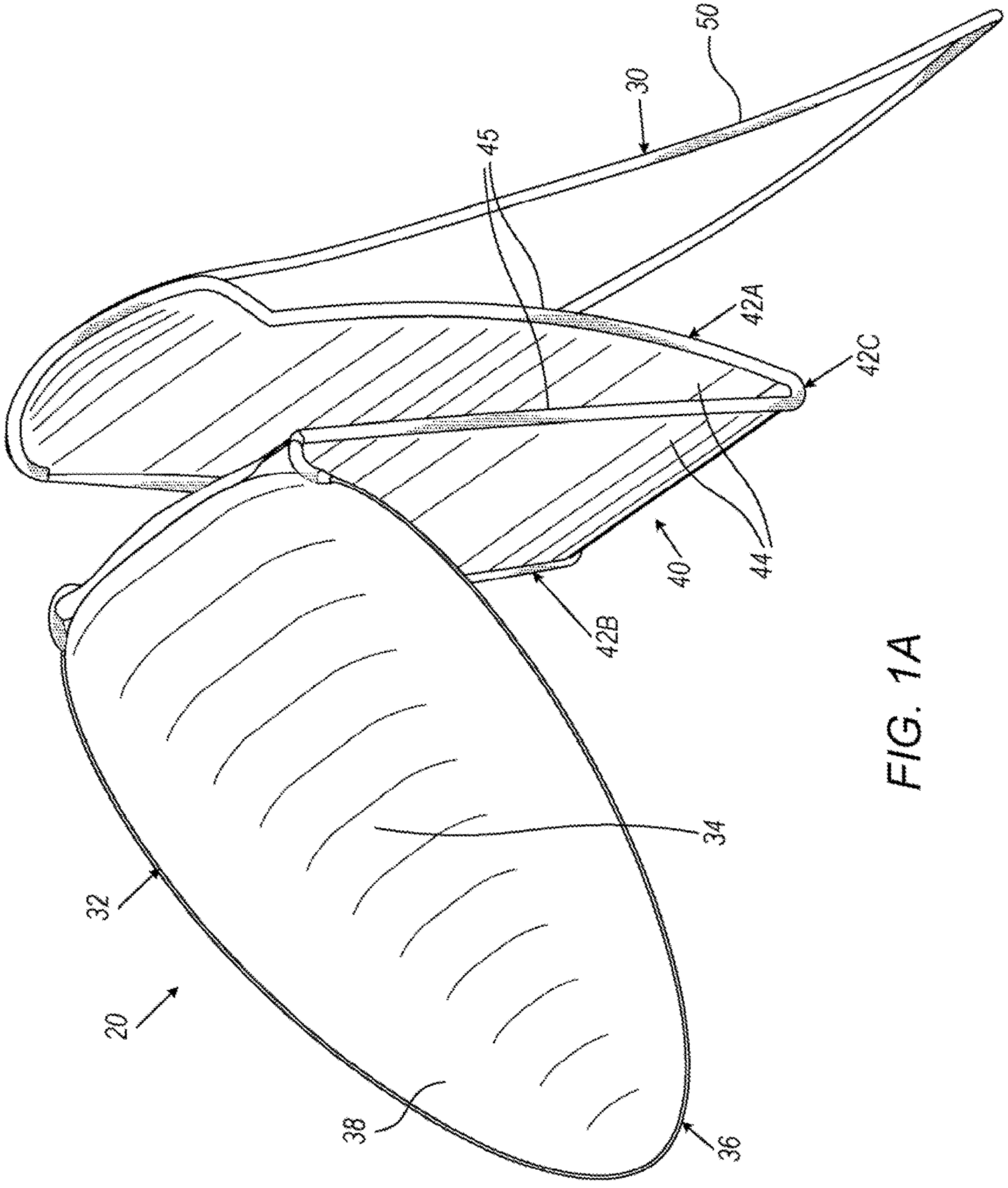
FIGS. 1A-E are schematic illustrations of a coaptation-assist device for treating a native valve of a subject, in accordance with an application of the present invention.
Figure 1B:
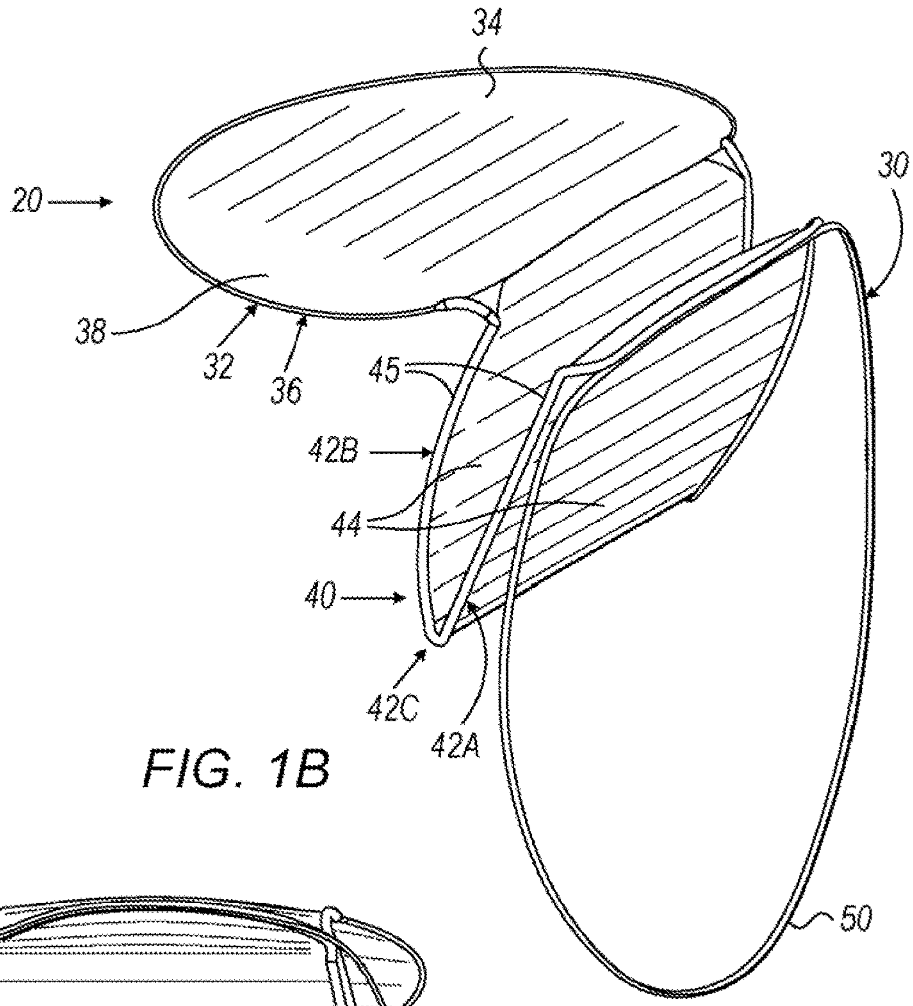
Figure 1C:
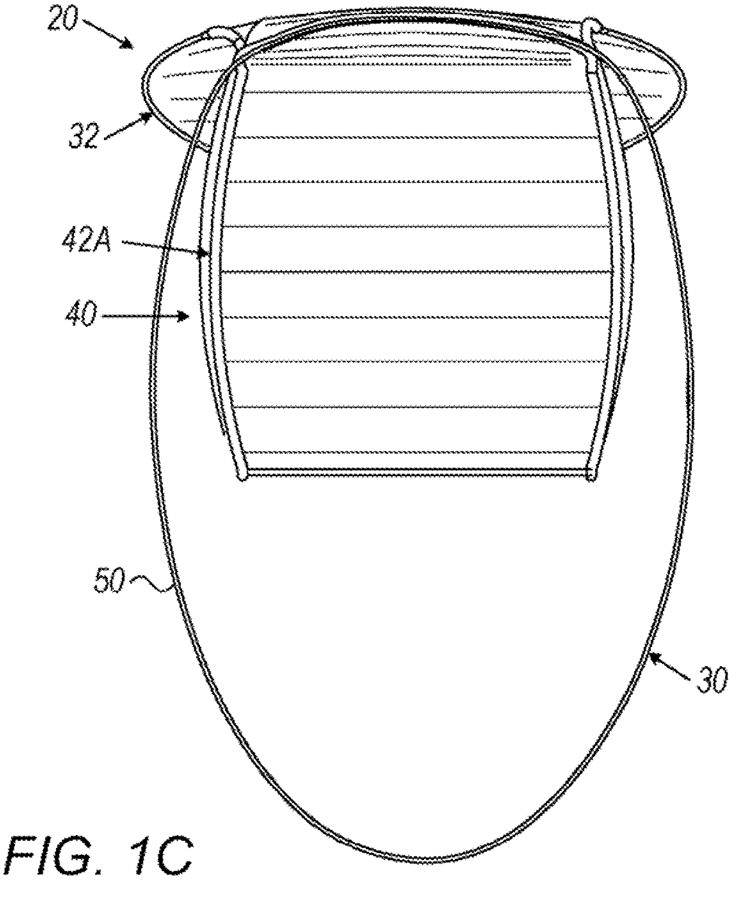
Figure 1D:
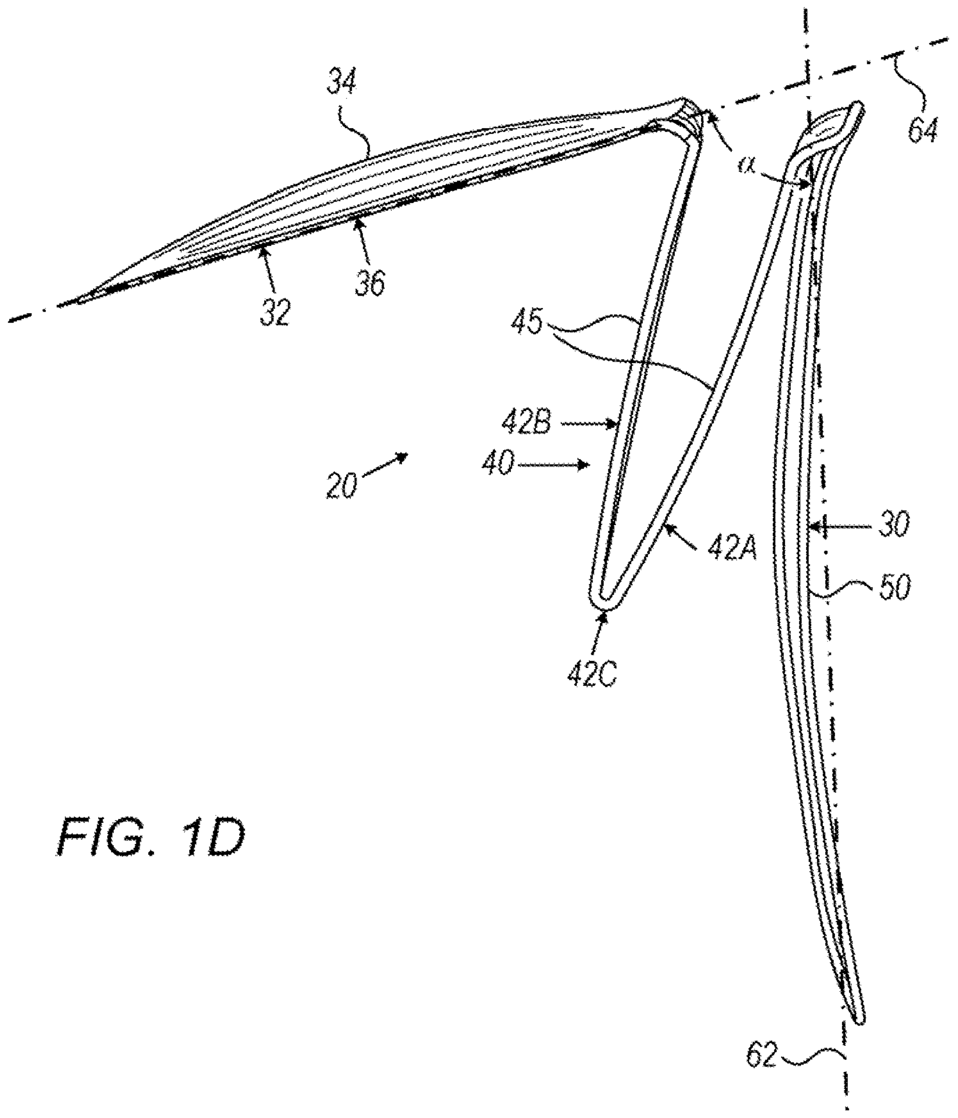

Reference is made to FIG. 1D. For some applications, coaptation-assist device 20 is configured such that when unconstrained (by application of any external forces, including by the anatomy or the delivery system), an angle $\alpha$ (alpha) is defined between (a) an anchor-loop best-fit plane 62 defined by anchor-loop wire loop 50 and (b) a neo-leaflet best-fit plane 64 defined by neo-leaflet wire loop 36. Typically, coaptation-assist device 20 is configured to automatically assume this angle: for example, elements of the devices may comprise a shape-memory alloy, such as Nitinol, which is configured to cause the device to assume this angle when in a resting, relaxed state, e.g., at 37 degrees Celsius (body temperature). As used in the present application, including in the claims and Inventive concepts, a "best-fit plane" defined by a wire loop is the plane that most closely matches the shape of the wire loop, i.e., the plane that results in the minimal sum of squares of distances between the plane and the wire loop. Alternatively, neo-leaflet best-fit plane 64 defined by neo-leaflet wire loop 36 is defined by coaptation surface 34. (In coaptation-assist devices 220A and 220B, described hereinbelow with reference to FIGS. 8A-B, anchor-loop best-fit plane 62 may instead be defined by a border of loop-shaped ventricular anchors 230A and 230B, respectively, and neo-leaflet best-fit plane 64 may instead be defined by a border of neo-leaflets 232A and 232B, respectively.)

For some applications, such as shown in FIG. 1D, the angle $\alpha$ (alpha) is at least 60 degrees (e.g., at least 80 degrees), no more than 100 degrees (e.g., no more than 90 degrees), and/or between 60 degrees (e.g., 80 degrees) and 100 degrees (e.g., 90 degrees). This range of angles may be appropriate as described hereinbelow with reference to FIGS. 12D and 14. For other applications, the angle $\alpha$ (alpha) is at least 15 degrees (e.g., at least 35 degrees), no more than 50 degrees (e.g., no more than 45 degrees), and/or between 15 degrees (e.g., 35 degrees) and 50 degrees (e.g., 45 degrees). This range of angles may be appropriate as described hereinbelow with reference to FIGS. 13C and 15A.

For some applications, all of the coaptation-assist devices may be configured to assume one of the above-mentioned ranges of angles.

Figure 1E:
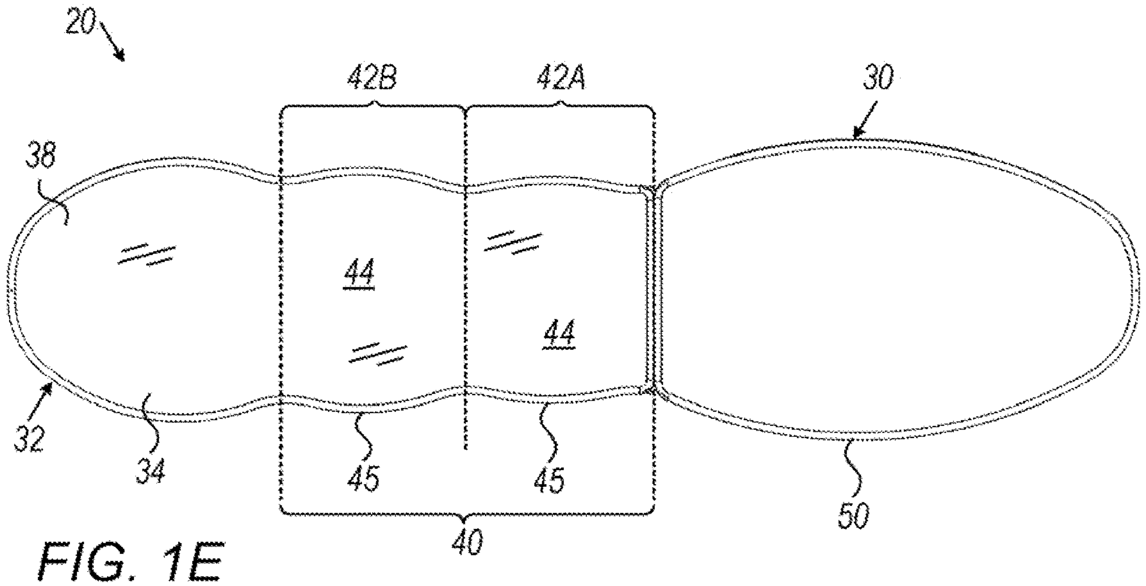

Reference is made to FIG. 1E. For some applications, coaptation-assist device 20 can be extended and flattened into the elongate flattened configuration shown in FIG. 1E. After being flattened, coaptation-assist device 20 can be crimped and then loaded into delivery tube 304, for delivery as described hereinbelow with reference to FIG. 9A. Coaptation-assist device 20 typically has a shape memory so that it automatically resumes its initial resting state incrementally as it is exposed and deployed from delivery tube 304, as described hereinbelow with reference to FIGS. 9A-H.

Reference is still made to FIGS. 1A-E and 2. For some applications, neo-leaflet 32 is configured such that coaptation surface 34 is generally static throughout a cardiac cycle of the subject upon implantation of coaptation-assist device 20 in a heart of the subject. In these applications, coaptation is provided by motion of the one or more opposing native leaflets 28 against the generally static coaptation surface 34 provided by neo-leaflet 32. For example, to achieve this general stasis, neo-leaflet wire loop 36 and/or neo-leaflet cover 38 of neo-leaflet 32 may be relatively stiff, and/or neo-leaflet 32 may comprise one or more stiffening elements within neo-leaflet cover 38, as described above.

For other applications, neo-leaflet 32 is configured such that coaptation surface 34 moves toward and away from the one or more opposing native leaflets 28 during a cardiac cycle of the subject upon implantation of coaptation-assist device 20 in a heart of the subject. In other words, neo-leaflet 32 is configured such that coaptation surface 34 is dynamic throughout the cardiac cycle. In these applications, coaptation is provided by motion of coaptation surface 34 provided by neo-leaflet 32 and the one or more opposing native leaflets 28. For example, to allow this motion of coaptation surface 34, neo-leaflet wire loop 36 and/or neo-leaflet cover 38 of neo-leaflet 32 may be flexible enough to allow it to move during the cardiac cycle. For example, as shown in FIGS. 1A-E, a diameter of wire (i.e., a wire gauge) of neo-leaflet wire loop 36 may be less than a diameter of wire of anchor-loop wire loop 50 of loop-shaped ventricular anchor 30 and/or than diameters of other wires of coaptation-assist device 20, such as of wire of native-leaflet grasper 40 if provided. Alternatively, the neo-leaflet may not comprise a wire loop that defines at least the portion of the border, such as described hereinbelow with reference to FIG. 7. Further alternatively, the neo-leaflet cover may have a surface area that is greater than an area defined and surrounded by the neo-leaflet wire loop, so as to create a flexible parachute-like coaptation surface that inflates and relaxes during the cardiac cycle, such as described hereinbelow with reference to FIGS. 5A-B and 6A-C. The flexible parachute-like coaptation surface is configured to inflate and relax along the blood flow and pressure variation against the ventricular surface of coaptation during the cardiac cycle, so that both the blood flow and blood pressure increase and are directed against the ventricular surface of the neo-leaflet during the systolic phase of the cardiac cycle. As a result, the neo-leaflet inflates and dynamically increases the surface of coaptation for the one or more opposing native leaflets 28. The blood flow and blood pressure action against the neo-leaflet ventricular surface decrease during the diastolic phase, causing the neo-leaflet to relax and deflate, leaving the neo-leaflet structure in a resting shape during the diastolic phase, so as not to 30) occlude the orifice area blood passage from the atrial to the ventricular chamber. In other words, during diastole, the neo-leaflet deflates and relaxes, allowing passage of blood from the atrium to the ventricle.

Figure 4A:
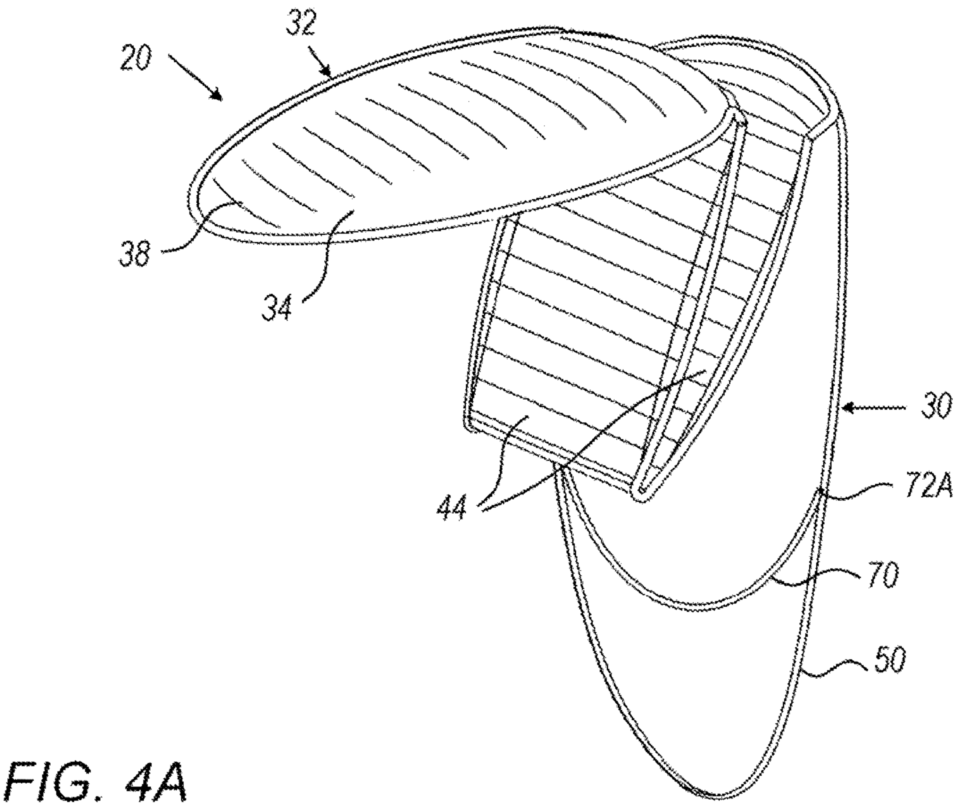
FIGS. 4A-B are schematic illustrations of another configuration of the coaptation-assist device of FIGS. 1A-E and 2, in accordance with an application of the present invention.
Figure 4B:
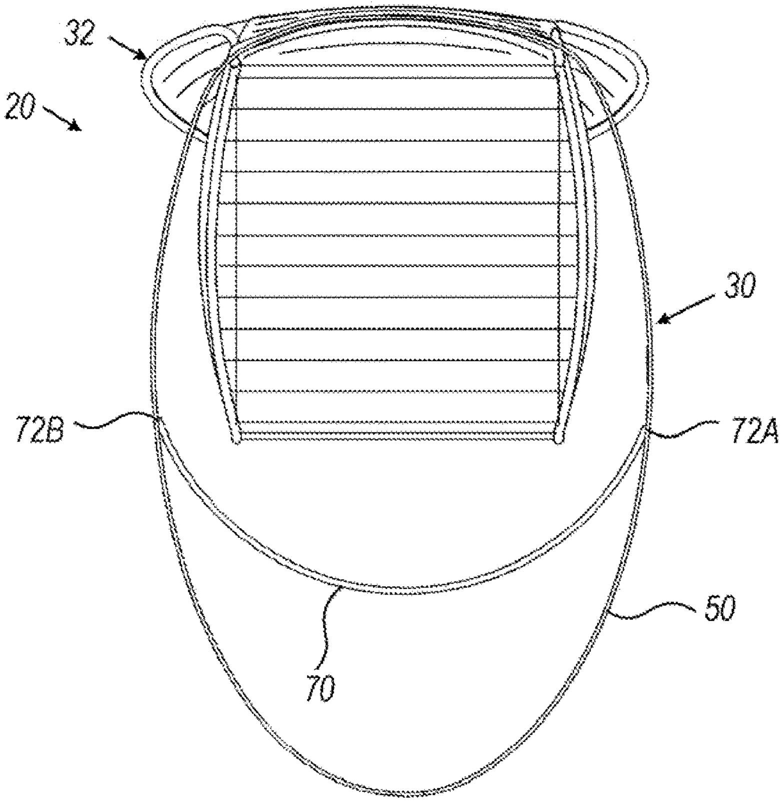

Reference is now made to FIGS. 4A-B, which are schematic illustrations of another configuration of coaptation-assist device 20, in accordance with an application of the present invention. In this configuration, loop-shaped ventricular anchor 30 comprises at least one supporting wire 70, which is coupled to anchor-loop wire loop 50 at two sites 72A and 72B on anchor-loop wire loop 50. For example, two sites 72A and 72B may be on opposite sides of anchor-loop wire loop 50, such as shown, and/or on long sides of anchor-loop wire loop 50, also as shown.

Figure 5A:
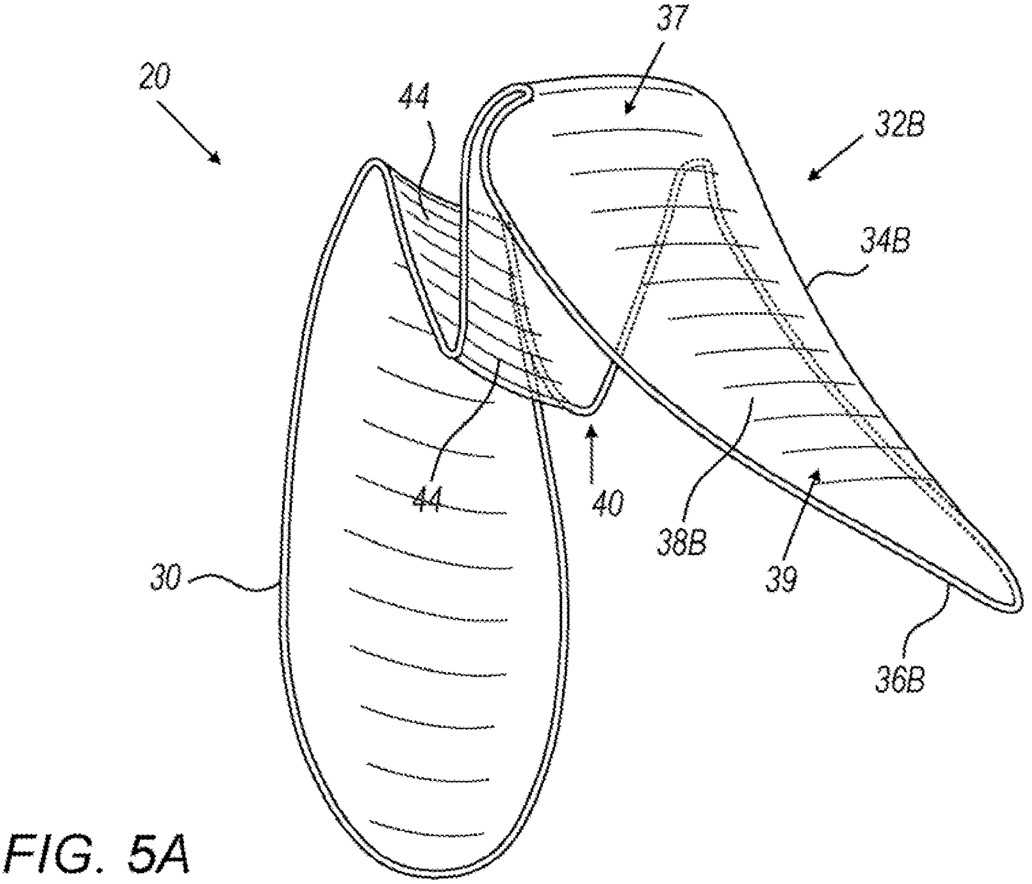
FIGS. 5A-B are schematic illustrations of yet another configuration of the coaptation-assist device of FIGS. 1A-E and 2, in accordance with an application of the present invention.
Figure 5B:
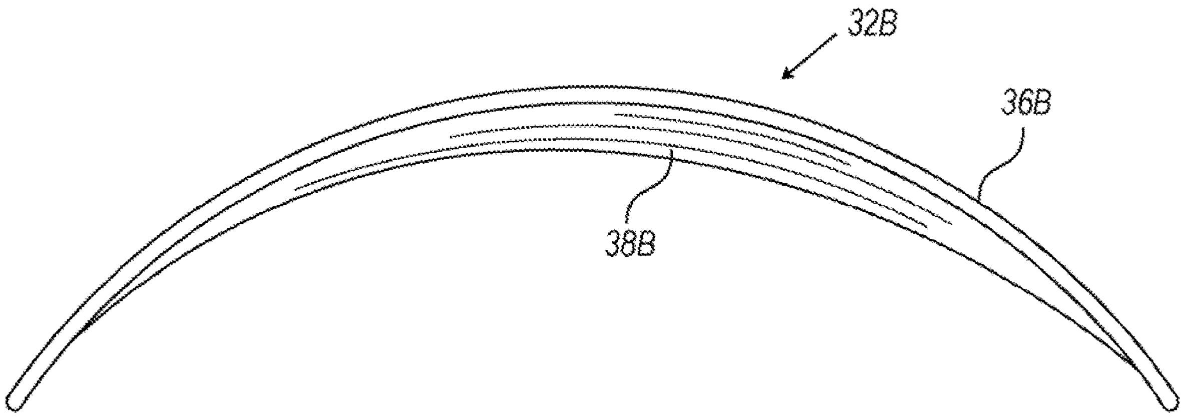

Reference is now made to FIGS. 5A-B, which are schematic illustrations of yet another configuration of coaptation-assist device 20, in accordance with an application of the present invention. In this configuration, coaptation-assist device 20 comprises a neo-leaflet 32B, which, other than as described below, is identical to neo-leaflet 32 described hereinabove and may implement any of the features thereof, mutatis mutandis. Neo-leaflet 32B comprises a neo-leaflet open wire loop 36B and a neo-leaflet cover 38B attached to neo-leaflet open wire loop 36B. Neo-leaflet open wire loop 36B is open on a distal side 37 in the direction of loop-shaped ventricular anchor 30 and native-leaflet grasper 40, if provided. Neo-leaflet cover 38B has a surface area that is greater than an area defined by and surrounded on approximately three sides by neo-leaflet open wire loop 36B. As a result, in configurations in which neo-leaflet cover 38B is flexible, when ventricular surface 39 of neo-leaflet cover 38B is exposed to increased blood pressure during the cardiac cycle, neo-leaflet cover 38B tents away from neo-leaflet open wire loop 36B, optionally to a greater extent more distally along neo-leaflet cover 38B, providing a flexible parachute-like coaptation surface 34B that inflates and relaxes during the cardiac cycle. The curvature of coaptation surface 34B toward and on distal side 37 provides increased efficacy in coaptation with the one or more opposing native leaflets 28. Optionally, neo-leaflet cover 38B comprises an elastic material. In other configurations, neo-leaflet cover 38B is not flexible, but instead stiff, such that neo-leaflet cover 38B is configured not to inflate and relax. In these configurations, the curvature the neo-leaflet provides a greater surface of coaptation to the one or more opposing native leaflets 28.

Alternatively, neo-leaflet wire loop 36B is shaped as a neo-leaflet closed wire loop, in which case neo-leaflet cover 38B is typically not attached to the distal side of the neo-leaflet closed wire loop.

Neo-leaflet cover 38B may implement any of the features of neo-leaflet cover 38, described hereinabove, mutatis mutandis.

Figure 6A:
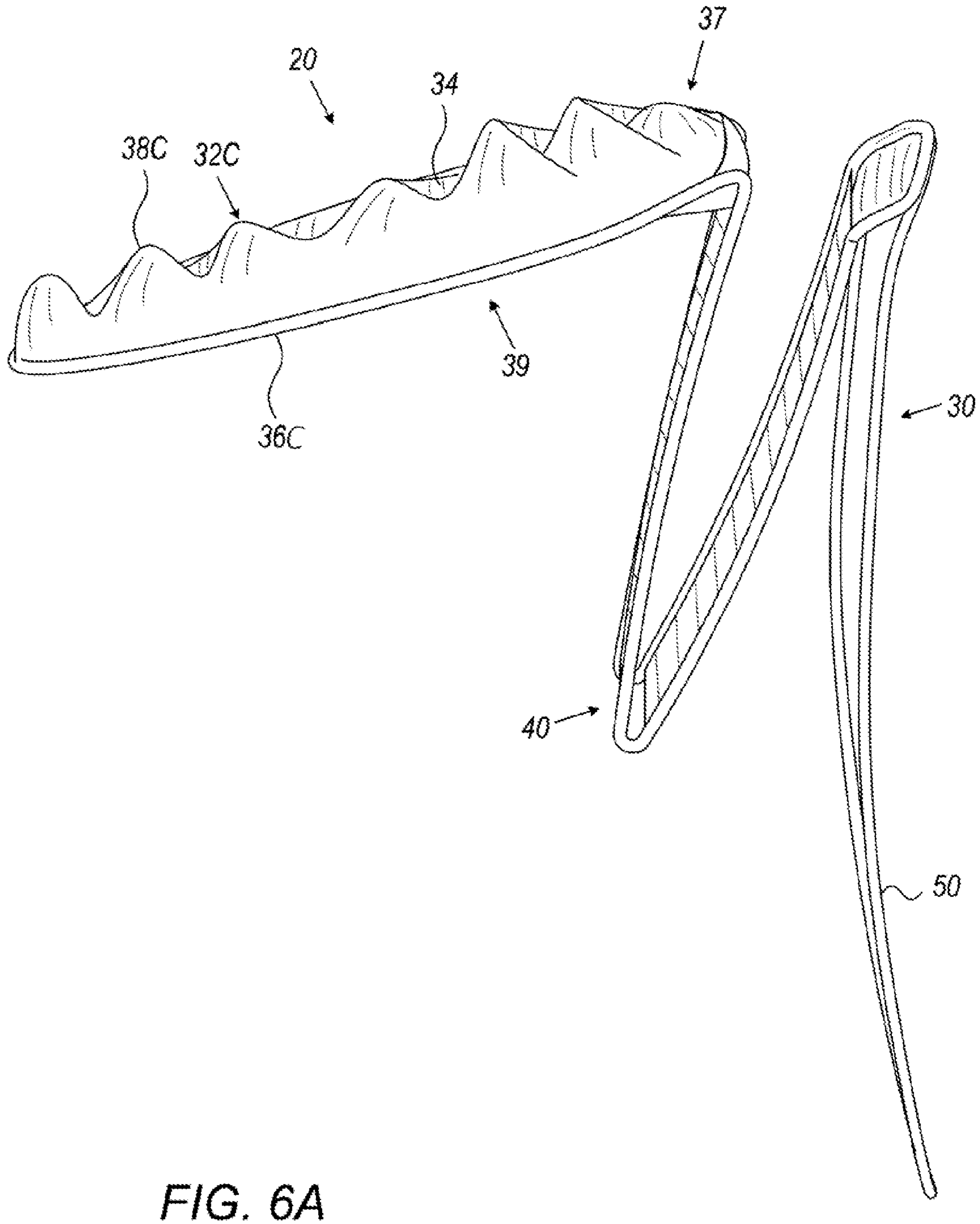
FIGS. 6A-C are schematic illustrations of still another configuration of the coaptation-assist device of FIGS. 1A-E and 2, in accordance with an application of the present invention.
Figure 6C:
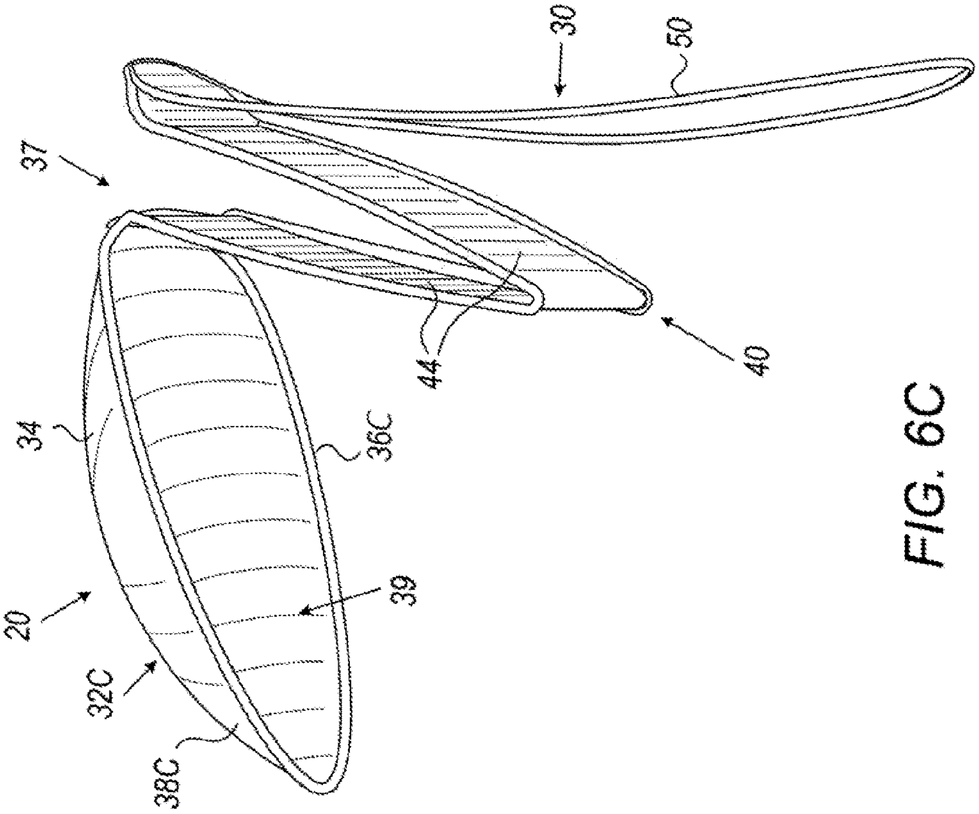
Figure 6B:
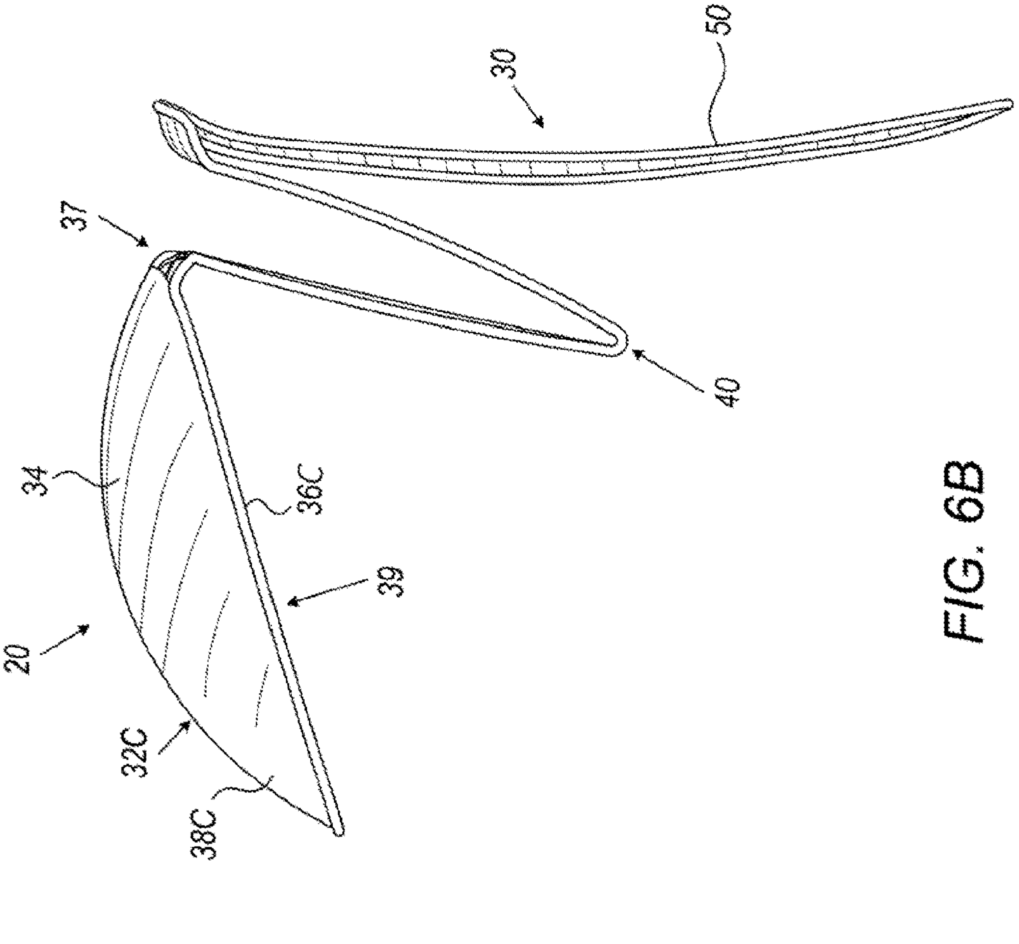

Reference is now made to FIGS. 6A-C, which are schematic illustrations of still another configuration of coaptation-assist device 20, in accordance with an application of the present invention. In this configuration, coaptation-assist device 20 comprises a neo-leaflet 32C, which, other than as described below, is identical to neo-leaflet 32 described hereinabove and may implement any of the features thereof, mutatis mutandis. Neo-leaflet 32C comprises a neo-leaflet wire loop 36C and a neo-leaflet cover 38C attached to neo-leaflet wire loop 36C. For some applications, neo-leaflet wire loop 36C is open on distal side 37 in the direction of loop-shaped ventricular anchor 30 and native-leaflet grasper 40, if provided, as shown, while for other applications neo-leaflet wire loop 36C is shaped as a neo-leaflet closed wire loop. Neo-leaflet cover 38C has a surface area that is greater than an area defined by and surrounded on approximately three sides by neo-leaflet open wire loop 36C. As a result, when a ventricular surface 39 of neo-leaflet cover 38C is exposed to increased blood pressure during the cardiac cycle, neo-leaflet cover 38C tents away from neo-leaflet open wire loop 36C, providing a flexible parachute-like coaptation surface 34C that expands (inflates) and relaxes during the cardiac cycle. Neo-leaflet cover 38C is shown relaxed in FIG. 6A, and expanded (inflated) by blood flow in FIGS. 6B and 6C. Neo-leaflet cover 38C may implement any of the features of neo-leaflet cover 38, described hereinabove, mutatis mutandis. Optionally, neo-leaflet cover 38C comprises an elastic material.

Figure 7:
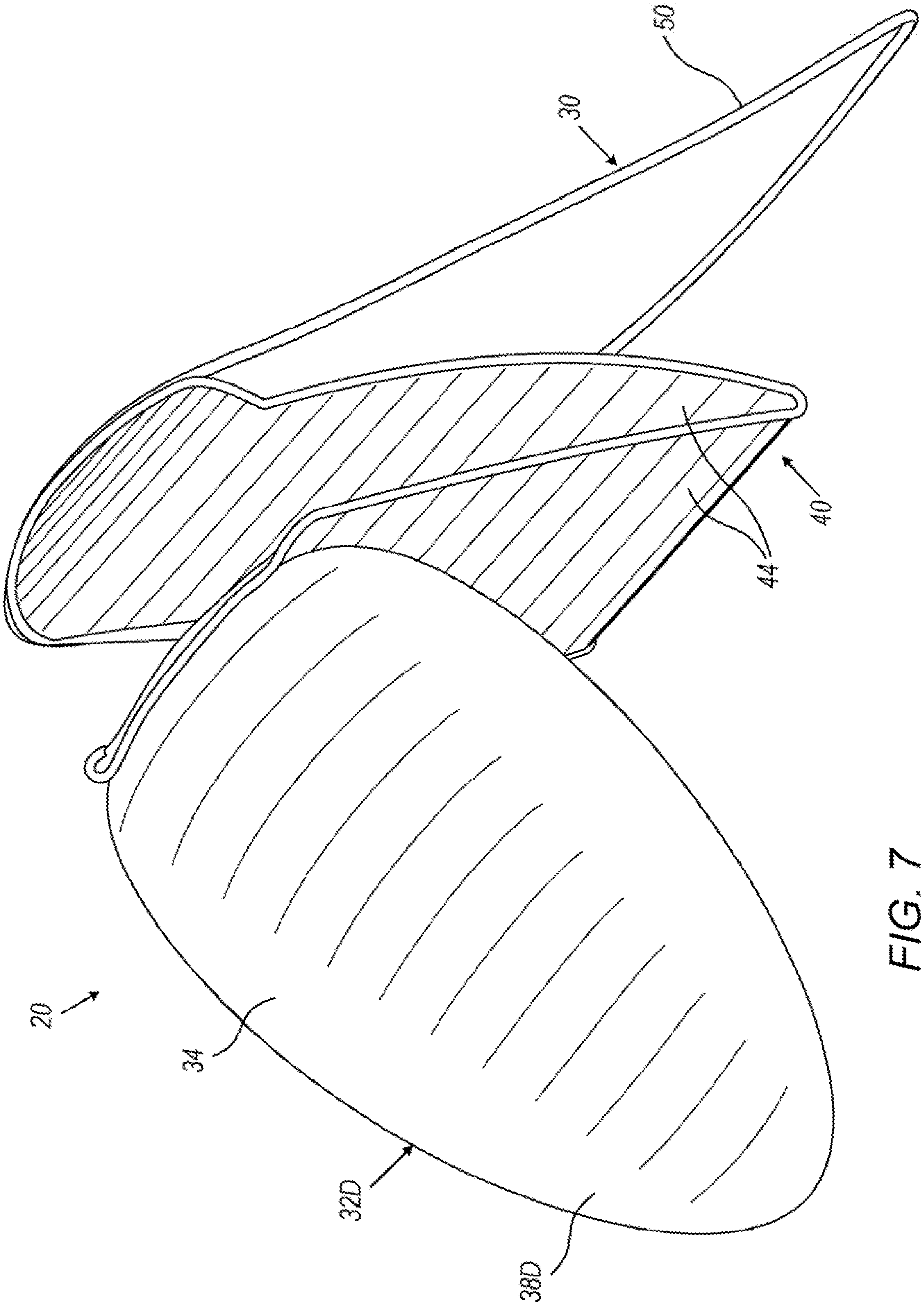
FIG. 7 is a schematic illustration of another configuration of the coaptation-assist device of FIGS. 1A-E and 2, in accordance with an application of the present invention.

Reference is now made to FIG. 7, which is a schematic illustration of another configuration of coaptation-assist device 20, in accordance with an application of the present invention. In this configuration, coaptation-assist device 20 comprises a neo-leaflet 32D, which, other than as described below, is identical to neo-leaflet 32 described hereinabove and may implement any of the features thereof, mutatis mutandis. Like neo-leaflet 32, neo-leaflet 32D comprises a neo-leaflet cover 38D that defines coaptation surface 34. However, unlike neo-leaflet 32, neo-leaflet 32D does not comprise a wire loop that defines at least a portion of the border of the neo-leaflet and to which neo-leaflet cover 38D is attached. The lack of the wire loop provides greater flexibility to coaptation surface 34 of neo-leaflet 32D, such as to allow the coaptation surface to be dynamic throughout the cardiac cycle, as described hereinabove with reference to FIGS. 1A-E and 2. Optionally, neo-leaflet 32D comprises one or more stiffening elements within neo-leaflet cover 38D to prevent the neo-leaflet from prolapsing in the atrial chamber as a result of an increase of backflow pressure over the neo-leaflet's ventricular surface during the cardiac cycle.

Figure 8A:
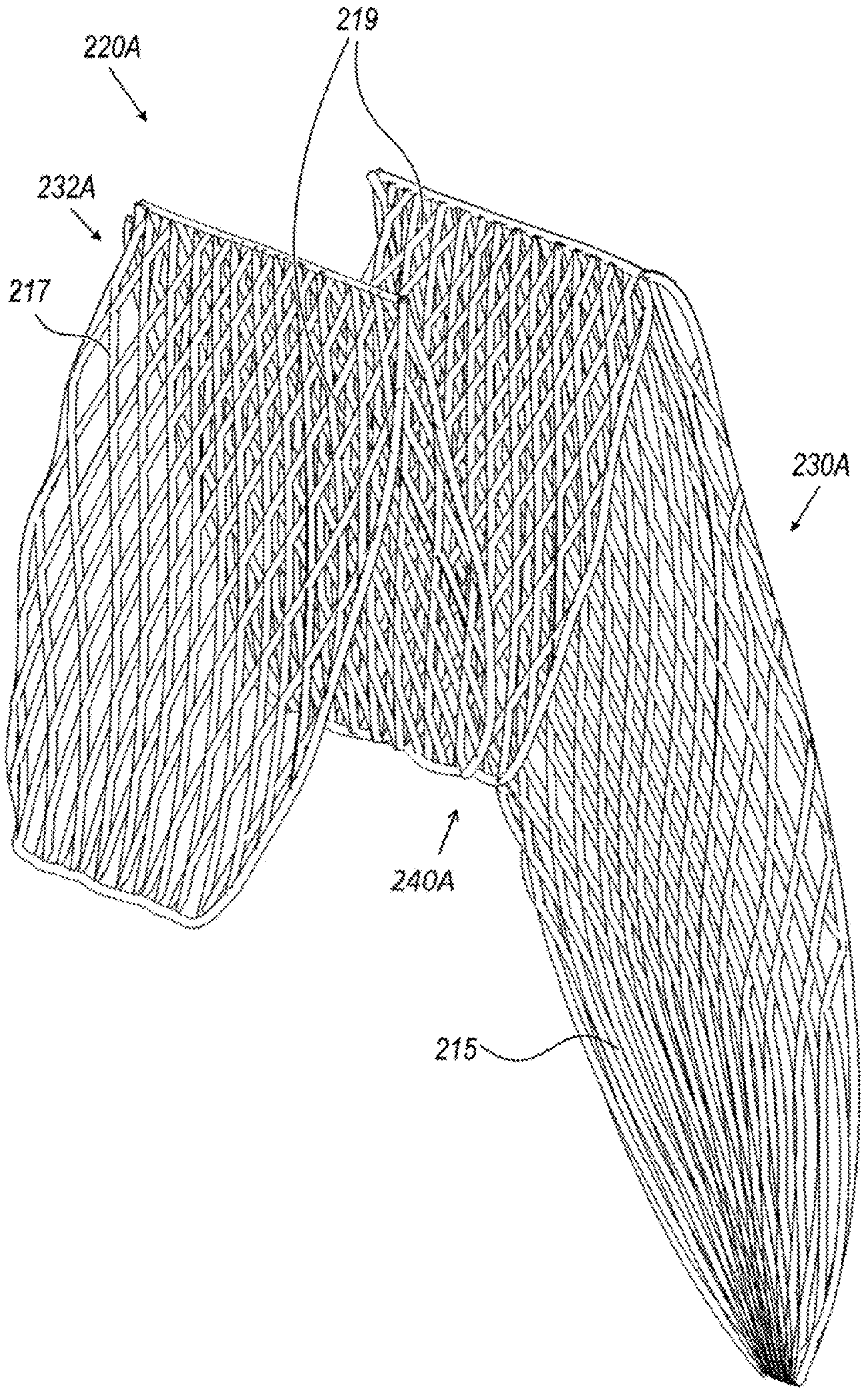
FIGS. 8A-B are schematic illustrations of additional coaptation-assist devices, respectively, in accordance with respective applications of the present invention.
Figure 8B:
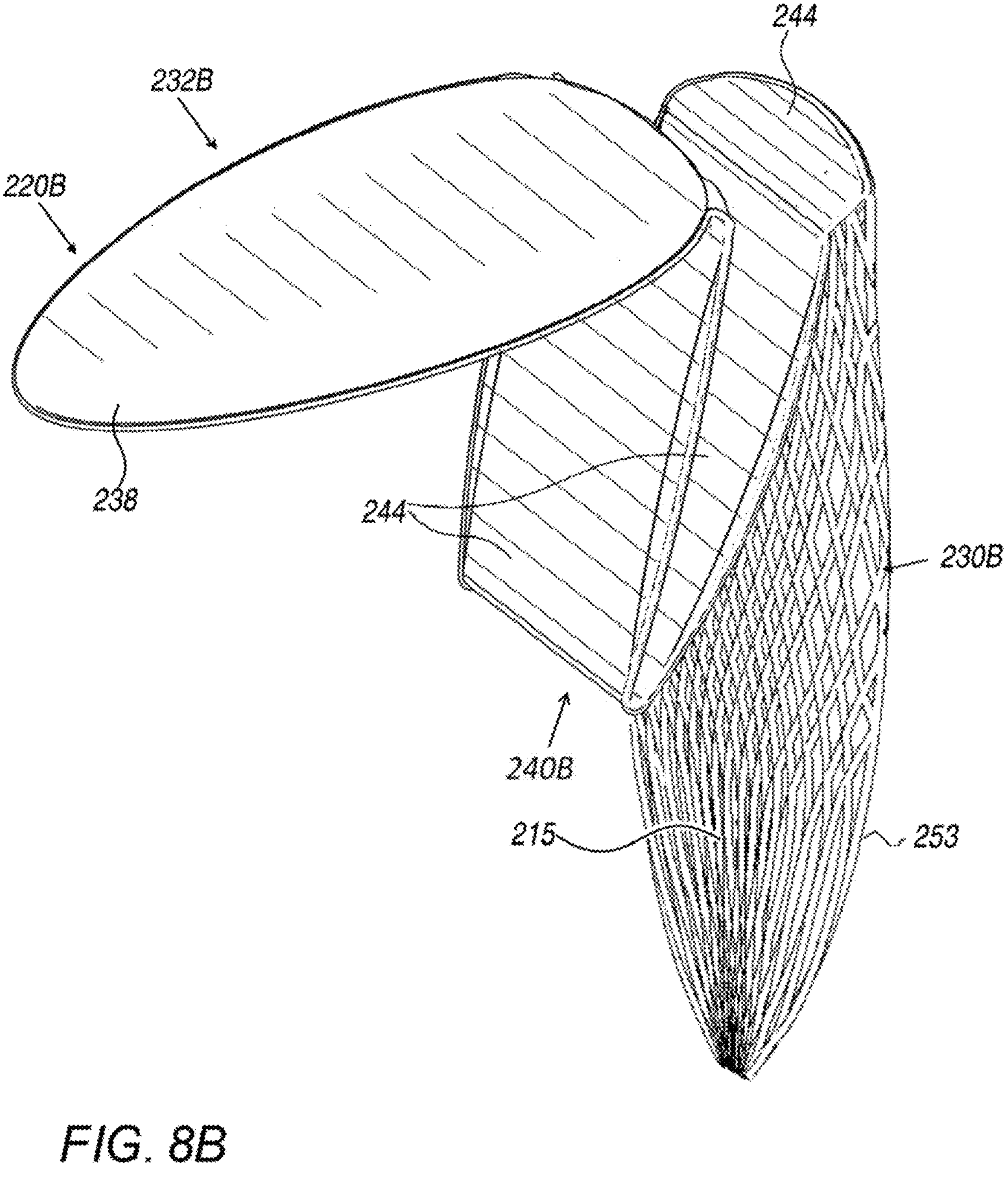

Reference is now made to FIGS. 8A-B, which are schematic illustrations of coaptation-assist devices 220A and 220B, respectively, in accordance with respective applications of the present invention. Other than as described hereinbelow, coaptation-assist devices 220A and 220B are generally similar to coaptation-assist device 20, described hereinabove with reference to FIGS. 1A-E and 2, and like reference numerals refer to like parts. Coaptation-assist devices 220A and 220B, including their respective neo-leaflets, loop-shaped ventricular anchors, and optional native-leaflet graspers, may implement any of the features of coaptation-assist device 20, mutatis mutandis, including the features described hereinabove with reference to FIGS. 3A-K and the features described hereinabove with reference to FIGS. 4A-B.

Coaptation-assist devices 220A and 220B comprise loop-shaped ventricular anchors 230A and 230B, respectively, each of which comprises a braided flat sheet 215 comprising braided wires, which typically comprise metal. The braided wires are arranged to provide a loop-shaped border to loop-shaped ventricular anchors 230A and 230B. Loop-shaped ventricular anchors 230B of coaptation-assist device 220B further comprises an anchor cover 253, which is attached to and covers all or a portion of braided flat sheet 215 (on one side, as illustrated, or both sides). Anchor cover 253 may comprise a synthetic or biological material impregnated within the braid of braided flat sheet 215, or may comprise a separate synthetic or biological flat sheet of material that is attached to braided flat sheet 215. Anchor cover 253 may implement any of the features of the anchor-loop covers described hereinabove with reference to FIGS. 1A-E and 3A-K, mutatis mutandis.

Typically, loop-shaped ventricular anchors 230A and 230B are configured to remain anchored in position by force (typically radially-outwardly-directed force) applied by loop-shaped ventricular anchors 230A and 230B to the surrounding anatomy, and/or by friction between loop-shaped ventricular anchors 230A and 230B and the surrounding anatomy. For some applications, loop-shaped ventricular anchors 230A and 230B comprise a self-expandable material, such as a shape-memory alloy (e.g., Nitinol) that causes the braiding of loop-shaped ventricular anchors 230A and 230B to expand radially outwardly so as to apply the force. For these applications, loop-shaped ventricular anchors 230A and 230B typically are configured to have a shape in its resting (relaxed) state that is larger than the surrounding anatomy (at least in one direction, i.e., with a loop height greater than the ventricular height, or a loop width greater than the ventricular wall width). As a result, the surrounding anatomy limits expansion of loop-shaped ventricular anchors 230A and 230B and loop-shaped ventricular anchors 230A and 230B apply a force to the surrounding anatomy (and vice versa). In addition, the narrowing of ventricular wall 27 in a subannular-to-apical direction compresses loop-shaped ventricular anchors 230A and 230B, creating a counter-radial force, and directing loop-shaped ventricular anchors 230A and 230B to stabilize itself at the sub-leaflet ventricular hinge level (i.e., at the level of subannular surface 25) (where, optionally, loop-shaped ventricular anchors 230A and 230B also function to grasp target native leaflet 26 in some configurations, optionally in conjunction with native-leaflet graspers 240A and 240B, respectively, described hereinbelow).

Coaptation-assist devices 220A and 220B further comprise neo-leaflets 232A and 232B, respectively, which comprise a braided flat sheet 217 (shown and labeled in FIG. 8A, but not visible in FIG. 8B because it is covered by a neo-leaflet cover 238, as described immediately below). Neo-leaflet 232B of coaptation-assist device 220B further comprises a neo-leaflet cover 238, which covers all or a portion of braided flat sheet 217. Neo-leaflet cover 238 may comprise a synthetic or biological material impregnated within the braid of braided flat sheet 217, or may comprise a separate synthetic or biological flat sheet of material that is attached to braided flat sheet 217. Neo-leaflet cover 238 may implement any of the features of neo-leaflet cover 38, described hereinabove with reference to FIGS. 1A-E and 2, mutatis mutandis.

For some applications, coaptation-assist devices 220A and 220B further comprise native-leaflet grasper 240A and 240B, respectively, which comprise one or more braided flat sheets 219 (shown and labeled in FIG. 8A, but not visible in FIG. 8B because it is covered by one or more grasper covers 244, as described immediately below). Native-leaflet grasper 240B of coaptation-assist device 220B further comprises one or more grasper covers 244, which covers all or a portion of braided flat sheet 219. The one or more grasper covers 244 may implement any of the features of the one or more grasper covers 44, described hereinabove with reference to FIGS. 1A-E and 2, mutatis mutandis.

For some applications, coaptation-assist device 220B comprises only a subset of the covers described above.

For some applications, neo-leaflets 232A and 232B are configured such that coaptation surface 34 is generally static throughout a cardiac cycle of the subject upon implantation of coaptation-assist devices 220A and 220B, respectively, in a heart of the subject, such as described hereinabove regarding coaptation-assist device 20. For some of these applications, neo-leaflets 232A and 232B comprise stiffener elements thereupon, and/or are connected mechanically after implantation to loop-shaped ventricular anchors 230A and 230B, respectively, by wires, sutures, or rods that extend from the free edge of neo-leaflets 232A and 232B to the braided body of loop-shaped ventricular anchors 230A and 230B, respectively. These techniques help avoid movement of neo-leaflets 232A and 232B into the atrium during the cardiac cycle.

For other applications, neo-leaflets 232A and 232B are configured such that coaptation surface 34 moves toward and away from the one or more opposing native leaflets 28 during a cardiac cycle of the subject upon implantation of coaptation-assist devices 220A and 220B, respectively, in a heart of the subject, such as described hereinabove regarding coaptation-assist device 20.

Reference is now made to FIGS. 9A-H, which are schematic illustrations of a method of implanting coaptation-assist device 20 in a heart of a subject, in accordance with an application of the present invention. Although the method is illustrated for coaptation-assist device 20, it may also be used to implant the other coaptation-assist devices described herein, mutatis mutandis. In addition, the illustrated native valve 22 is a tricuspid valve 300, the method may also be modified to treat a mitral valve 302.

Figure 9A:
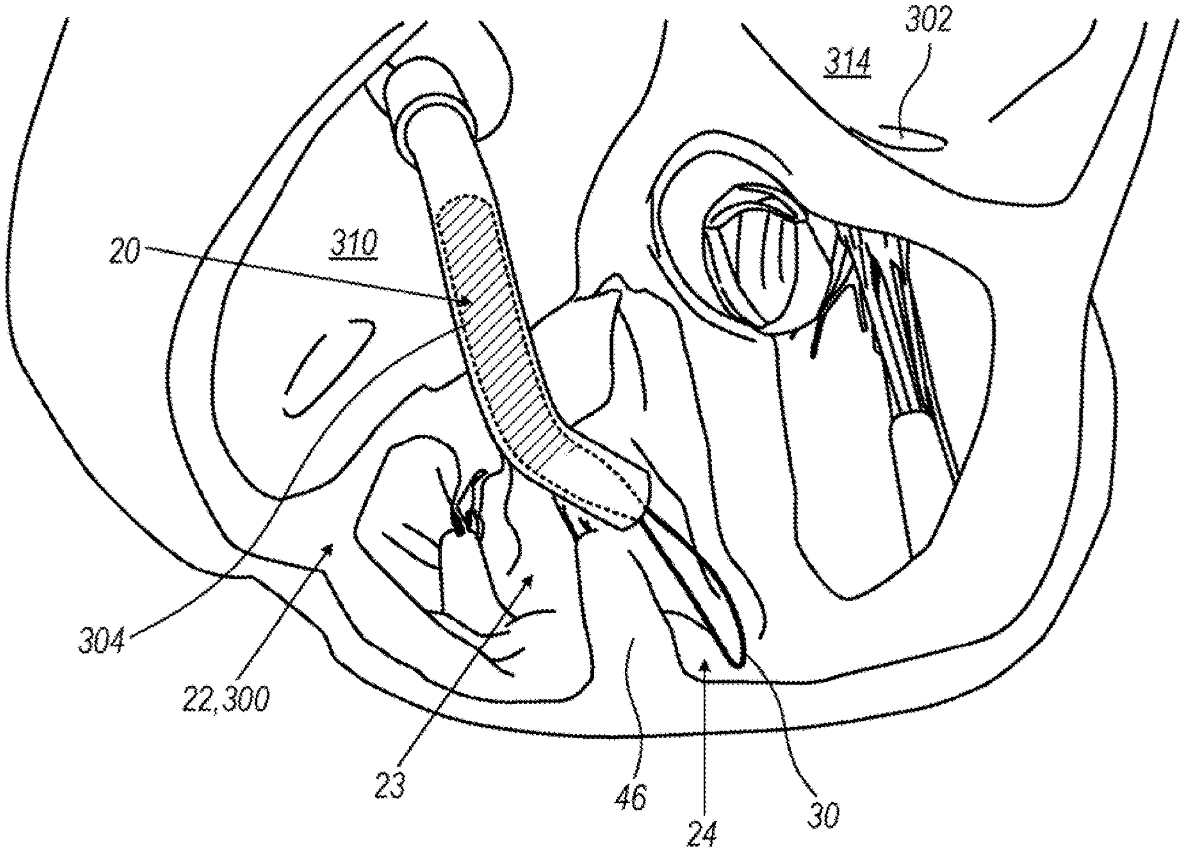
FIGS. 9A-H are schematic illustrations of a method of implanting the coaptation-assist device of FIGS. 1A-E and 2 in a heart of a subject, in accordance with an application of the present invention.

As shown in FIG. 9A, coaptation-assist device 20 is percutaneously (endovascularly) delivered to a heart of the subject while coaptation-assist device 20 is removably disposed in a delivery tube 304 of a delivery system in a compressed configuration. For some applications, coaptation-assist device 20 is loaded in the compressed configuration into delivery tube 304 by extending and flattening coaptation-assist device 20 into the elongate flattened configuration shown in FIG. 1E, and then further radially compressing (e.g., crimping) the device. For example, delivery tube 304 may be advanced into right atrium 310 via the inferior or superior vena cava. For applications in which coaptation-assist device 20 is used to treat mitral valve 302, delivery tube 304 may be advanced transseptally into a left ventricle 314, using transseptal advancement techniques known in the art. Alternatively, coaptation-assist device 20 is delivered in a minimally-invasive procedure.

The delivery system typically comprises delivery tube 304 and optionally one or more additional tubes. One or more of the tubes is steerable (e.g., two are steerable, one for trajectory, and the other for positioning). Optionally, coaptation-assist device 20 is partially disposed in delivery tube 304 and partially disposed in another of the tubes, to allow sequential deployment of the elements of coaptation-assist device 20. For configurations in which coaptation-assist device 20 is entirely disposed within delivery tube 304, typically loop-shaped ventricular anchor 30 is disposed more distally within the tube than neo-leaflet 32 (i.e., closer to the distal end of the tube), to allow loop-shaped ventricular anchor 30 to be deployed from the tube before neo-leaflet 32 is deployed. Alternatively, the arrangement is reversed, to allow neo-leaflet 32 to be deployed from the tube before loop-shaped ventricular anchor 30 is deployed.

Figure 9B:
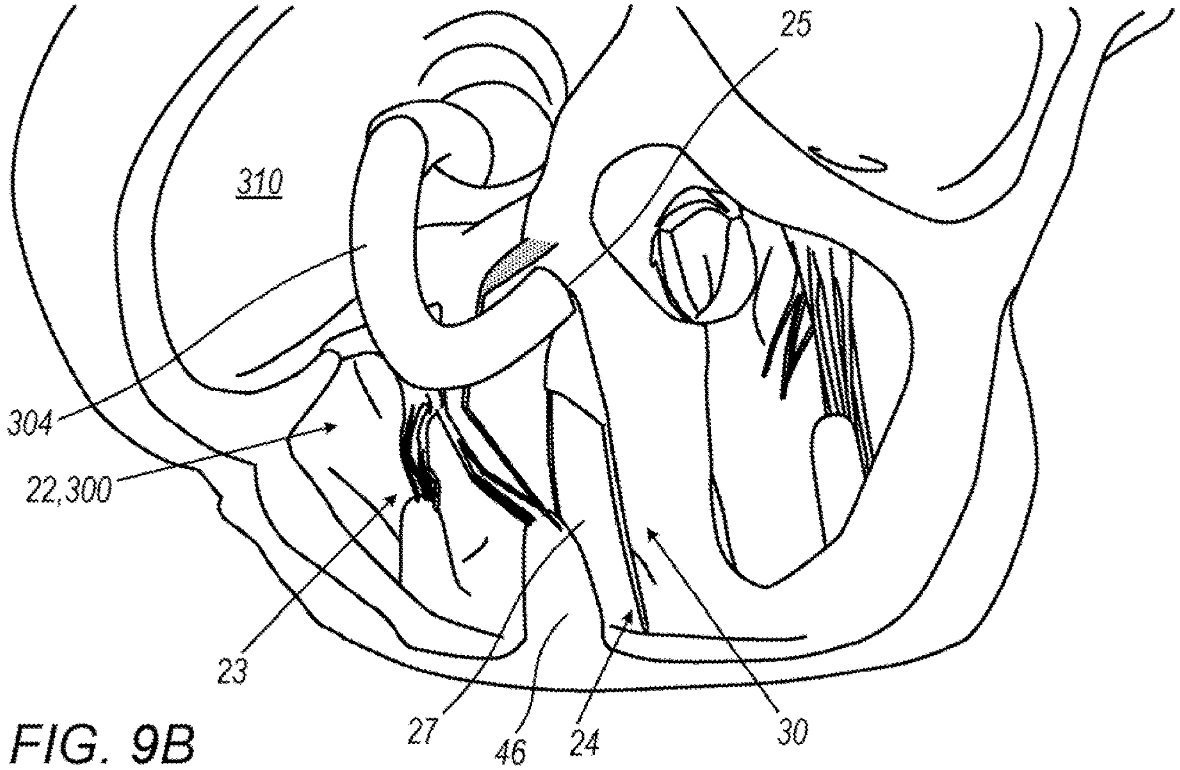
Figure 9C:
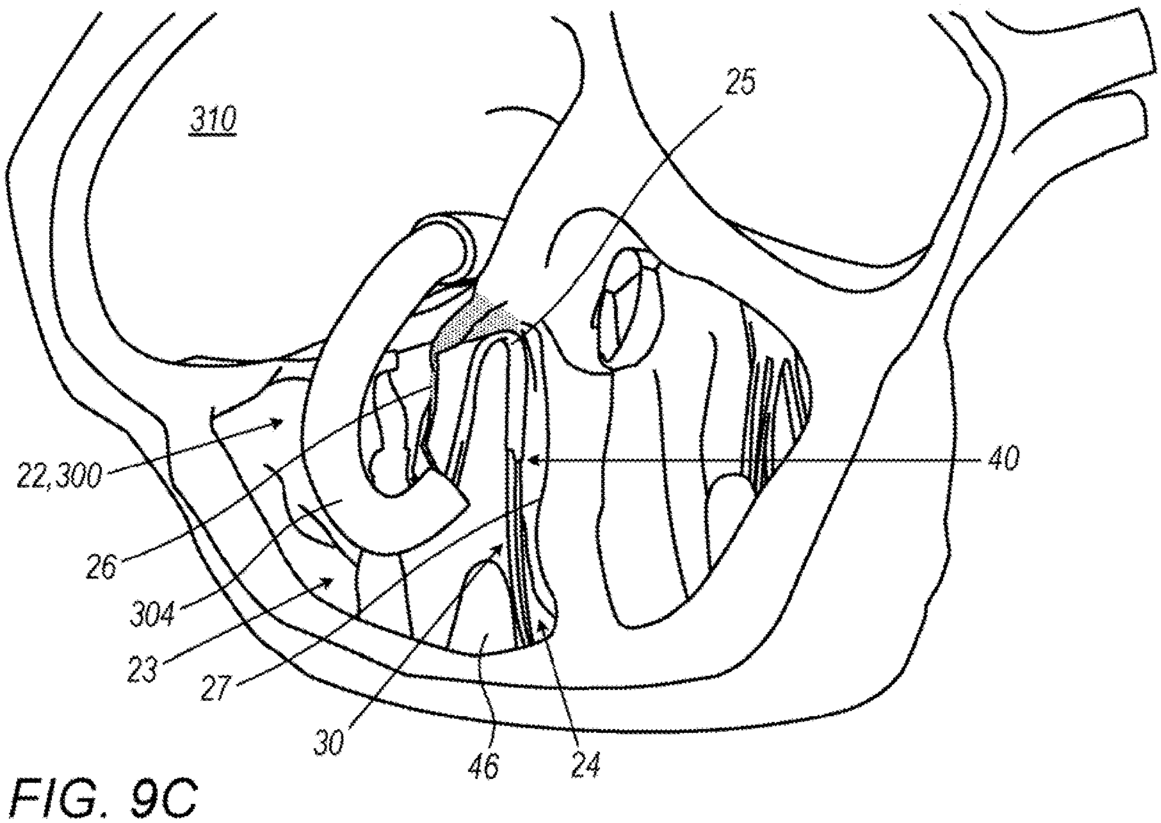

As shown in FIGS. 9A-C, loop-shaped ventricular anchor 30 is deployed from delivery tube 304 and positioned in ventricle 23 (the right ventricle in the illustrated method), such that anchor-loop wire loop 50 extends between ventricular apical area 24 and subannular surface 25 (shown in FIG. 9B and later figures) of target native leaflet 26 of native valve 22, 300, such that anchor-loop wire loop 50 remains anchored in position against surrounding anatomy, including subannular surface 25, ventricular wall 27, and ventricular apical area 24. Typically, loop-shaped ventricular anchor 30 is deployed by proximally withdrawing delivery tube 304 and/or pushing the loop-shaped ventricular anchor from delivery tube 304.

For some applications, loop-shaped ventricular anchor 30 is positioned such that anchor-loop wire loop 50 remains anchored in position by force applied by anchor-loop wire loop 50 to the surrounding anatomy. Alternatively or additionally, for some applications, loop-shaped ventricular anchor 30 is positioned such that anchor-loop wire loop 50 remains anchored in position by friction between anchor-loop wire loop 50 and the surrounding anatomy.

For some applications, loop-shaped ventricular anchor 30 is configured to be atraumatic, and positioning loop-shaped ventricular anchor 30 does not comprise penetrating tissue of the surrounding anatomy with loop-shaped ventricular anchor 30. For some applications, the deployment method does not comprise penetrating tissue with any elements of coaptation-assist device 20. Alternatively, tissue is penetrated, such as described hereinbelow with reference to FIGS. 21-22, or with barbs arranged along at least a portion of anchor-loop wire loop 50 (such as barbs 301J, shown in FIG. 3J).

For some applications, as shown in FIGS. 9A-H, target native leaflet 26 is a native septal leaflet of tricuspid valve 300, and ventricular wall 27 is a ventricular septal wall. Neo-leaflet 32 is positioned such that neo-leaflet 32 at least partially replaces function of the septal leaflet by providing a surface of coaptation 34 for one or more of the opposing native posterior and anterior leaflets of the tricuspid valve, when anchor-loop wire loop 50 is positioned in ventricle 23 and remains anchored in position against the surrounding anatomy, including subannular surface 25, ventricular septal wall 27, and ventricular apical area 24.

For other application, native valve 22 is mitral valve 302, and neo-leaflet 32 is positioned such that neo-leaflet 32 at least partially replaces function of target native leaflet 26 by providing a surface of coaptation 34 for the opposing native leaflet of the mitral valve, when anchor-loop wire loop 50 is positioned in ventricle 23. For some of these applications, target native leaflet 26 is a native anterior leaflet of mitral valve 302, ventricular wall 27 is a ventricular septal wall, and neo-leaflet 32 is positioned such that neo-leaflet 32 at least partially replaces function of the native anterior leaflet by providing a surface of coaptation 34 for an opposing native posterior leaflet of mitral valve 302, when anchor-loop wire loop 50 is positioned in ventricle 23 and remains anchored in position against the surrounding anatomy, including subannular surface 25, ventricular septal wall 27, and ventricular apical area 24.

Figure 9D:
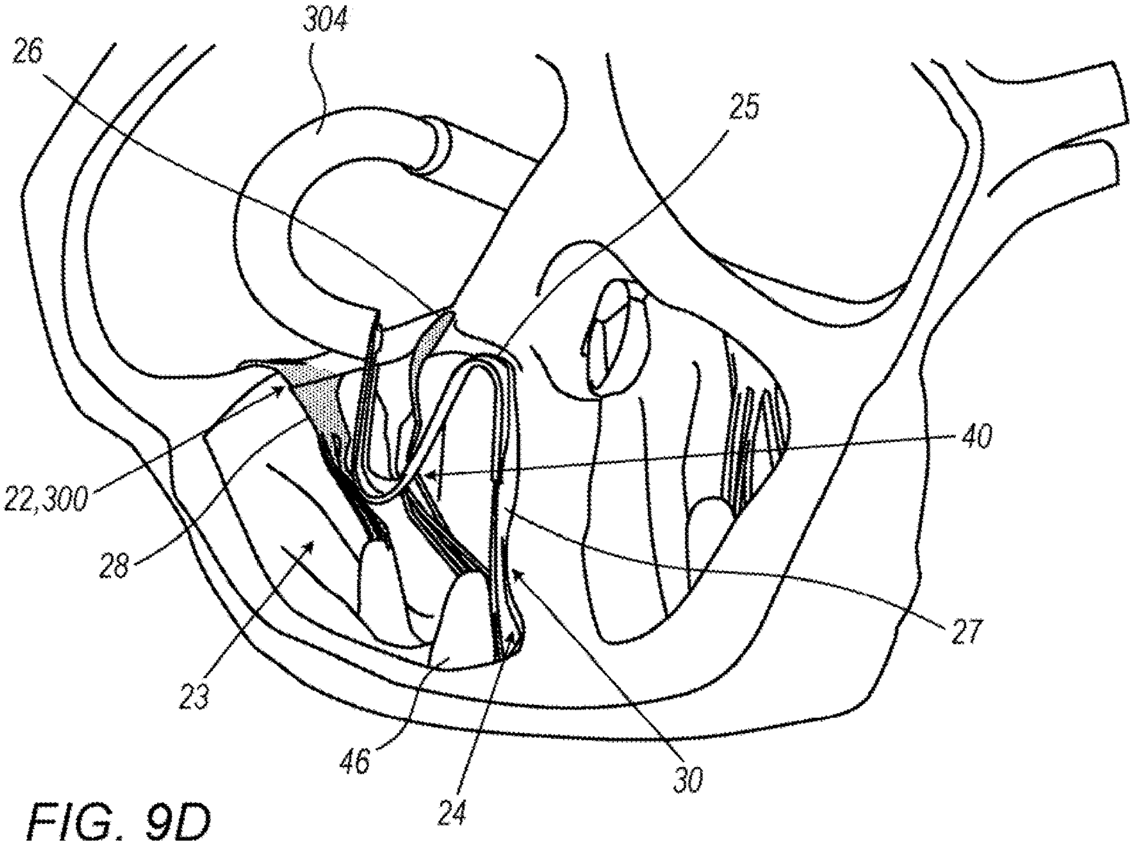
Figure 9E:
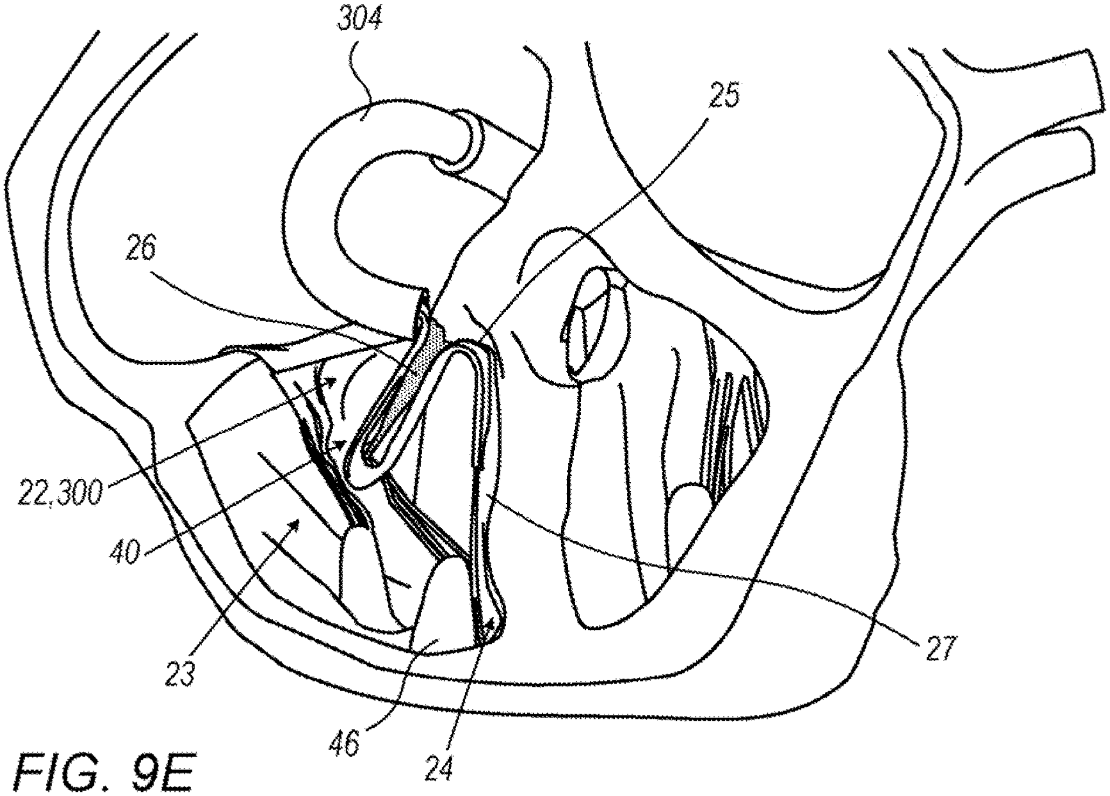
Figure 9F:
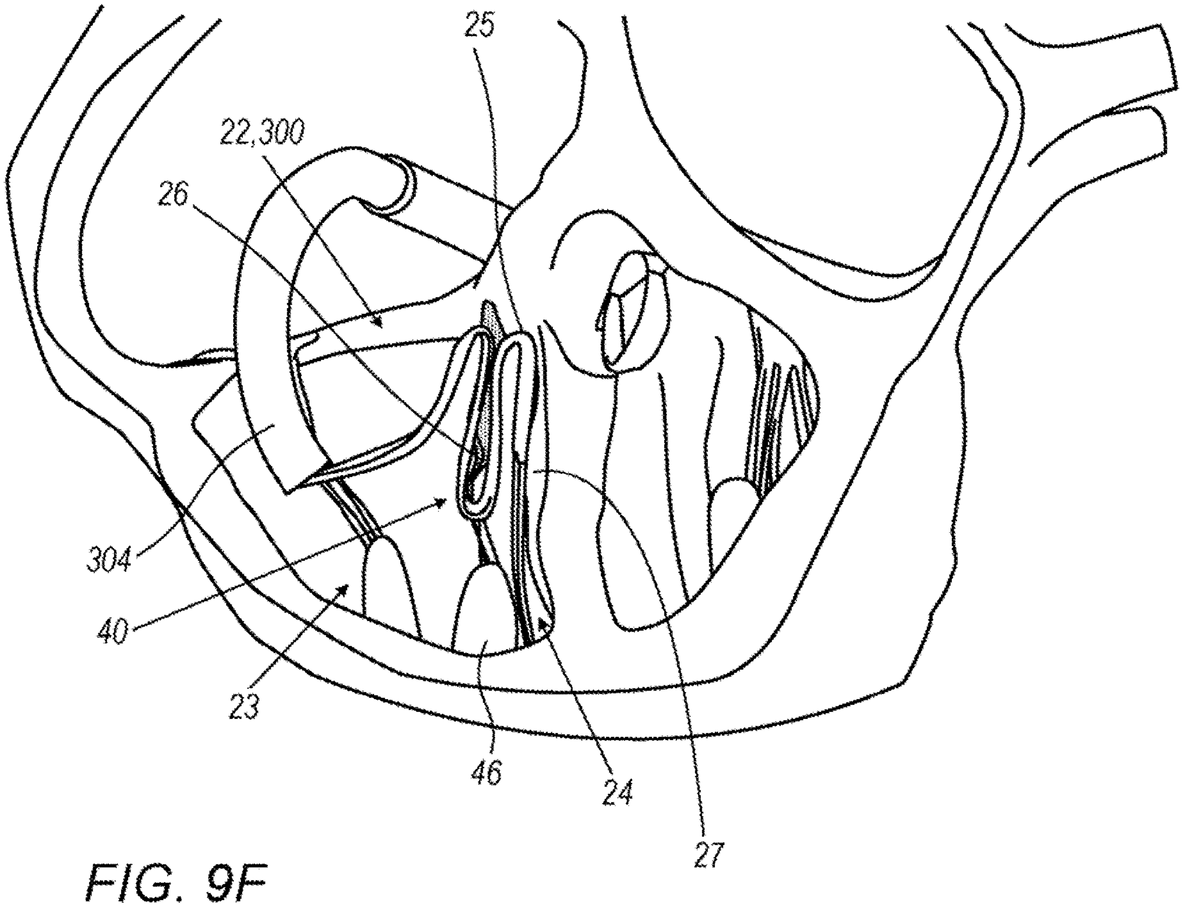
Figure 9G:
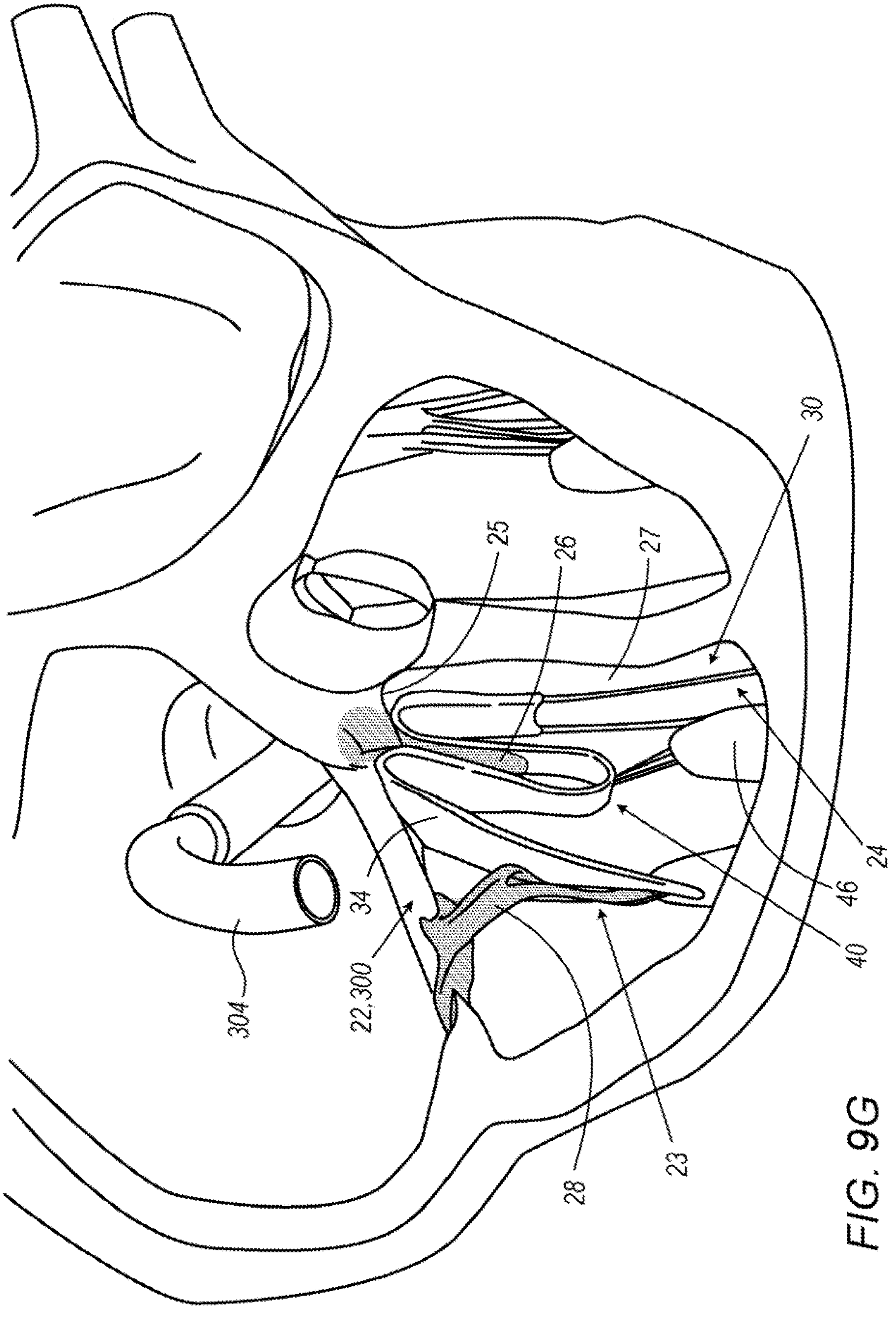
Figure 9H:
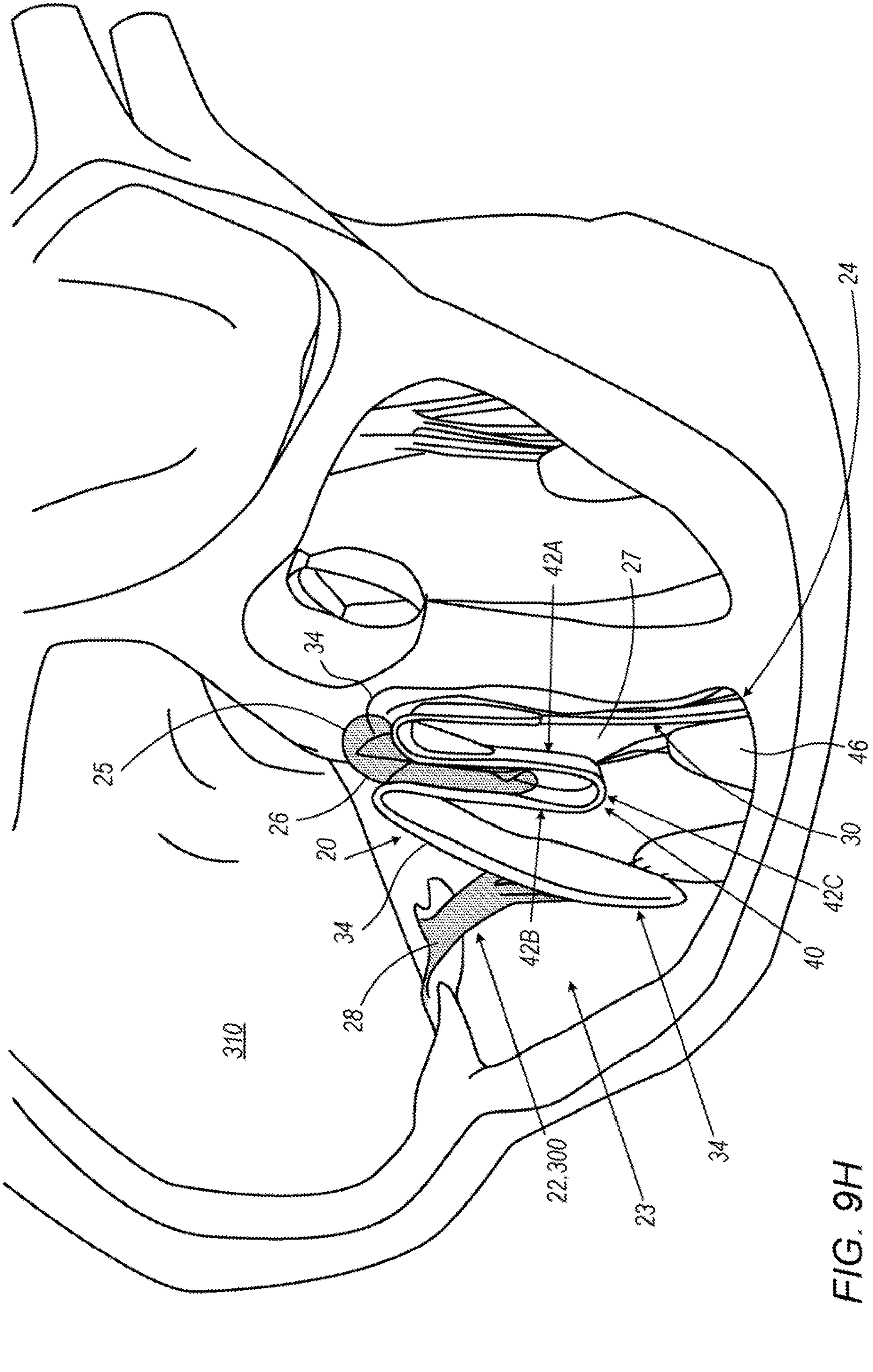

As shown in FIGS. 9F-H, neo-leaflet 32 is deployed from delivery tube 304 and positioned such that neo-leaflet 32 at least partially replaces function of target native leaflet 26 by providing coaptation surface 34 for one or more opposing native leaflets 28 that oppose target native leaflet 26, when anchor-loop wire loop 50 is positioned in ventricle 23. As mentioned above, neo-leaflet 32 is supported by loop-shaped ventricular anchor 30. Typically, loop-shaped ventricular anchor 30 is deployed by proximally withdrawing delivery tube 304.

Although loop-shaped ventricular anchor 30 is shown and described as being deployed before neo-leaflet 32, in some configurations the order of deployment is reversed (configuration not shown).

For some applications, as shown in FIGS. 9F-H, neo-leaflet 32 is positioned such that coaptation surface 34 of neo-leaflet 32 crosses from an atrial side to a ventricular side of a native valvular plane, when anchor-loop wire loop 50 is positioned in ventricle 23, so that the native leaflet 28 coapts with neo-leaflet 32 during the cardiac cycle, with the atrial surface of native leaflet 28 coming into contact with atrial surface 345 of the neo-leaflet, thereby stopping blood passage from the ventricle to the atrium during the systolic cardiac cycle phase.

For some applications, as shown in FIGS. 9C-E, the deployment method further comprises positioning native-leaflet grasper 40 to grasp atrial and ventricular surfaces of target native leaflet 26, in order to support neo-leaflet 32, and to orient neo-leaflet 32 with respect to native valve 22, 300. In the illustrated method, native-leaflet grasper 40 is positioned after positioning loop-shaped ventricular anchor 30 and before positioning neo-leaflet 32. Alternatively, native-leaflet grasper 40 is positioned at a different point in the deployment method.

For some applications, positioning native-leaflet grasper 40 to grasp atrial and ventricular surfaces of target native leaflet 26 comprises sandwiching at least a portion of the atrial and the ventricular surfaces of target native leaflet 26 between first and second portions 42A and 42B of native-leaflet grasper 40, as shown in FIGS. 9D-H (labeled in FIG. 9H) (as well as in FIG. 2). For some applications, sandwiching at least a portion of the atrial and the ventricular surfaces of target native leaflet 26 comprises folding first and second portions 42A and 42B of native-leaflet grasper 40 toward each other so as to grasp the atrial and the ventricular surfaces of target native leaflet 26 by sandwiching at least a portion of the atrial and the ventricular surfaces of target native leaflet 26 between first and second portions 42A and 42B of native-leaflet grasper 40, as shown in FIGS. 9D-H (labeled in FIG. 9H) (as well as in FIG. 2). For some of these applications, folding first and second portions 42A and 42B of native-leaflet grasper 40 toward each other comprises extending, around the free edge of target native leaflet 26, a third portion 42C defined by native-leaflet grasper 40 at a fold between first and second portions 42A and 42B of native-leaflet grasper 40, as shown in FIGS. 9D-H (labeled in FIG. 9H) (as well as in FIG. 2).

For some applications, as shown in FIGS. 9A-C, loop-shaped ventricular anchor 30 is positioned such that anchor-loop wire loop 50 remains anchored in position against subannular surface 25, ventricular septal wall 27, and one or more ventricular papillary muscles 46 of ventricular apical area 24.

Figure 10A:
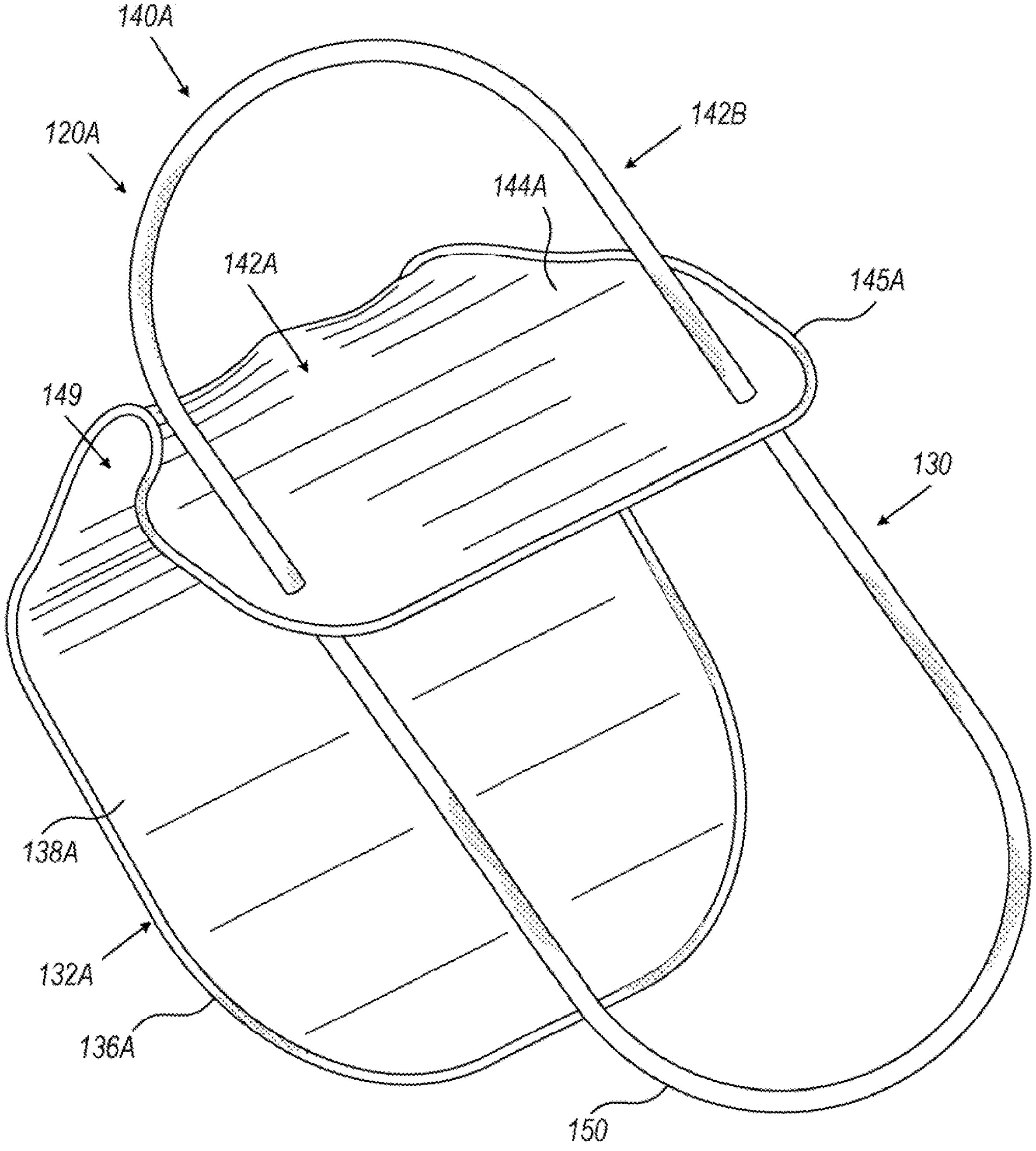
FIGS. 10A-C are schematic illustrations of a coaptation-assist device, in accordance with an application of the present invention.
Figure 10B:
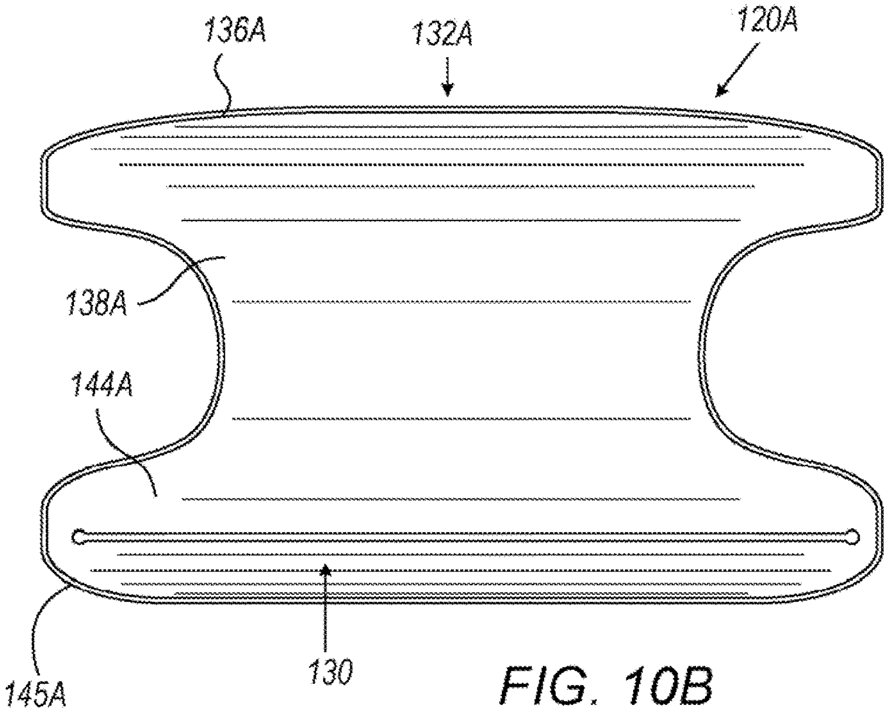
Figure 10C:
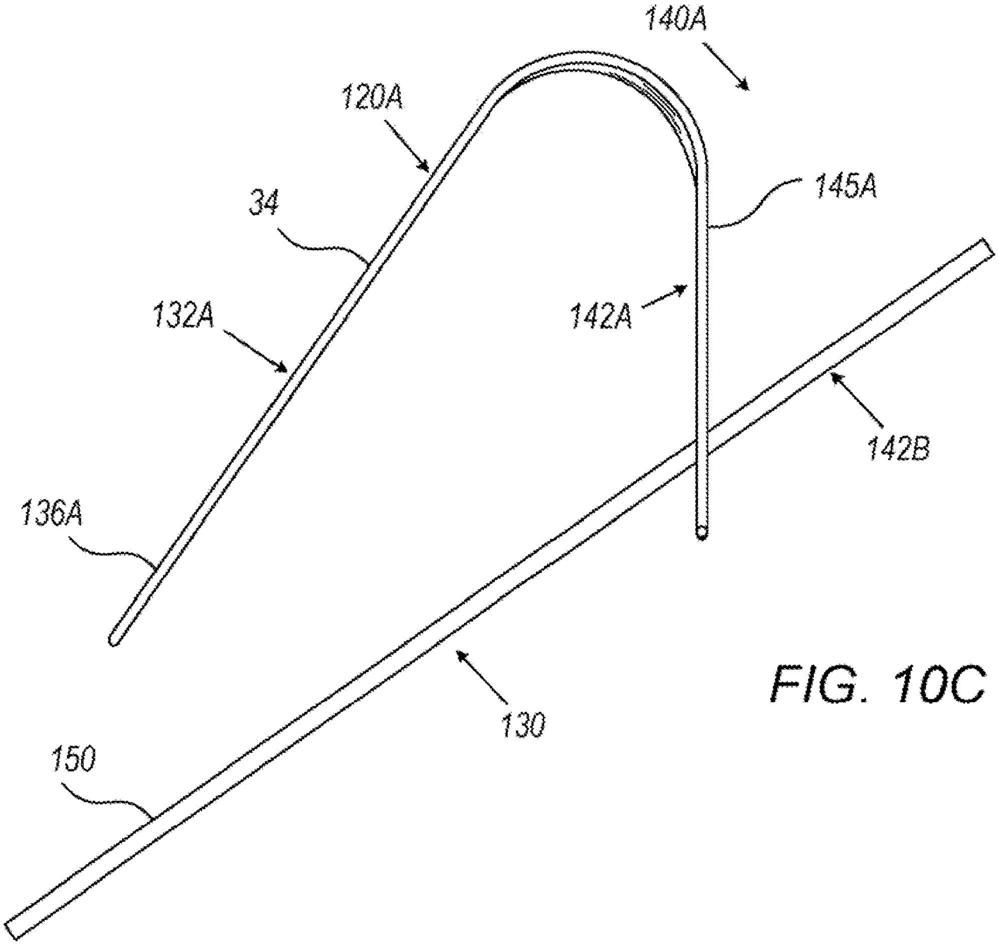
Figure 10G:
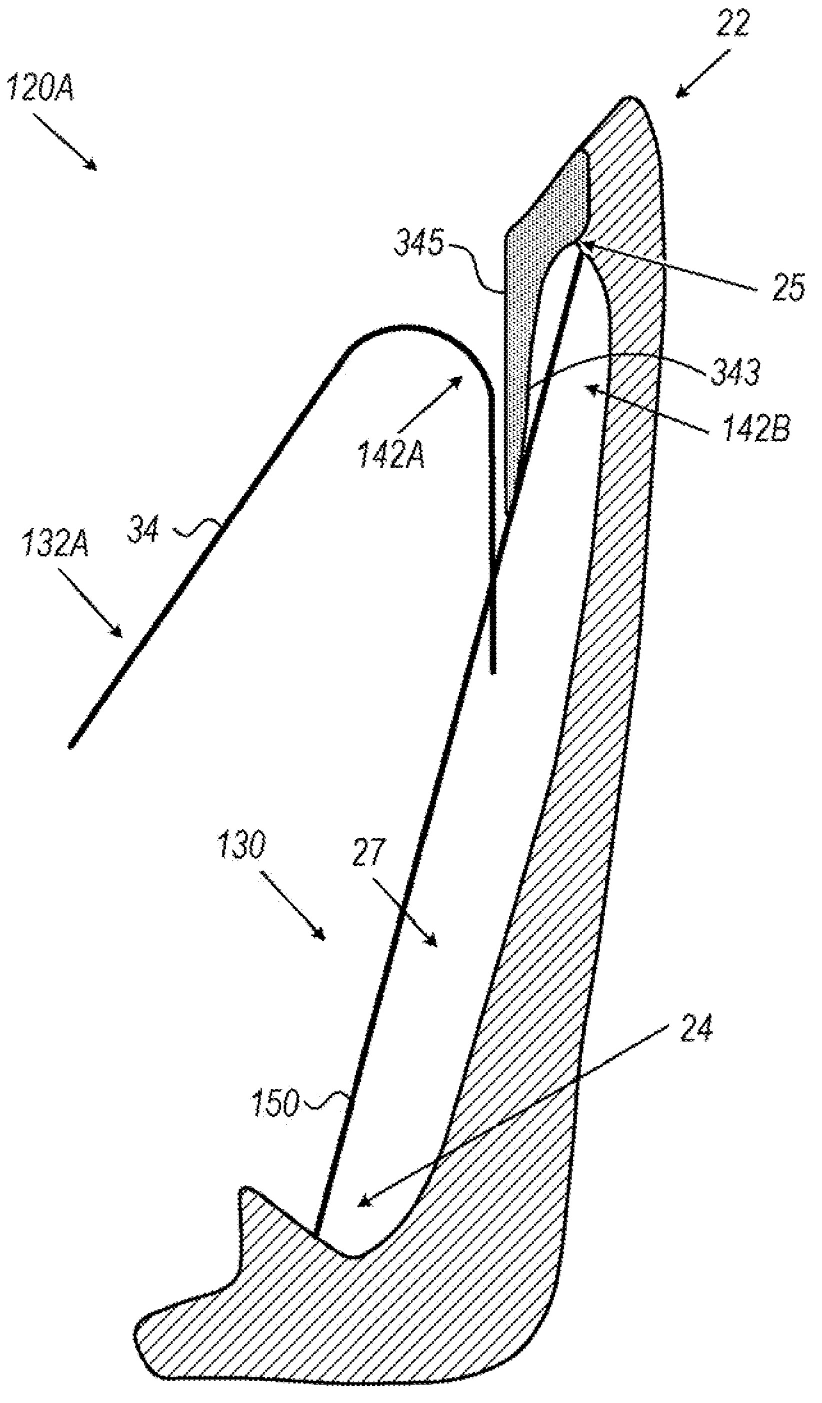
FIG. 10G is a schematic illustration of the coaptation-assist device of FIGS. 10A-C implanted in a native valve, in accordance with an application of the present invention.
Figure 11A:
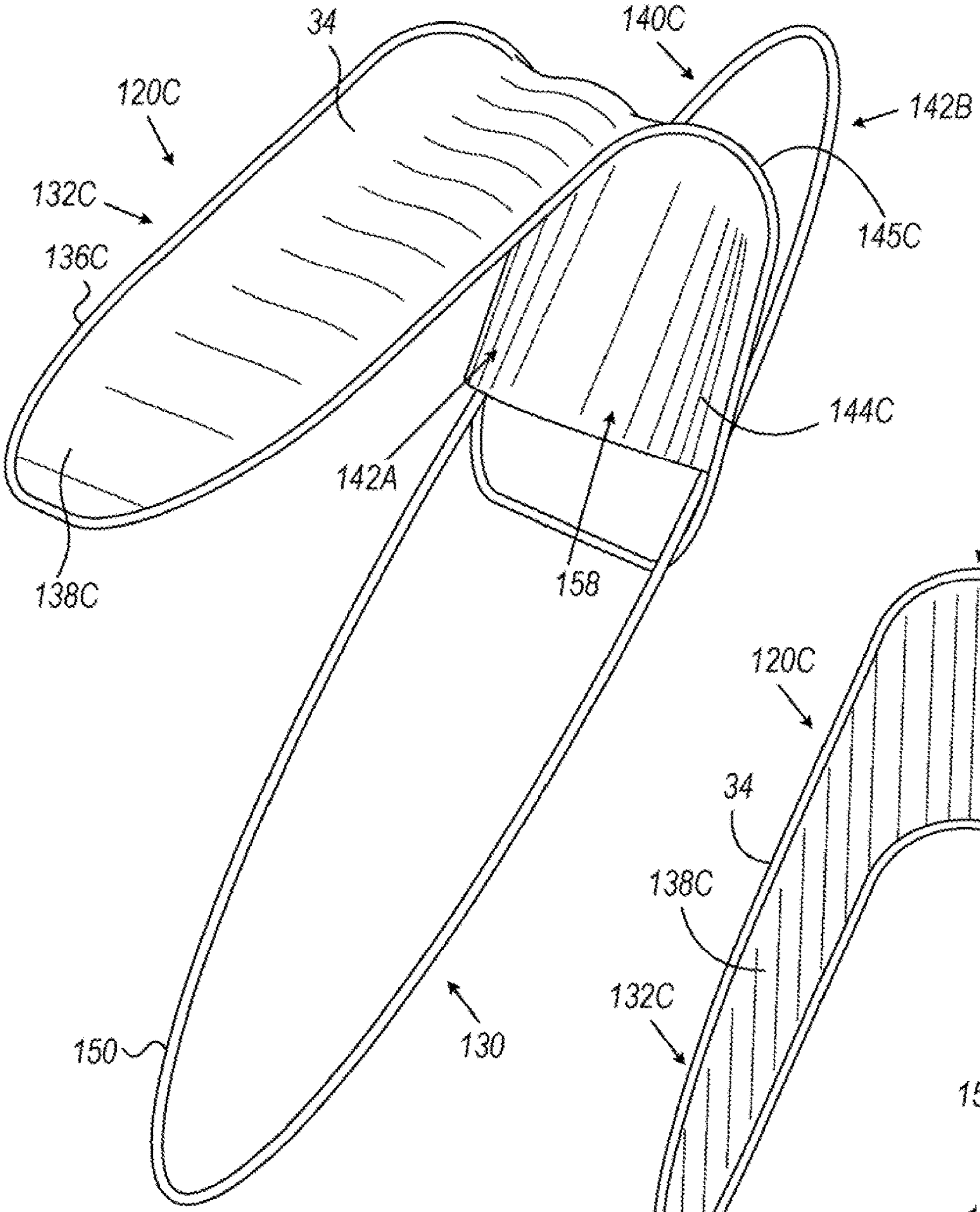
FIGS. 11A-D are schematic illustrations of yet another coaptation-assist device, in accordance with an application of the present invention.
Figure 11B:
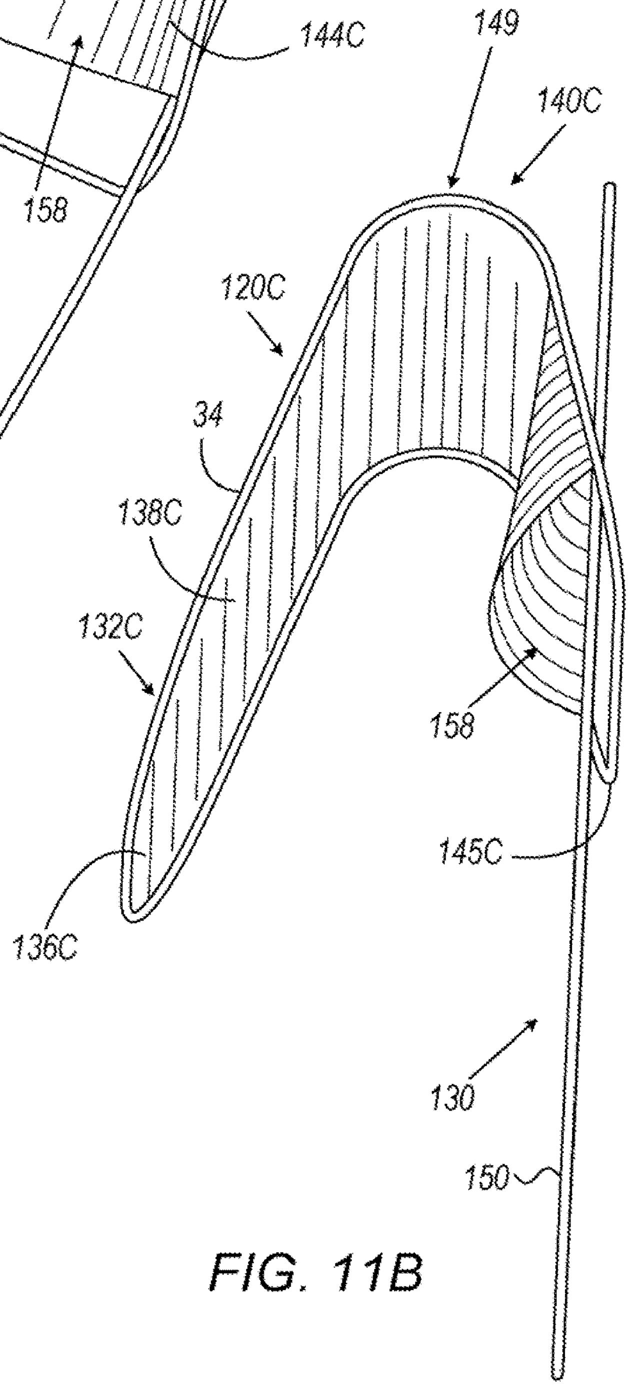
Figure 11C:
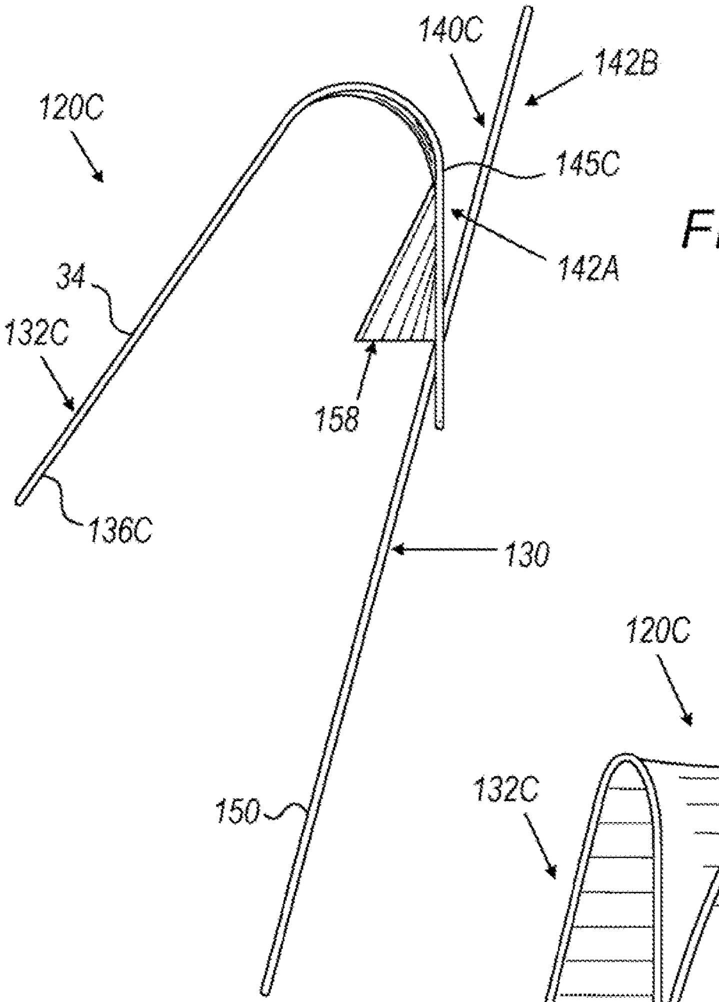
Figure 11D:
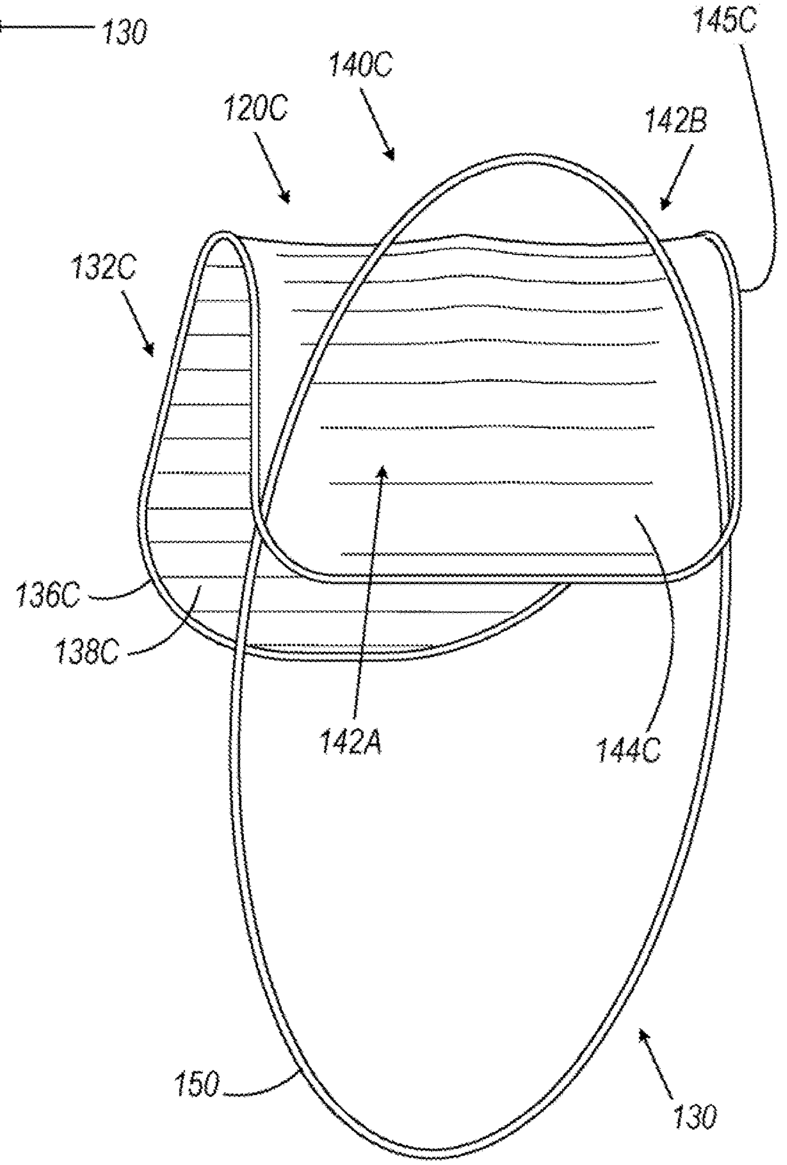

Reference is now made to FIGS. 10A-C, which are schematic illustrations of a coaptation-assist device 120A, in accordance with an application of the present invention. Reference is also made to FIGS. 10D-F, which are schematic illustrations of a coaptation-assist device 120B, in accordance with an application of the present invention. Reference is additionally made to FIG. 10G, which is a schematic illustration of coaptation-assist device 120A implanted in native valve 22, in accordance with an application of the present invention. Reference is further made to FIGS. 11A-D, which are schematic illustrations of a coaptation-assist device 120C, in accordance with an application of the present invention. Other than as described hereinbelow, coaptation-assist devices 120A, 120B, and 120C are generally similar to coaptation-assist device 20, described hereinabove with reference to FIGS. 1A-E and 2, and like reference numerals refer to like parts. Coaptation-assist devices 120A, 120B, and 120C may implement any of the features of coaptation-assist device 20, mutatis mutandis, including the features described hereinabove with reference to FIGS. 3A-K and the features described hereinabove with reference to FIGS. 4A-B.

Each of coaptation-assist devices 120A, 120B, and 120C comprises a loop-shaped ventricular anchor 130. Typically, loop-shaped ventricular anchor 130 comprises an anchor-loop wire loop 150, and a distal portion of anchor-loop wire loop 150 defines at least a portion of a border of the loop-shaped ventricular anchor. Anchor-loop wire loop 150 may implement any of the features of anchor-loop wire loop 50, described hereinabove with reference to FIGS. 1A-E, 2, and 3A-K, mutatis mutandis.

Coaptation-assist devices 120A, 120B, and 120C further comprise neo-leaflets 132A, 132B, and 132C, respectively, which are supported by loop-shaped ventricular anchor 130. Loop-shaped ventricular anchor 130 is disposed distally to the neo-leaflet.

Neo-leaflets 132A, 132B, and 132C are configured to at least partially replace function of target native leaflet 26 by providing coaptation surface 34 for one or more opposing native leaflets 28 that oppose target native leaflet 26, when anchor-loop wire loop 150 is positioned in ventricle 23. Neo-leaflets 132A, 132B, and 132C are typically configured to cover at least a portion of target native leaflet 26.

For some applications, neo-leaflets 132A, 132B, and 132C comprise neo-leaflet wire loops 136A, 136B, and 136C, respectively, which define portions of respective peripheries of the neo-leaflets, and neo-leaflet covers 138A, 138B, and 138C, respectively, attached to neo-leaflet wire loops 136A, 136B, and 136C, respectively. Typically, the neo-leaflet covers provide the above-mentioned coaptation surface 34. Neo-leaflet covers 138A, 138B, and 138C may implement any of the features of neo-leaflet cover 38, described hereinabove with reference to FIGS. 1A-E and 2, mutatis mutandis. In the illustrated configurations, neo-leaflet wire loops 136A, 136B, and 136C are shaped as open loops, which are open on a proximal side in the direction of loop-shaped ventricular anchor 130 and native-leaflet graspers 140A, 140B, and 140C, respectively, described below. (Each of the loops is considered open even though it is defined by a wire that also defines a portion of the native-leaflet grasper, because the portion of the wire that defines the loop is open.) Alternatively, neo-leaflet wire loops 136A, 136B, and 136C are shaped as closed loops, such as shown in FIGS. 1A-E (configuration not shown for coaptation-assist devices 120A, 120B, and 120C). Neo-leaflet wire loops 136A, 136B, and 136C may implement any of the features of neo-leaflet wire loop 36, described hereinabove with reference to FIGS. 1A-E and 2, mutatis mutandis.

Coaptation-assist devices 120A, 120B, and 120C further comprise native-leaflet graspers 140A, 140B, and 140C, respectively, which are configured to grasp atrial and ventricular surfaces 345 and 343 of target native leaflet 26, in order to support neo-leaflet 132A, 132B, and 132C, respectively, and to orient the neo-leaflets with respect to native valve 22.

For some applications, native-leaflet graspers 140A, 140B, and 140C comprise, respectively, one or more grasper covers 144A, 144B, and 144C. The one or more grasper covers, respectively, collectively comprise one or more biocompatible thin sheets of material (optionally, the same one or more sheets of material (e.g., the same exactly one sheet of material) define both neo-leaflet covers 138A, 138B, and 138C, described above, and the one or more grasper covers 144A, 144B, and 144C: alternatively, separate sheets of material define neo-leaflet covers 138A, 138B, and 138C and the one or more grasper covers 144A, 144B, and 144C). Typically, at least one of the one or more grasper covers pushes against atrial surface 345 of target native leaflet 26 to prevent blood flow between the target native leaflet and the coaptation-assist device. For some of these applications, the one or more grasper covers 144A, 144B, and 144C extend across and partially or entirely occupy a space at least partially surrounded by frame 145A, 145B, and 145C, respectively, of native-leaflet grasper 140A, 140B, and 140C, which may comprise one or more wires, which may be part of neo-leaflet wire loops 136A, 136B, and 136C, respectively, described above. Typically, the one or more biocompatible thin sheets of material are soft and atraumatic. The one or more biocompatible thin sheets of material may comprise a synthetic material or a biological tissue material, such as, for example, a fabric comprising of a polymer or biomaterial (e.g., polyethylene terephthalate (PET), expanded polytetrafluoroethylene (ePTFE), silicone, urethane, or pericardium).

For some applications, neo-leaflets 132A, 132B, and 132C are coupled to loop-shaped ventricular anchor 130 via native-leaflet graspers 140A, 140B, and 140C, respectively, such as shown in FIGS. 10A-F and 11A-D.

For some of these applications, such as shown in FIGS. 10A-F, anchor-loop wire loop 150 of loop-shaped ventricular anchor 130 is coupled to grasper covers 144A, 144B, and 144C of native-leaflet graspers 140A, 140B, and 140C, respectively, by passing through openings defined by grasper covers 144A, 144B, and 144C. This configuration allows pivoting and sliding of loop-shaped ventricular anchor 130 with respect to native-leaflet graspers 140A, 140B, and 140C, and thus with respect to neo-leaflets 132A, 132B, and 132C, respectively.

For others of these applications, such as shown in FIG. 11A-D, anchor-loop wire loop 150 of loop-shaped ventricular anchor 130 is coupled to frame 145C of native-leaflet grasper 140C. The anchor-loop wire loop is fixed (e.g., welded) to frame 145C, or may not be fixed to frame 145C, so as to allow pivoting and sliding of loop-shaped ventricular anchor 130 with respect to native-leaflet grasper 140C, and thus with respect to neo-leaflet 132C.

For some applications, each of native-leaflet graspers 140A, 140B, and 140C is shaped so as to define first and second portions 142A and 142B that are configured to grasp the atrial and the ventricular surfaces, respectively, of target native leaflet 26 by sandwiching at least a portion of atrial and ventricular surfaces 345 and 343 of target native leaflet 26 between the first and the second portions of the native-leaflet grasper. Typically, in these configurations, second portion 142B is defined by a proximal portion of anchor-loop wire loop 150, and first portion 142A is defined by frame 145A, 145B, and 145C, respectively, of native-leaflet graspers 140A, 140B, and 140C, which are part of neo-leaflet wire loops 136A, 136B, and 136C, respectively.

As mentioned above, optionally the one or more grasper covers 144A, 144B, and 144C extend across and partially or entirely occupy a space at least partially surrounded by frame 145A, 145B, and 145C, respectively (as shown). Typically, the grasper covers at these locations inflate from blood flow during a portion of the cardiac cycle and push against the ventricular surface of target native leaflet 26 to prevent blood flow between the target native leaflet and the coaptation-assist device.

Optionally, the one or more grasper covers 144A and 144B extend across and partially or entirely occupy a space at least partially surrounded by the proximal portion of anchor-loop wire loop 150 that defines second portion 142B (configuration not shown).

For some applications, such as shown in FIGS. 10A-C, neo-leaflet wire loop 136A narrows at a border 149 between neo-leaflet 132A and first portion 142A of native-leaflet grasper 140A. This narrowing may reduce interaction between the coaptation-assist device and the surrounding anatomy.

For other applications, such as shown in FIGS. 10D-F and 11A-D, neo-leaflet wire loops 136B and 136C do not narrow at border 149 between neo-leaflets 132B and 132C, respectively, and first portion 142A of native-leaflet grasper 140B and 140C. This lack of narrowing may provide a larger surface of contact between grasper covers 144B and 144C of native-leaflet graspers 140B and 140C, respectively, and ventricular surface 343 of target native leaflet 26, and/or better inflation of the grasper covers, than in the configuration shown in FIGS. 10A-C.

Reference is made to FIGS. 11A-D. For some applications, coaptation-assist device 120C further comprise a pouch 158, which is configured to inflate by blood flow during the cardiac cycle, so as to push coaptation-assist device 120C against the ventricular surface of target native leaflet 26 and/or the annulus of native valve 22, thereby stabilizing coaptation-assist device 120C with respect to native valve 22. For some applications, pouch 158 is defined by native-leaflet grasper 140C, such as by a ventricularly-facing surface of first portion 142A of native-leaflet grasper 140C (this ventricularly-facing surface is on the side of first portion 142A opposite the side of first portion 142A that is configured to come in contact with atrial surface 345 of target native leaflet 26). Optionally, the other coaptation-assist devices described herein, such as the native-leaflet graspers of the other coaptation-assist devices, comprise pouch 158, mutatis mutandis.

Reference is now made to FIGS. 12A-E and 13A-E, which are schematic illustrations of coaptation-assist devices 320A and 320B, respectively, in accordance with respective applications of the present invention. Other than as described hereinbelow, coaptation-assist devices 220A and 220B are generally similar to coaptation-assist device 20, described hereinabove with reference to FIGS. 1A-E and 2, and like reference numerals refer to like parts. Coaptation-assist devices 320A and 320B, including their respective neo-leaflets and loop-shaped ventricular anchors, may implement (a) any of the features of coaptation-assist device 20, mutatis mutandis, including the features described hereinabove with reference to FIGS. 3A-K and the features described hereinabove with reference to FIGS. 4A-B, and/or (b) any of the features of the other coaptation-assist devices described herein, mutatis mutandis.

Figure 15A:
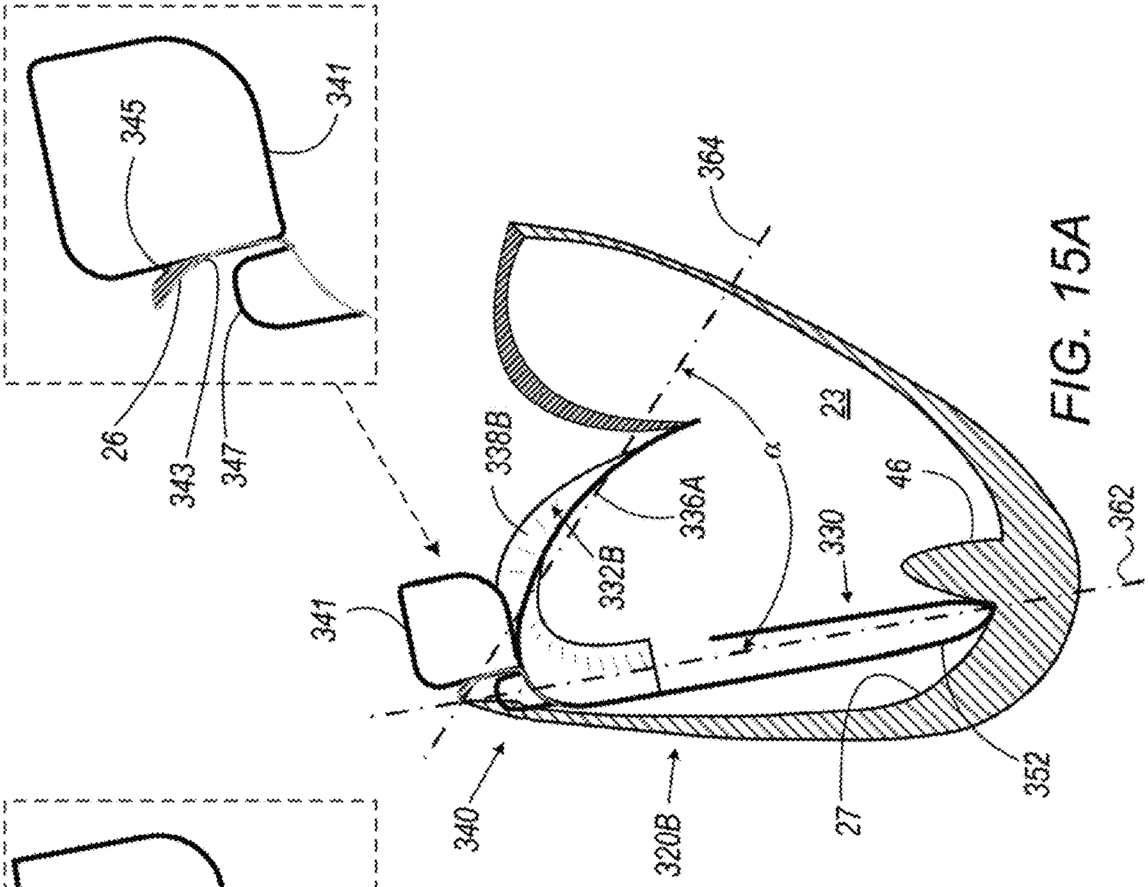
FIGS. 15A-B are schematic illustrations of the coaptation-assist device of FIGS. 13A-E implanted in a native valve, in accordance with an application of the present invention.
Figure 14:
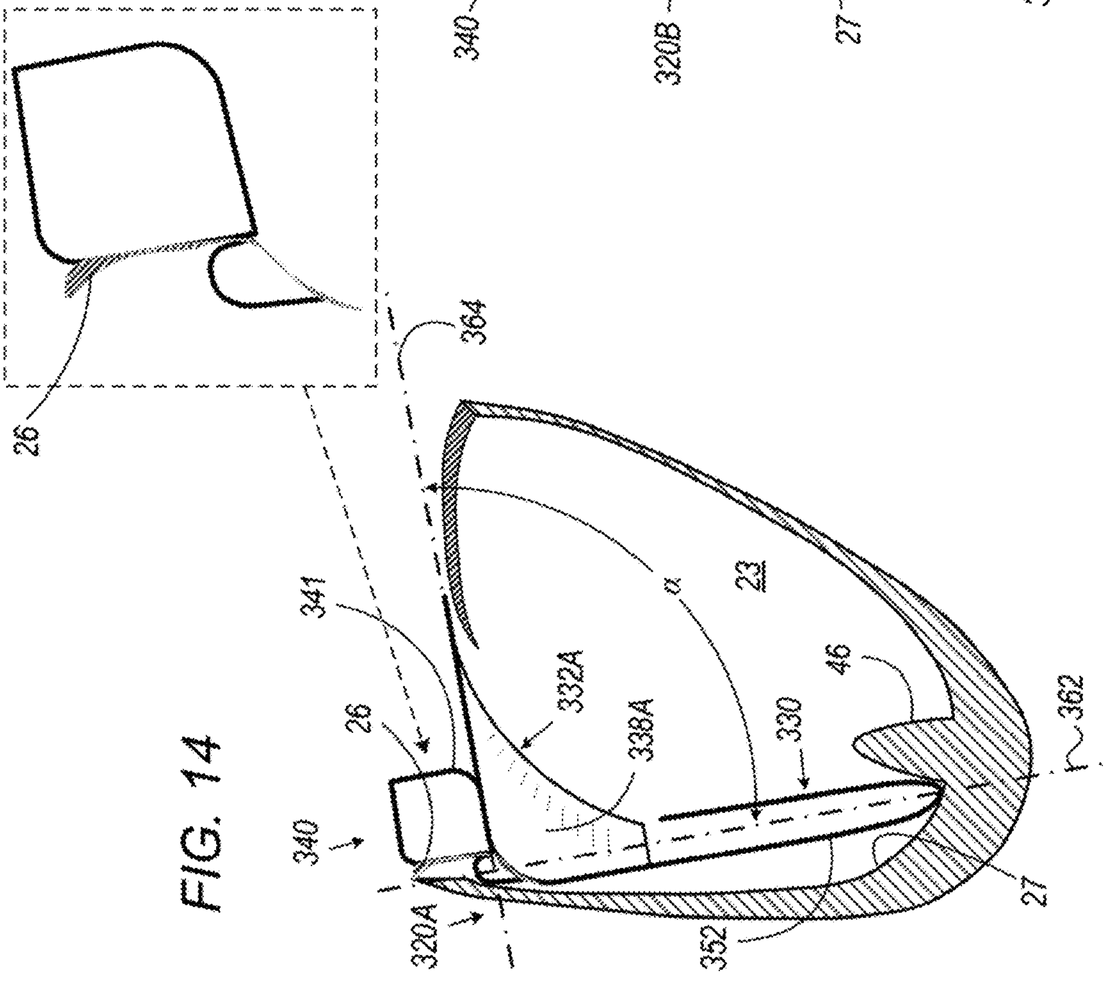
FIG. 14 is a schematic illustration of the coaptation-assist device of FIGS. 12A-E implanted in a native valve, in accordance with an application of the present invention.
Figure 15B:
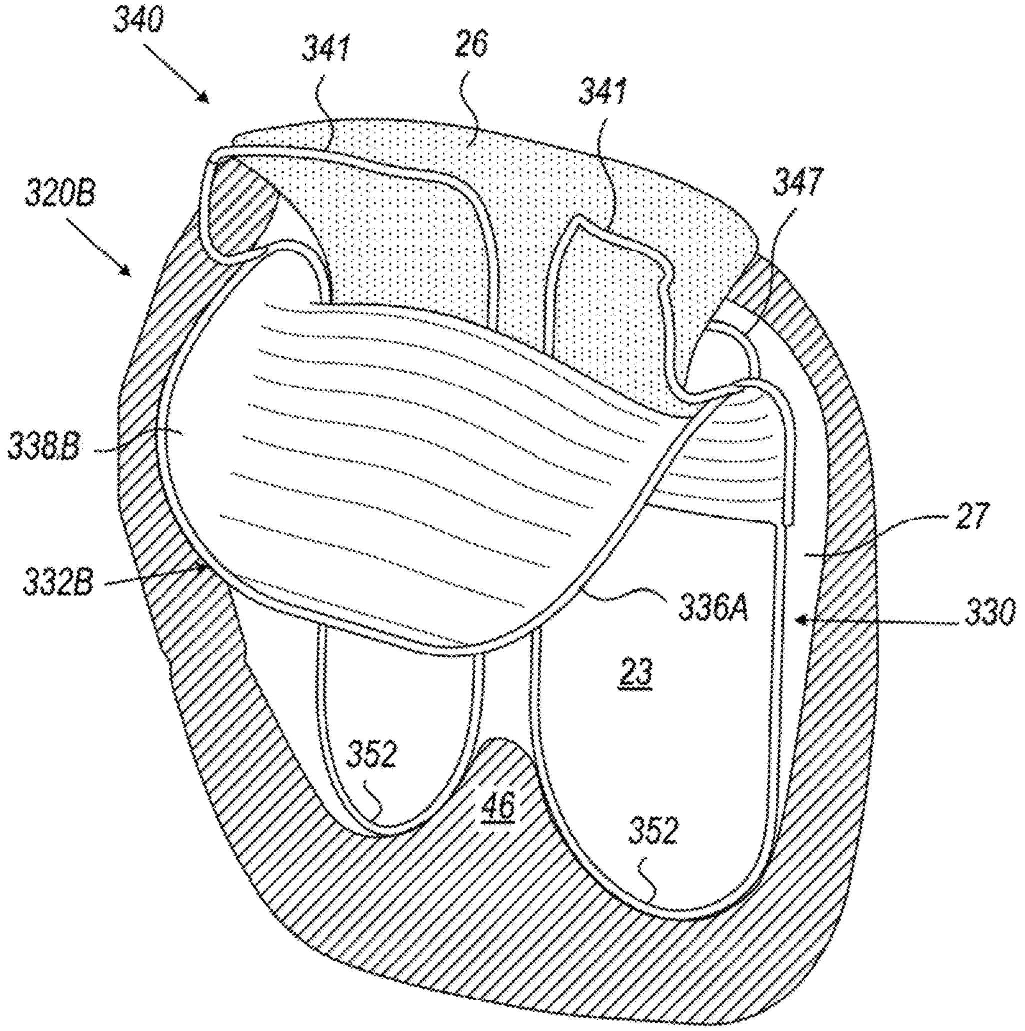

Reference is also made to FIGS. 14 and 15A-B, which are schematic illustrations of coaptation-assist devices 320A and 320B, respectively, implanted in native valve 22, in accordance with respective applications of the present invention.

Each of coaptation-assist devices 320A and 320B comprises a loop-shaped ventricular anchor 330, which typically comprises an anchor-loop wire loop 350 that defines at least a portion of a border of the loop-shaped ventricular anchor. Loop-shaped ventricular anchor 330 and anchor-loop wire loop 350 may implement any of the features of the loop-shaped ventricular anchors and anchor-loop wire loops described herein, mutatis mutandis. Coaptation-assist devices 320A and 320B further comprise neo-leaflets 332A and 332B, respectively, which may implement any of the features of the neo-leaflets described herein, mutatis mutandis. For some applications, neo-leaflets 332A and 332B comprise neo-leaflet wire loops 336A and 336B, respectively, which defines at least a portion of a border of the neo-leaflets, and neo-leaflet covers 338A and 338B attached to neo-leaflet wire loop 336A and 336B, respectively. Neo-leaflet wire loops 336A and 336B may implement any of the features of the neo-leaflet wire loops described herein, mutatis mutandis, and neo-leaflet covers 338A and 338B may implement any of the features of the neo-leaflet covers described herein, respectively mutatis mutandis.

Each of coaptation-assist devices 320A and 320B further comprises a native-leaflet grasper 340, which comprises one or more sub-native-leaflet supports 347 (such as two, as illustrated), which are configured to press against one or more portions of a ventricular surface 343 of target native leaflet 26 when loop-shaped ventricular anchor 330 is positioned in ventricle 23.

For some applications, each of neo-leaflets 332A and 332B extends directly from and is supported by loop-shaped ventricular anchor 330. Loop-shaped ventricular anchor 330 is disposed distally to each of neo-leaflets 332A and 332B.

For some applications, native-leaflet grasper 340 further comprises one or more supra-annular supports 341 (such as two, as illustrated), which are configured to press against an atrial surface 345 of target native leaflet 26, such that the one or more sub-native-leaflet supports 347 and the one or more supra-annular supports 341 sandwich and grasp target native leaflet 26 when loop-shaped ventricular anchor 330 is positioned in ventricle 23.

For some applications, loop-shaped ventricular anchor 330 is shaped so as to define two or more lobes 352, such as exactly two lobes 352 (as shown), such as to allow space for one of papillary muscles 46 between the two lobes when loop-shaped ventricular anchor 330 is positioned in ventricle 23. Alternatively, depending on the particular anatomy of the subject, which varies, the one or more lobes may allow space for other anatomical elements, such as one or more chordae tendineae, or no anatomical elements may utilize the provided space. Typically, the one or more lobes 352 extend to a distal end 354 of loop-shaped ventricular anchor 330. For some applications, ventricular wall 27 is a ventricular septal wall, and loop-shaped ventricular anchor 330 is configured to be remain anchored in position against the surrounding anatomy, including subannular surface 25, ventricular septal wall 27, and one or more ventricular papillary muscles 46 of ventricular apical area 24, when loop-shaped ventricular anchor 330 is positioned in ventricle 23.

For some applications, coaptation-assist devices 320A and 320B comprise respective wire loops that are shaped so as to at least partially define both (a) neo-leaflets 332A and 332B, respectively, and (b) loop-shaped ventricular anchor 330.

Reference is made to FIGS. 12D, 13C, 14, and 15A. For some applications, coaptation-assist devices 320A and 320B are configured such that when unconstrained (by application of any external forces, including by the anatomy or the delivery system), an angle $\alpha$ (alpha) is defined between (a) an anchor-loop best-fit plane 362 defined by anchor-loop wire loop 350 and (b) a neo-leaflet best-fit plane 364 defined by neo-leaflet wire loops 336A and 336B, respectively. Typically, coaptation-assist devices 320A and 320B are configured to automatically assume this angle: for example, elements of the devices may comprise a shape-memory alloy, such as Nitinol, which is configured to cause the device to assume this angle when in a resting, relaxed state, e.g., at 37 degrees Celsius (body temperature). Alternatively, neo-leaflet best-fit plane 364 is defined by coaptation surfaces of neo-leaflets 332A and 332B, respectively.

Figure 12A:
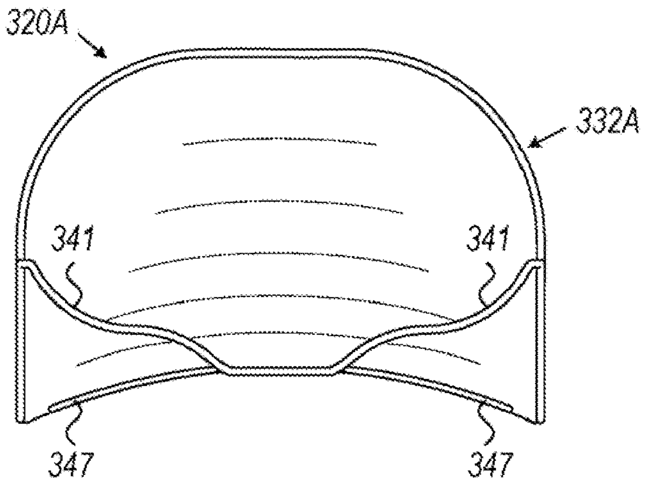
FIGS. 12A-E are schematic illustrations of still another coaptation-assist device, in accordance with an application of the present invention.
Figure 12B:
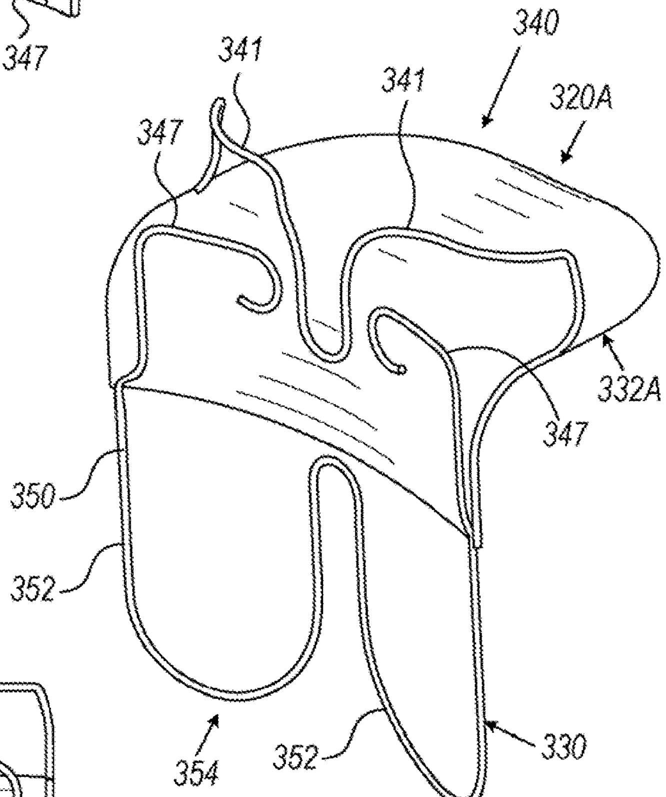
Figure 12C:
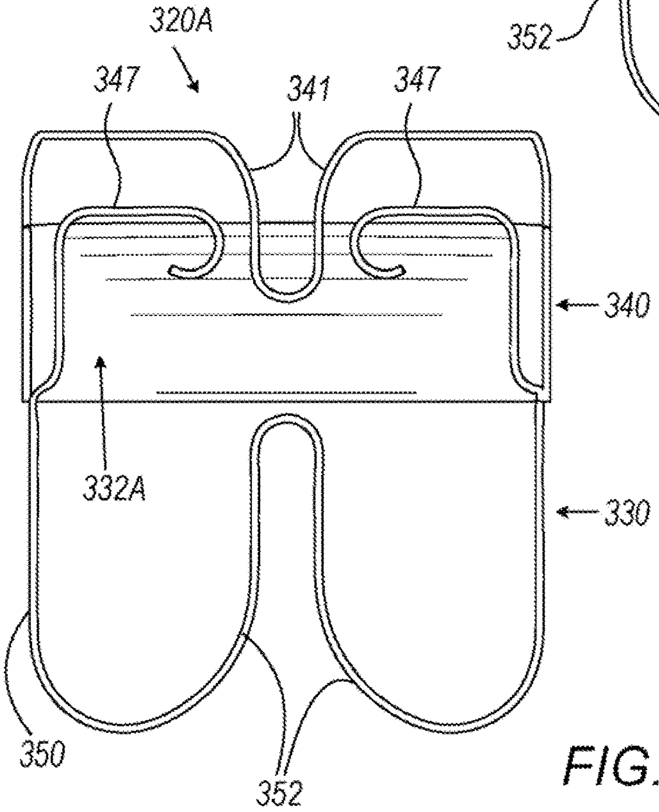
Figure 12D:
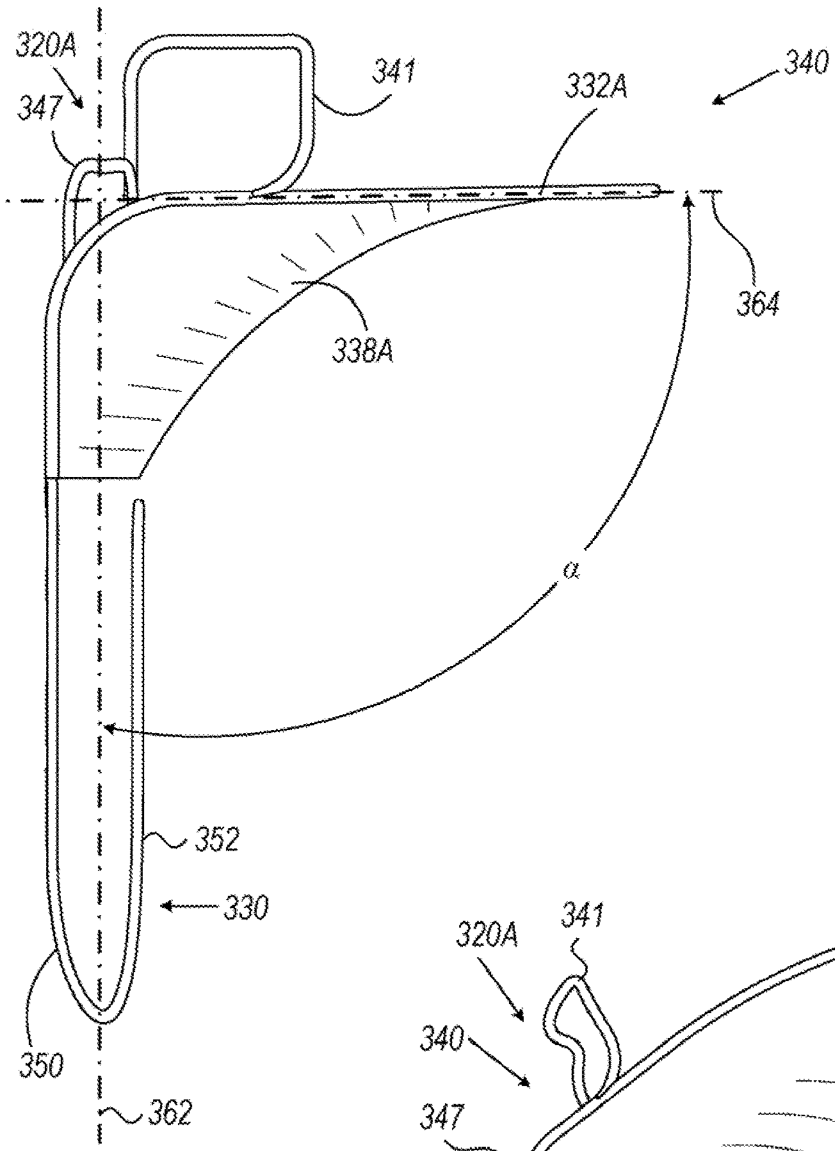
Figure 12E:
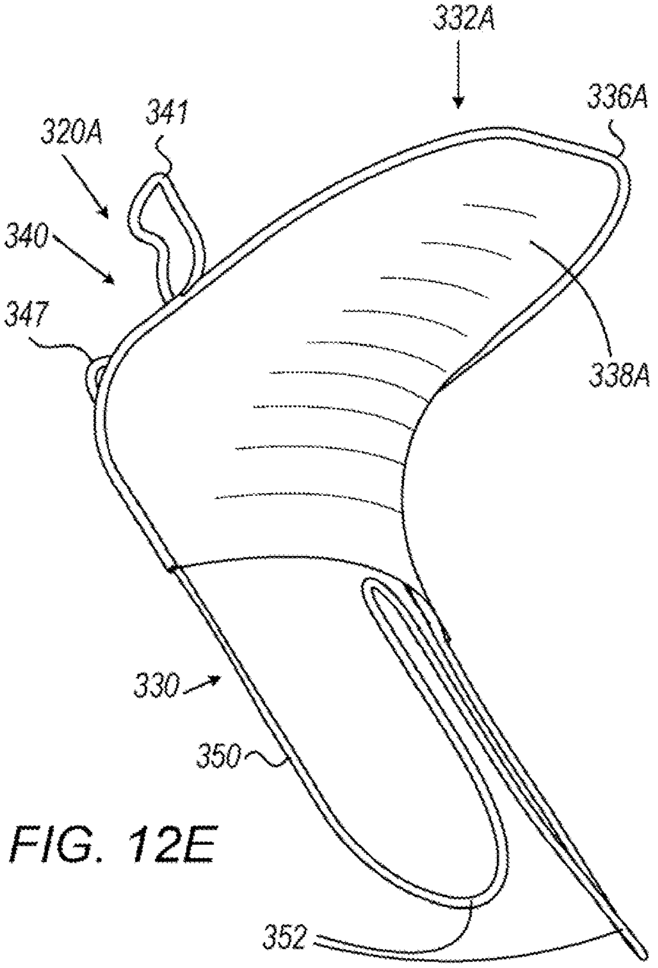

For some applications, such as shown in FIGS. 12D and 14, the angle $\alpha$ (alpha) is at least 60 degrees (e.g., at least 80 degrees), no more than 100 degrees (e.g., no more than 90 degrees), and/or between 60 degrees (e.g., 80 degrees) and 100 degrees (e.g., 90 degrees). This range of angles disposes neo-leaflet 332A above (superior to) the one or more opposing native leaflets 28, and therefore above the coaptation plane of the one or more opposing native leaflets 28 in systole and tendentially at the annulus level. As a result, the one or more opposing native leaflets 28 coapt against the ventricular surface of neo-leaflet 332A. This configuration is indicated in case the one or more opposing native leaflets 28 prolapse or flail, and particularly for mitral valve disease. The generally somewhat horizontal neo-leaflet 332A provides a surface of coaptation for the one or more opposing native leaflets 28 when they try to prolapse atrially or at the annular level.

Figure 13D:
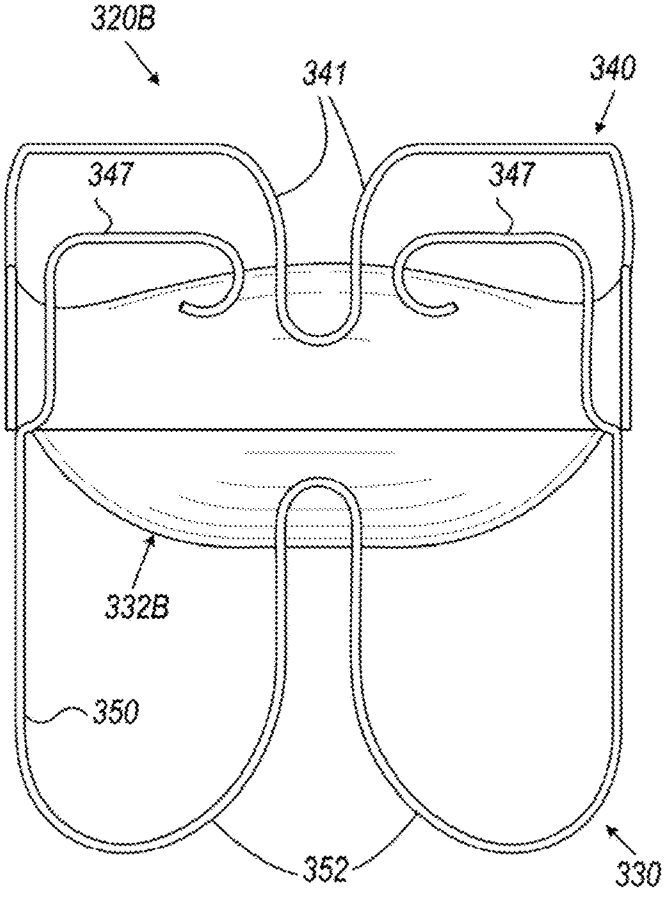
Figure 13C:
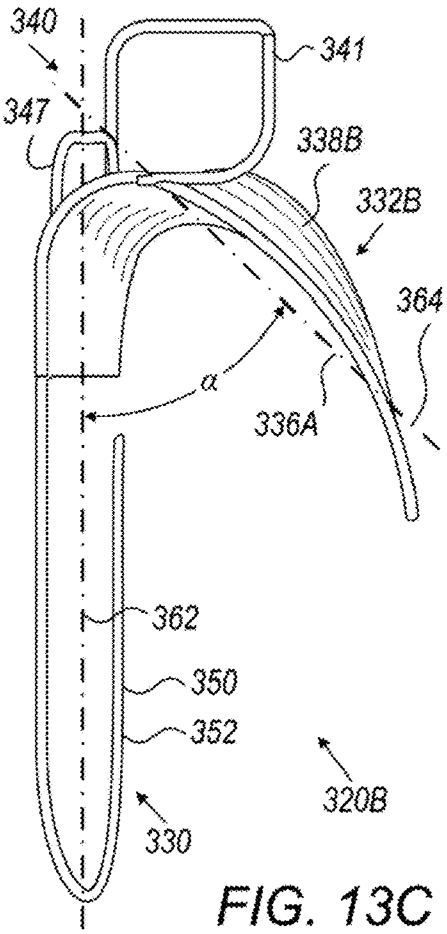
Figure 13E:
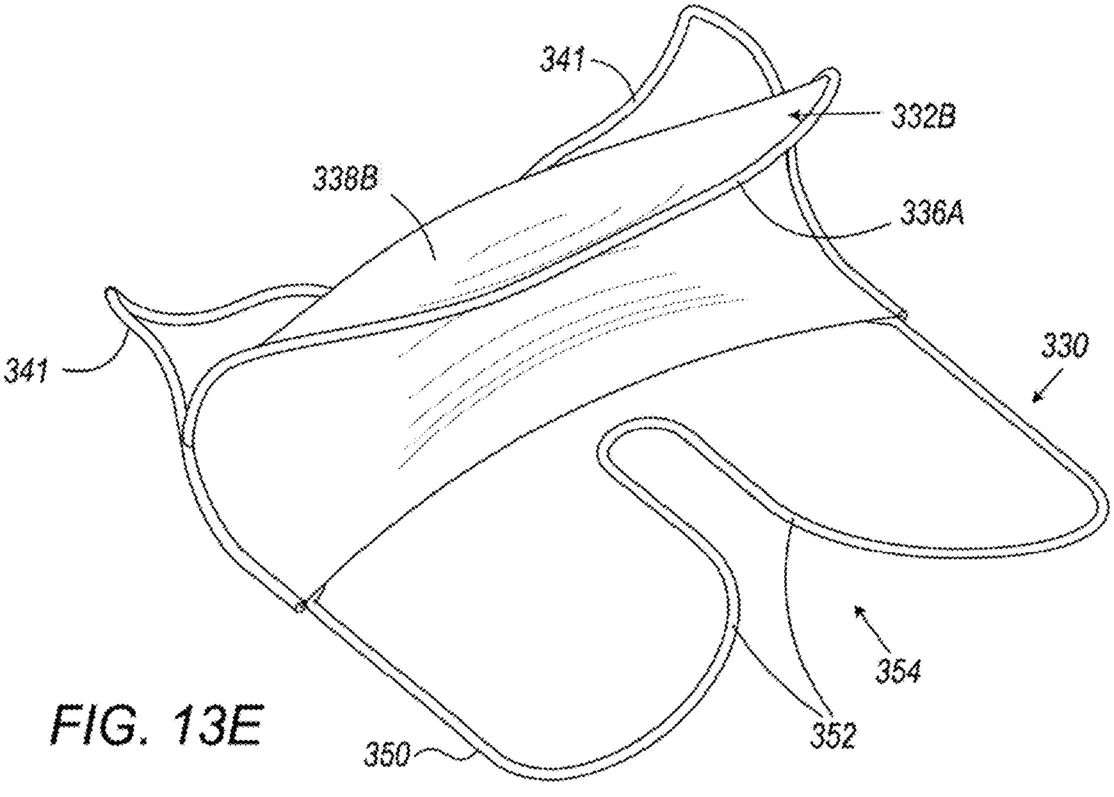

For other applications, such as shown in FIGS. 13C and 15A, the angle α (alpha) is at least 15 degrees (e.g., at least 35 degrees), no more than 50 degrees (e.g., no more than 45 degrees), and/or between 15 degrees (e.g., 35 degrees) and 50 degrees (e.g., 45 degrees). This range of angles disposes neo-leaflet 332B below the one or more opposing native leaflets 28, and therefore below their coaptation plane in systole, and tendentially with a tip of neo-leaflet 332B arriving ventricularly lower than the free edge(s) of the one or more opposing native leaflets 28 when in systole. This configuration is indicated in case of functional disease, with leaflets tethering and lack of leaflet coaptation, in both tricuspid and mitral diseases. In this configuration, coaptation-assist device 320B is configured such that a coaptation surface of neo-leaflet 332B crosses from an atrial side to a ventricular side of a native valvular plane, when loop-shaped ventricular anchor 330 is positioned in ventricle 23.

In either of these angular configurations, neo-leaflets 332A and 332B can be flexible or rigid, and may optionally move (open/close) with the heart beat in order to be effective.

Reference is now made to FIGS. 16A-F, which are schematic illustrations of a coaptation-assist device 420, in accordance with an application of the present invention. Other than as described hereinbelow, coaptation-assist device 420 is generally similar to coaptation-assist device 20, described hereinabove with reference to FIGS. 1A-E and 2. Coaptation-assist device 420, including its neo-leaflet and loop-shaped ventricular anchor, may implement (a) any of the features of coaptation-assist device 20, mutatis mutandis, including the features described hereinabove with reference to FIGS. 3A-K and the features described hereinabove with reference to FIGS. 4A-B, and/or (b) any of the features of the other coaptation-assist devices described herein, mutatis mutandis.

Figure 17:
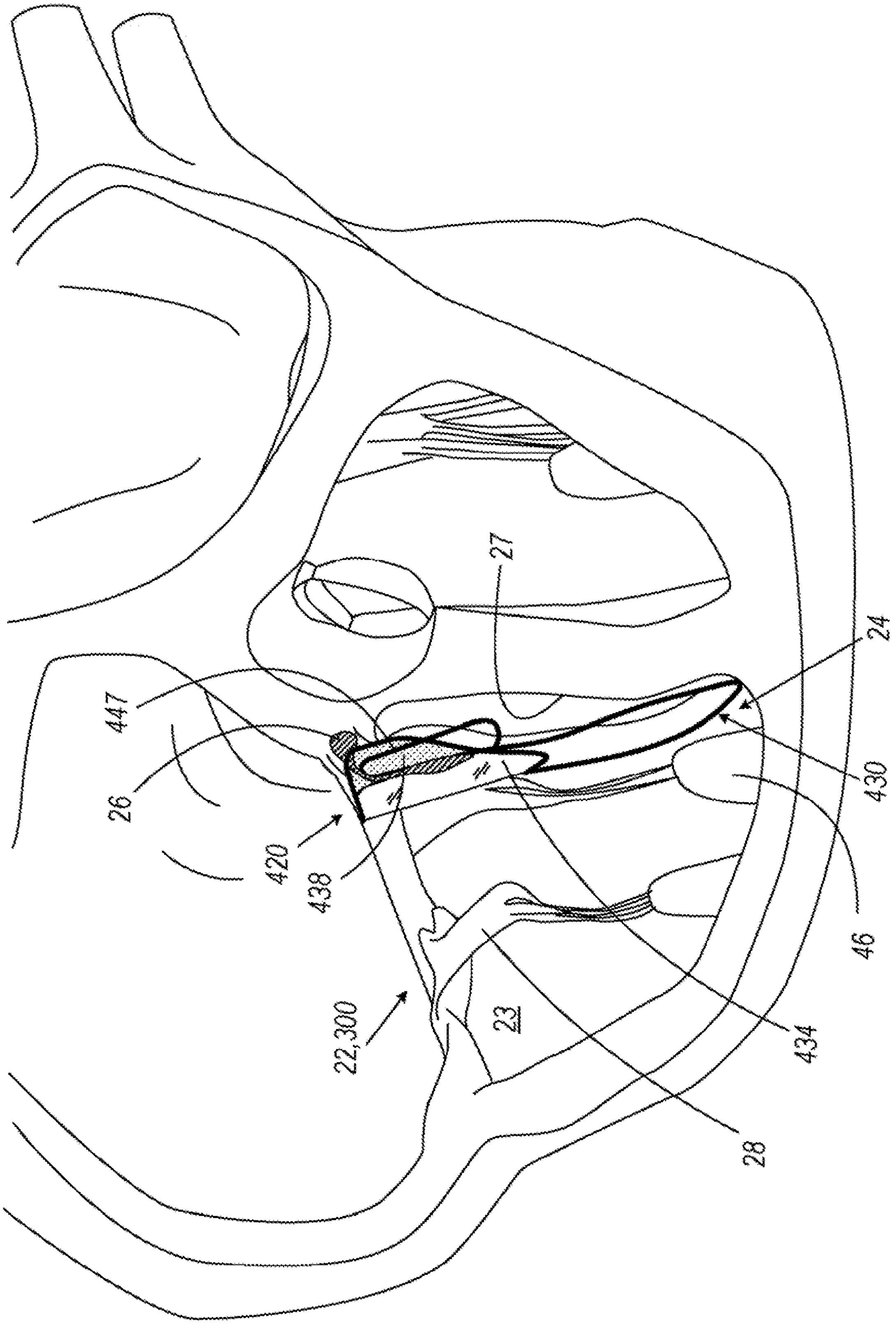
FIG. 17 is a schematic illustration of the coaptation-assist device of FIGS. 16A-F implanted in a native valve, in accordance with an application of the present invention.
Figure 19:
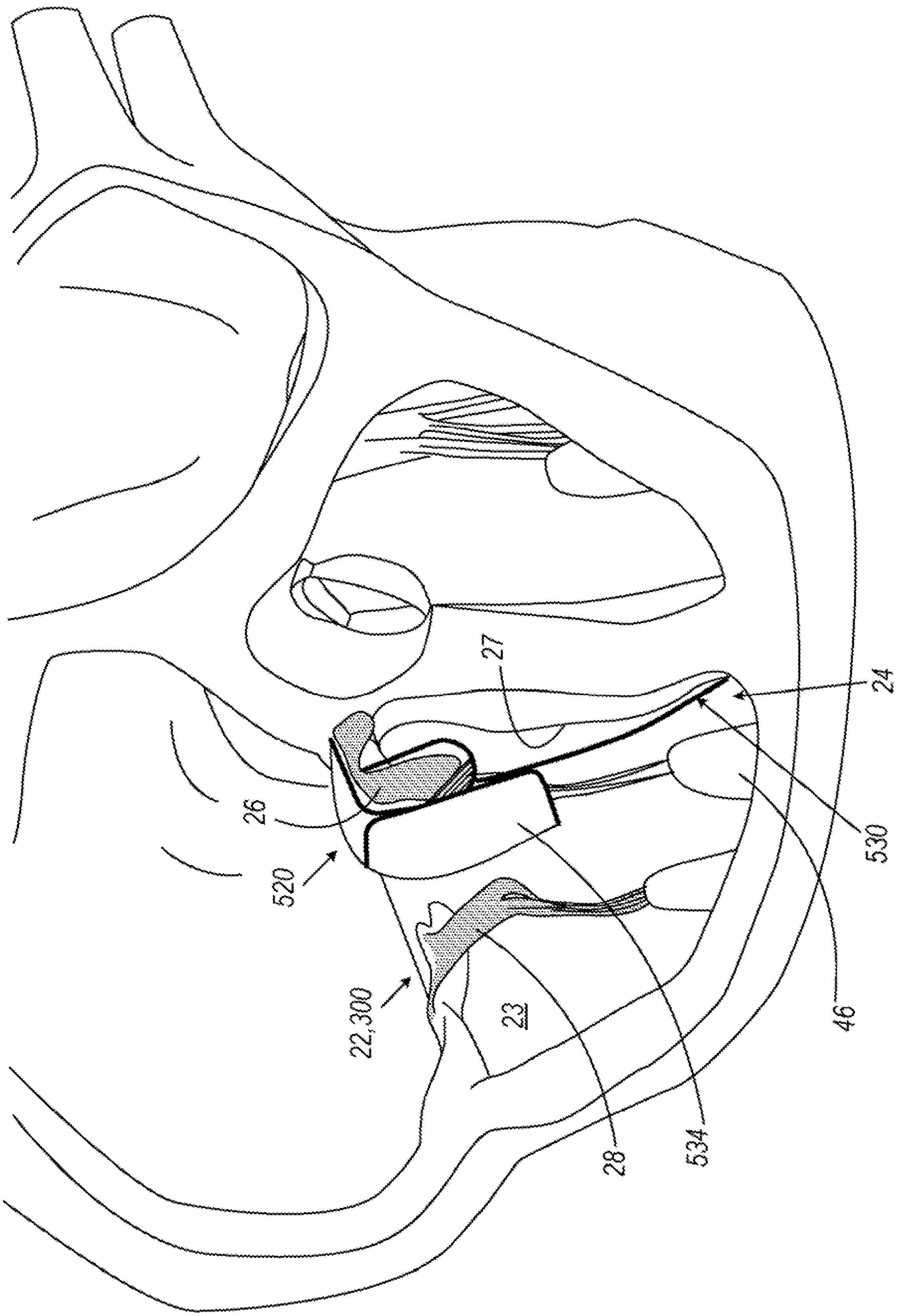
FIG. 19 is a schematic illustration of the coaptation-assist device of FIGS. 18A-F implanted in a native valve, in accordance with an application of the present invention.

Reference is additionally made to FIG. 17, which is a schematic illustration of coaptation-assist device 620 implanted in native valve 22, in accordance with an application of the present invention. In the particular implantation shown in FIG. 17, native valve 22 is the tricuspid valve. FIG. 19 is a cross-sectional view of the heart, with an anterior portion of the heart, including the native anterior leaflet of the tricuspid valve, removed, such that only the septal and posterior leaflets are shown.

Coaptation-assist device 420 comprises a loop-shaped ventricular anchor 430, which typically comprises an anchor-loop wire loop 450 that defines at least a portion of a border of the loop-shaped ventricular anchor. Loop-shaped ventricular anchor 430 and anchor-loop wire loop 450 may implement any of the features of the loop-shaped ventricular anchors and anchor-loop wire loops described herein, mutatis mutandis.

For some applications, anchor-loop wire loop 450, such as at least 50% (e.g., at least 75%) of a length of anchor-loop wire loop 450, measured around anchor-loop wire loop 450, is shaped so as to define a distal generally round portion. For other applications, anchor-loop wire loop 450 has another shape, such as any of the shapes of the loop-shaped ventricular anchors (and, typically, anchor-loop wire loops) described herein.

Coaptation-assist device 420 further comprises a neo-leaflet 432, which may implement any of the features of the neo-leaflets described herein, mutatis mutandis. Loop-shaped ventricular anchor 430 is disposed distally to neo-leaflet 432. For some applications, neo-leaflet 432 comprises a neo-leaflet wire loop 436, which defines at least a portion of a border of the neo-leaflet, and a neo-leaflet cover 438 attached to neo-leaflet wire loop 436. (For clarity of illustration, in FIG. 16B coaptation-assist device 420 is shown without neo-leaflet cover 438, as well as without grasper cover 444, described hereinbelow.) Neo-leaflet wire loop 436 may implement any of the features of the neo-leaflet wire loops described herein, mutatis mutandis, and neo-leaflet cover 438 may implement any of the features of the neo-leaflet covers described herein, respectively mutatis mutandis.

For some applications, neo-leaflet 432 is curved in a shield-shape to accommodate better the annular area at the target native leaflet level. This shield shape may also provide a coaptation surface 434 that is easy to reach for one or more opposing native leaflets 28.

Coaptation-assist device 420 further comprises a native-leaflet grasper 440, which is shaped so as to define first and second portions 442A and 442B that are configured to grasp atrial and ventricular surfaces 345 and 343, respectively, of target native leaflet 26 by sandwiching at least a portion of the atrial and the ventricular surfaces of target native leaflet 26 between the first and the second portions of native-leaflet grasper 440.

For some applications, second portion 442B of native-leaflet grasper 440 comprises one or more sub-native-leaflet supports 447 (such as two, as illustrated), which are configured to press against one or more portions of ventricular surface 343 of target native leaflet 26 when anchor-loop wire loop 450 is positioned in ventricle 23. For some applications, sub-native-leaflet supports 447 extend from the wire of anchor-loop wire loop 450, which narrows in a proximal direction. Optionally, proximal-most portions of sub-native-leaflet supports 447 are at approximately the same height as proximal-most portions of neo-leaflet 432.

Figure 16E:
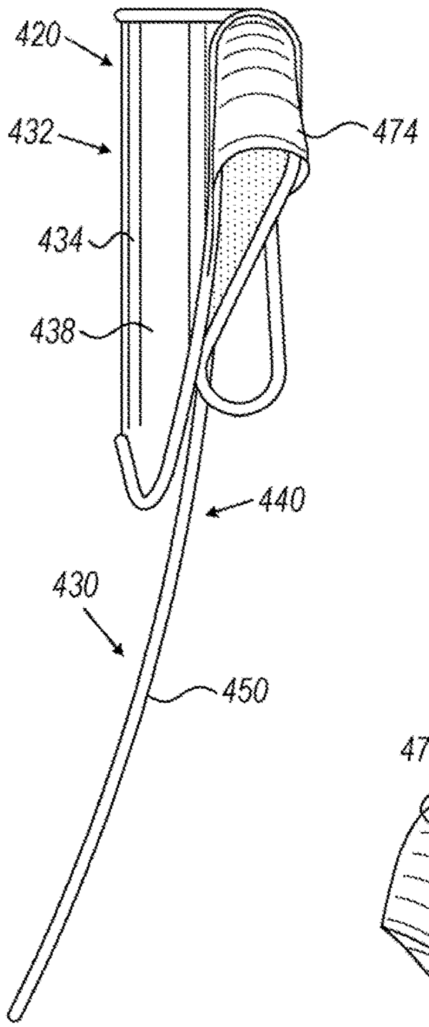
Figure 16F:
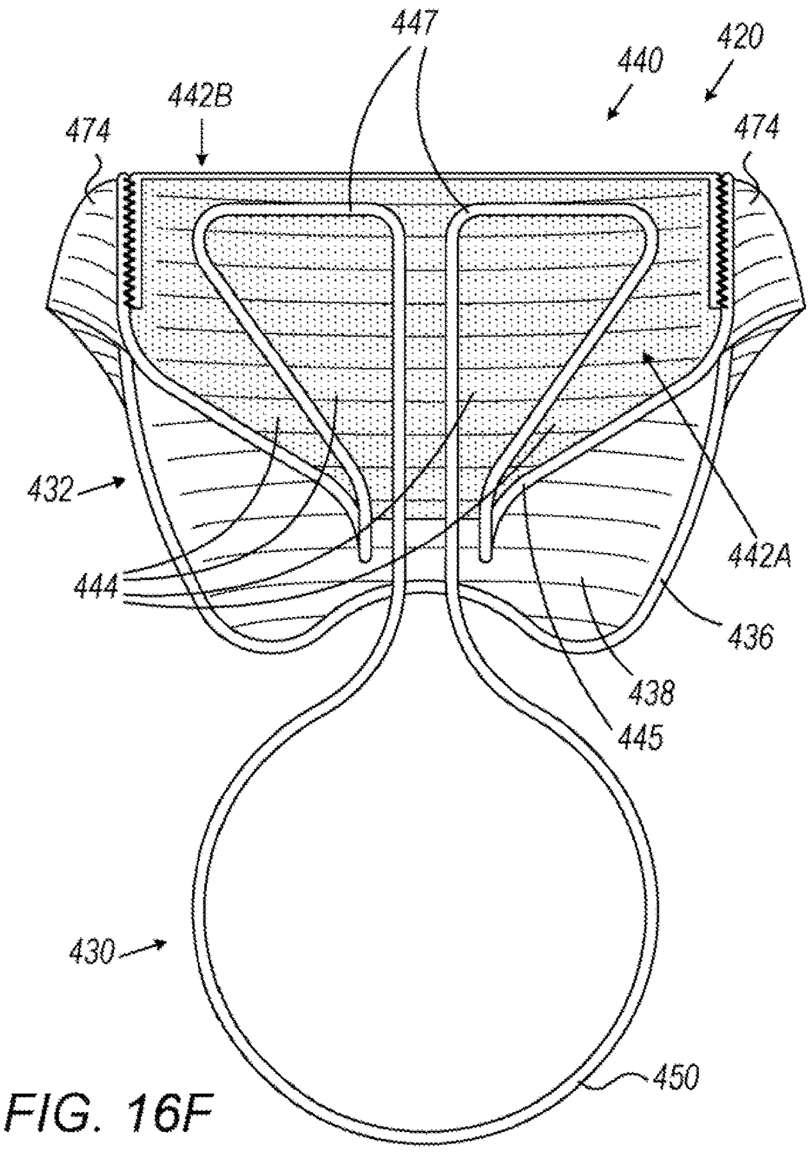

For some applications, first portion 442A of native-leaflet grasper 440 comprises a grasper cover 444, which is disposed between neo-leaflet cover 438 and the one or more sub-native-leaflet supports 447. Typically, grasper cover 444 pushes against atrial surface 345 of target native leaflet 26 to prevent blood flow between the target native leaflet and the coaptation-assist device. For some of these applications, grasper cover 444 extends across and partially or entirely occupies a space at least partially surrounded by a frame 445 of native-leaflet grasper 440, which may comprise one or more wires, which may be part of the wire loop described herein. (The shading of grasper cover 444 in FIGS. 16E and 16F is for clarity of illustration, and does not imply that grasper cover 444 comprises a separate piece of material from neo-leaflet cover 438 or a different type of material from that of neo-leaflet cover 438, although it could.)

For some applications, neo-leaflet 432 is coupled to loop-shaped ventricular anchor 430 via sub-native-leaflet supports 447 and optionally one or more additional wire portions.

For some applications, coaptation-assist device 420 comprises a coaptation-assist-device wire loop that is shaped so as to at least partially define (a) neo-leaflet 432, (b) anchor-loop wire loop 450, (c) optionally, the one or more sub-native-leaflet supports 447, and (d) optionally, frame 445 of native-leaflet grasper 440.

For some applications, coaptation-assist device 420 (e.g., neo-leaflet cover 438) comprises one or more (e.g., two) commissural pouches or parachutes 474, which are configured to inflate and relax along the blood flow and pressure variation, in a similar manner to pouch 158, described hereinabove with reference to FIGS. 11A-D, and/or the flexible parachute-like coaptation surfaces described hereinabove. Pouches 474 in FIGS. 16A-D originate at the same level on neo-leaflet wire loop 436 and frame 445, so as to have an even free edge of each pouch 474. Pouches 474 in FIGS. 16E-F originate lower (closer to the neo-leaflet tip) on neo-leaflet wire loop 436 than on frame 445, so as to create an uneven free edge of each pouch 474. This difference in attachment points results in a higher surface of pouch 474 in FIGS. 16E-F than in FIGS. 16A-D, such that the pouch is able to inflate more and cover a higher tridimensional surface when inflated. A higher surface can lead to better commissural area filling, with a consequent reduction in blood regurgitation in that area.

Reference is now made to FIGS. 18A-F, which are schematic illustrations of a coaptation-assist device 520 for treating native valve 22, in accordance with an application of the present invention. The native valve is typically an atrioventricular valve, i.e., the tricuspid or the mitral valve. For clarity of illustration, FIG. 18B does not show neo-leaflet cover 538 or grasper cover 544, described hereinbelow, even though coaptation-assist device 520 typically comprises these elements.

Reference is additionally made to FIG. 19, which is a schematic illustration of coaptation-assist device 520 implanted in native valve 22, in accordance with an application of the present invention. In the particular implantation shown in FIG. 19, native valve 22 is the tricuspid valve. FIG. 19 is a cross-sectional view of the heart, with an anterior portion of the heart, including the native anterior leaflet of the tricuspid valve, removed, such that only the septal and posterior leaflets are shown. Other than as described below, coaptation-assist device 520 is similar to the coaptation-assist devices described hereinabove, and may implement any of the features thereof, mutatis mutandis.

Coaptation-assist device 520 comprises a loop-shaped ventricular anchor 530 and a neo-leaflet 532, which extends directly from and is supported by loop-shaped ventricular anchor 530. Loop-shaped ventricular anchor 530 is disposed distally to neo-leaflet 532.

Typically, loop-shaped ventricular anchor 530 comprises an anchor-loop wire loop 550 that defines at least a portion of a border of loop-shaped ventricular anchor 530. Anchor-loop wire loop 550 may implement any of the features of anchor-loop wire loop 50, described hereinabove with reference to FIGS. 1A-E and 2, mutatis mutandis.

Anchor-loop wire loop 550 is configured (a) to be positioned in ventricle 23, extending to ventricular apical area 24, and (b) to remain anchored in position against surrounding anatomy, including ventricular apical area 24 (optionally including one or more ventricular papillary muscles 46 of ventricular apical area 24). In other words, anchor-loop wire loop 550 is configured to be seated apically. Optionally, the surrounding anatomy against which anchor-loop wire loop 550 is anchored further includes one or more of the following: a moderator band, one or more chordae tendineae, and one or more papillary muscles on the opposite side of ventricle 23.

Typically, coaptation-assist device 520 is configured such that when anchor-loop wire loop 550 is positioned in ventricle 23, anchor-loop wire loop 550 does not extend to (and therefore does not touch) subannular surface 25 of a target native leaflet 26 of native valve 22. Typically, positioning loop-shaped ventricular anchor 530 in ventricle 23 comprises positioning loop-shaped ventricular anchor 530 in ventricle 23 such that anchor-loop wire loop 550 does not extend to (and therefore does not touch) subannular surface 25 of a target native leaflet 26 of native valve 22.

For some applications, coaptation-assist device 520 does not comprise any elements that are configured to penetrate (e.g., pierce) tissue. For other applications, coaptation-assist device 520 comprises at least one element that is configured to penetrate tissue, such as described hereinbelow with reference to FIGS. 20A-B.

Neo-leaflet 532 is configured to at least partially replace function of target native leaflet 26 of native valve 22 by providing a surface of coaptation 534 for one or more opposing native leaflets 28 that oppose target native leaflet 26, when anchor-loop wire loop 550 is positioned in ventricle 23.

For some applications, neo-leaflet 532 comprises a neo-leaflet wire loop 536 that defines at least a portion of a border of the neo-leaflet, and a neo-leaflet cover 538, which is attached to neo-leaflet wire loop 536 and provides coaptation surface 534. Neo-leaflet wire loop 536 and neo-leaflet cover 538 may implement any features of neo-leaflet wire loop 36 and neo-leaflet cover 38, respectively, described hereinabove with reference to FIGS. 1A-E and 2, mutatis mutandis.

Typically, anchor-loop wire loop 550 is configured to remain anchored in position by force (typically radially-outwardly-directed force) applied by anchor-loop wire loop 550 to the surrounding anatomy, and/or by friction between anchor-loop wire loop 550 and the surrounding anatomy. For some applications, anchor-loop wire loop 550 comprises a self-expandable material, such as a shape-memory alloy (e.g., Nitinol) that causes the anchor-loop wire loop 550 to expand radially outwardly so as to apply the force. For these applications, anchor-loop wire loop 550 typically is configured to have a shape in its resting (relaxed) state that is larger than the surrounding anatomy, such that the surrounding anatomy limits expansion of anchor-loop wire loop 550 and anchor-loop wire loop 550 applies a force to the surrounding anatomy (and vice versa).

Typically, loop-shaped ventricular anchor 530 is configured to be atraumatic so as not to penetrate tissue of the surrounding anatomy.

For some applications, coaptation-assist device 520 further comprises a native-leaflet grasper 540, which is shaped so as to define first and second portions 542A and 542B that are configured to grasp atrial and ventricular surfaces 345 and 343, respectively, of target native leaflet 26 by sandwiching at least a portion of the atrial and the ventricular surfaces of target native leaflet 26 between the first and the second portions of native-leaflet grasper 540, in order to support neo-leaflet 532, and to orient neo-leaflet 532 with respect to native valve 22.

For some applications, native-leaflet grasper 540 is coupled to loop-shaped ventricular anchor 530 via neo-leaflet 532, such as shown.

For some applications, second portion 542B of native-leaflet grasper 540 comprises one or more sub-native-leaflet supports 547, which are configured to press against one or more portions of the ventricular surface of target native leaflet 26 when anchor-loop wire loop 550 is positioned in ventricle 23.

Figure 18A:
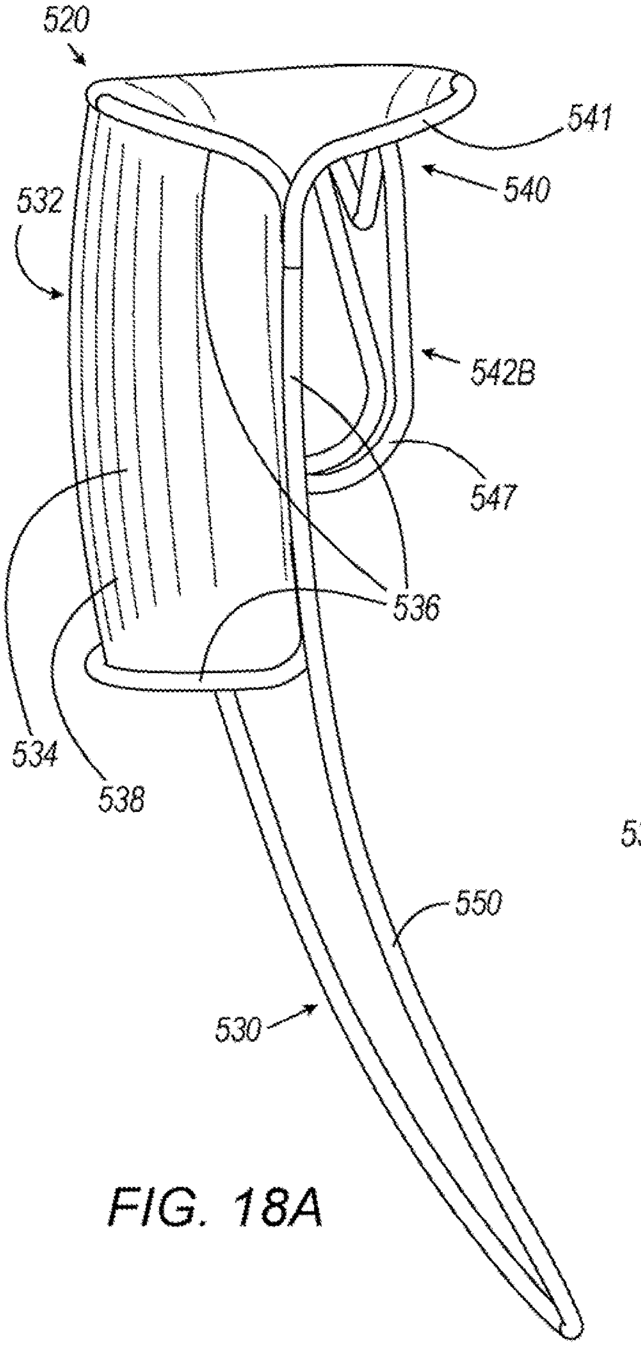
FIGS. 18A-F are schematic illustrations of another coaptation-assist device, in accordance with an application of the present invention.
Figure 18B:
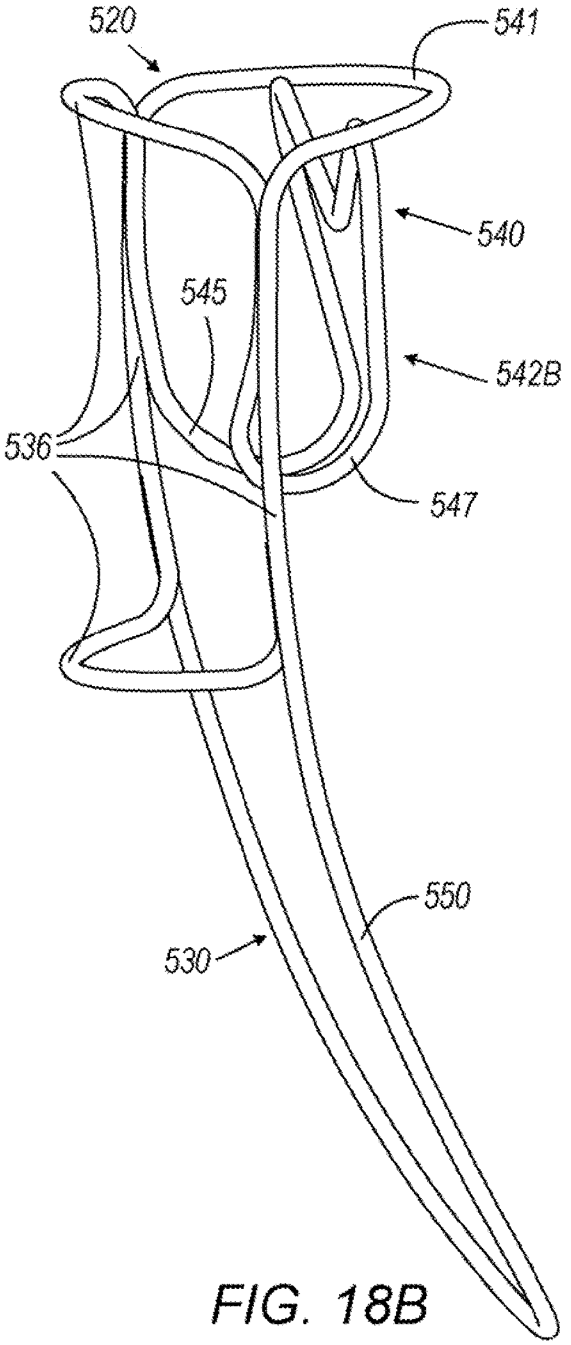
Figure 18D:
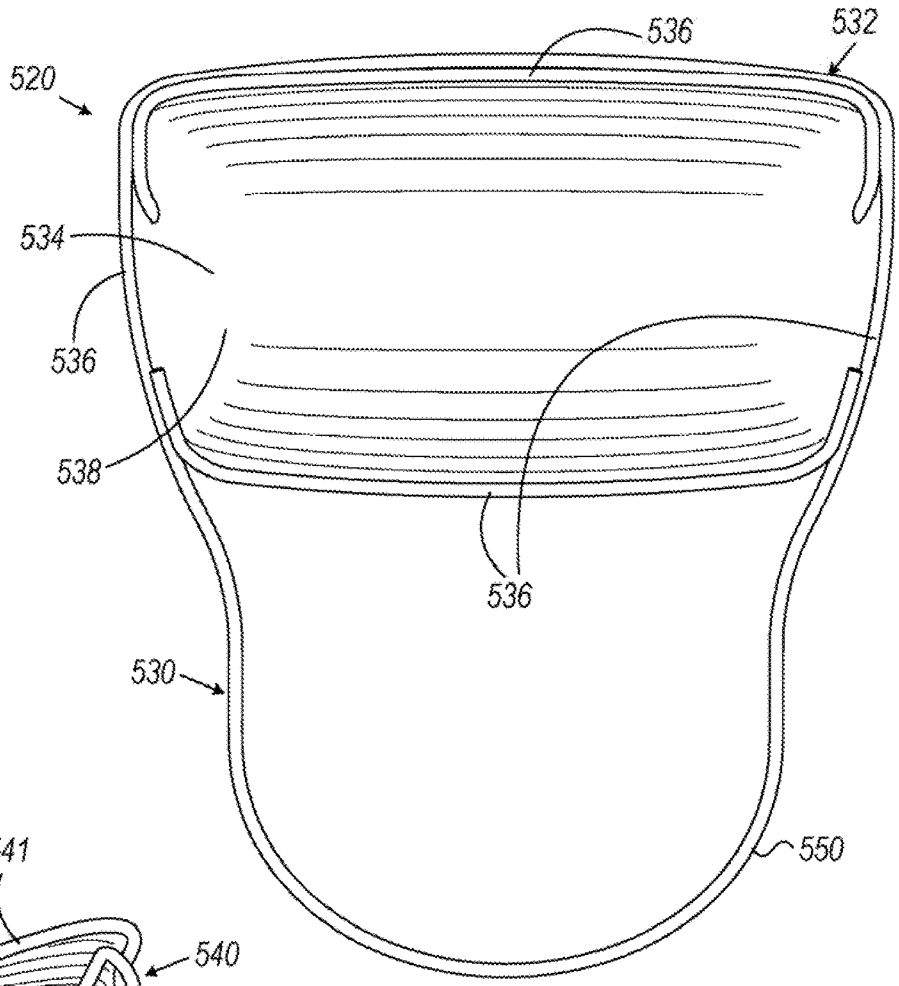
Figure 18C:
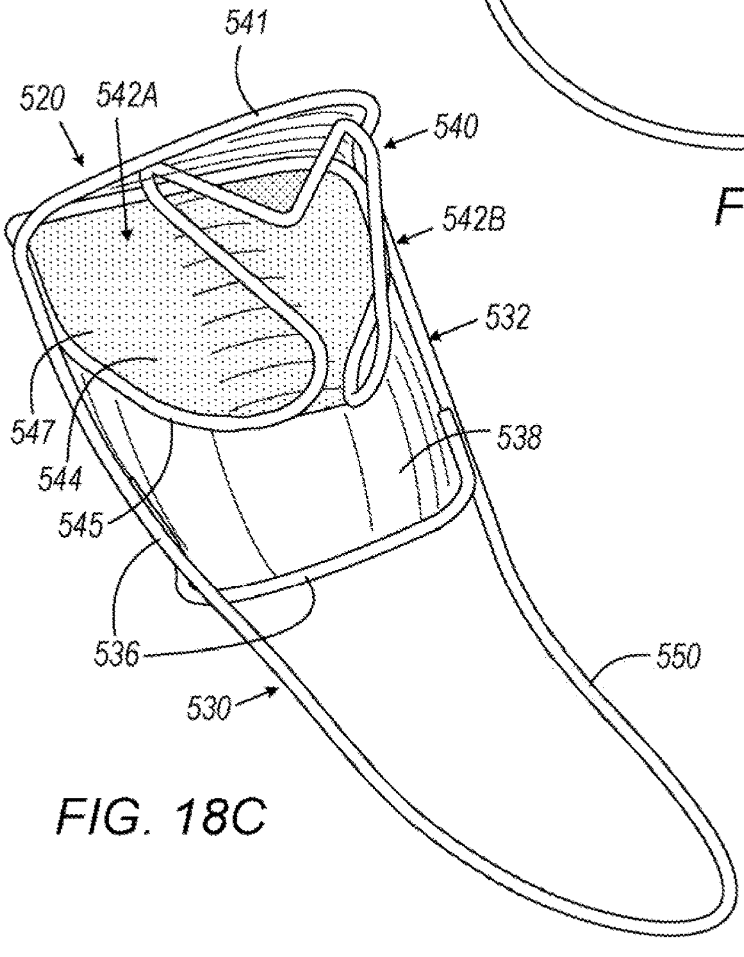
Figure 18E:
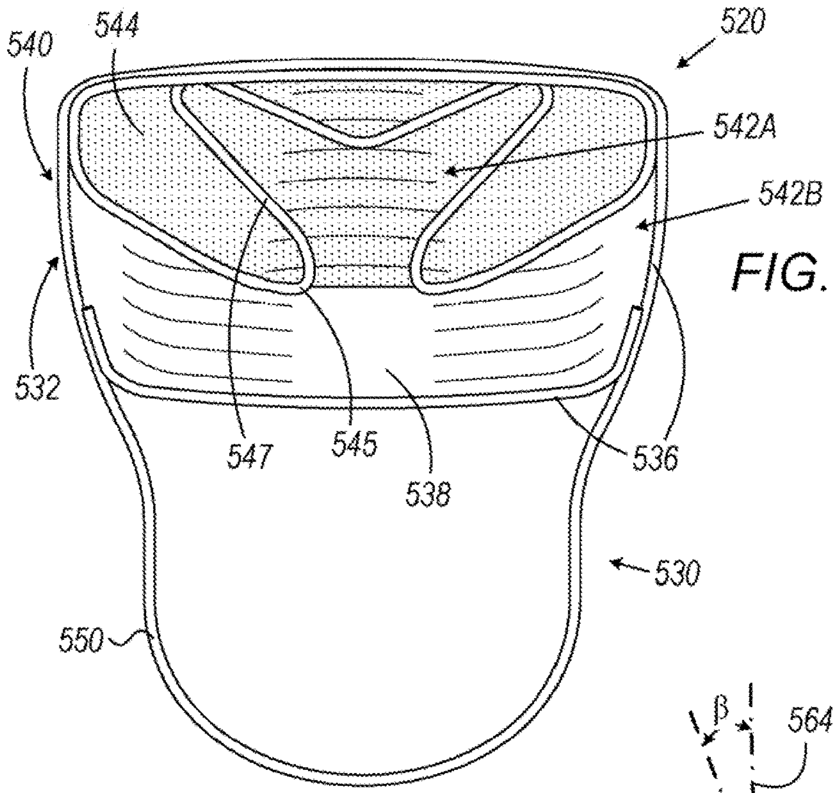
Figure 18F:
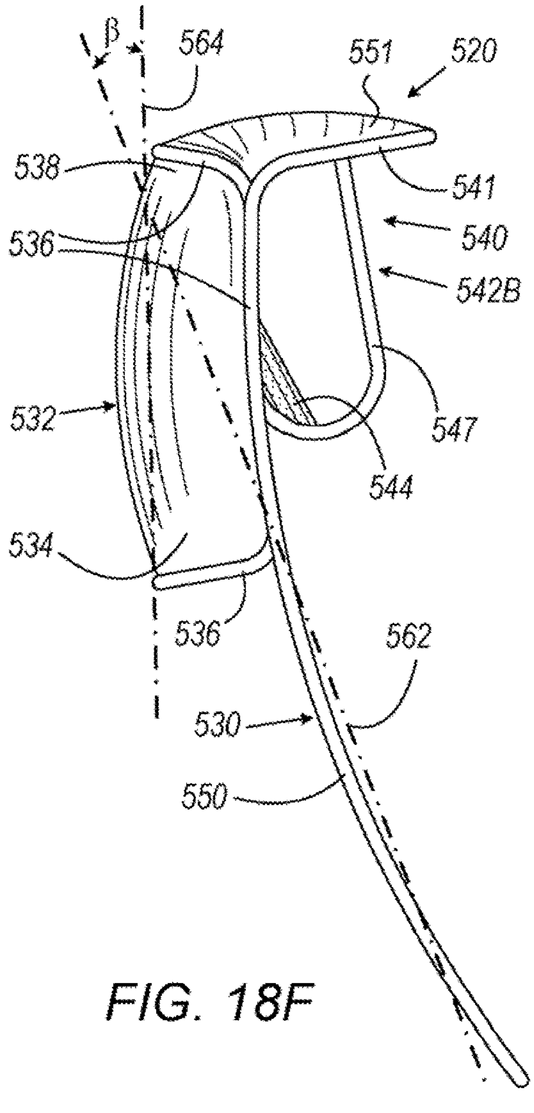

For some applications, first portion 542A of native-leaflet grasper 540 comprises a grasper cover 544, which is disposed between neo-leaflet cover 538 and the one or more sub-native-leaflet supports 547. Typically, grasper cover 544 pushes against atrial surface 345 of target native leaflet 26 to prevent blood flow between the target native leaflet and the coaptation-assist device. For some of these applications, grasper cover 544 extends across and partially or entirely occupies a space at least partially surrounded by a frame 545 of native-leaflet grasper 540, which may comprise one or more wires, which may be part of the wire loop described herein. (The shading of grasper cover 544 in FIGS. 18C, 18E, and 18F is for clarity of illustration, and does not imply that grasper cover 544 comprises a separate piece of material from neo-leaflet cover 538 or a different type of material from that of neo-leaflet cover 538, although it could.)

For some applications, native-leaflet grasper 540 further comprises one or more native-annulus supports 541, which are configured to further support neo-leaflet 532 against the native annulus. Optionally, native-leaflet grasper 540 further comprises a native-annulus-support cover 551 (labeled in FIG. 18F), which partially or entirely occupies a space at least partially surrounded by the one or more native-annulus supports 541, and provides additional sealing to prevent blood flow between the target native leaflet and the coaptation-assist device. For some applications, the one or more native-annulus supports 541 extend from neo-leaflet wire loop 536 in a direction opposite from the direction in which coaptation surface 534 points.

Typically, coaptation-assist device 520 is configured such that when anchor-loop wire loop 550 is positioned in ventricle 23 and native-leaflet grasper 540 grasps atrial and ventricular surfaces 345 and 343, respectively, of target native leaflet 26, anchor-loop wire loop 550 does not extend to (and therefore does not touch) subannular surface 25 of a target native leaflet 26 of native valve 22.

For some applications, anchor-loop wire loop 550 is configured to remain anchored in position against one or more ventricular papillary muscles 46 of ventricular apical area 24, when anchor-loop wire loop 550 is positioned in ventricle 23.

For some applications, coaptation-assist device 520 comprises a coaptation-assist-device wire loop that is shaped so as to at least partially define neo-leaflet wire loop 536 and anchor-loop wire loop 550.

Typically, anchor-loop wire loop 550 is larger than neo-leaflet wire loop 536.

For some applications, anchor-loop wire loop 550 is more flexible than neo-leaflet wire loop 536 (for example, by comprising thinner wires).

For some applications, anchor-loop wire loop 550 is generally flat, and neo-leaflet wire loop 536 is shaped so as to defined a curved coaptation surface 534.

Reference is made to FIG. 18F. For some applications, coaptation-assist device 520 is configured such that when unconstrained (by application of any external forces, including by the anatomy or the delivery system), an angle β (beta) is defined between (a) an anchor-loop best-fit plane 562 defined by anchor-loop wire loop 550 and (b) a neo-leaflet best-fit plane 564 defined by coaptation surface 534 of neo-leaflet 532. Typically, the angle β (beta) is less than 20 degrees. Alternatively, anchor-loop best-fit plane 562 and neo-leaflet best-fit plane 564 are parallel with each other. Typically, coaptation-assist device 520 is configured to automatically assume this angle: for example, elements of the devices may comprise a shape-memory alloy, such as Nitinol, which is configured to cause the device to assume this angle when in a resting, relaxed state, e.g., at 37 degrees Celsius (body temperature). As used in the present application, including in the claims and Inventive concepts, the "best-fit plane" defined by coaptation surface 534 is the plane that most closely matches the shape of the coaptation surface (even though the coaptation surface is typically curved), i.e., the plane that results in the minimal sum of squares of distances between the plane and the coaptation surface.

In an application of the present invention, a coaptation-assist device is provided that is a hybrid of coaptation-assist device 520, described hereinabove with reference to FIGS. 18A-F, and one of coaptation-assist devices 220A and 220B, described hereinabove with reference to FIGS. 8A and 8B, respectively. The loop-shaped ventricular anchors of the coaptation-assist device comprises a braided flat sheet comprising braided wires, as in coaptation-assist devices 220A and 220B, instead of anchor-loop wire loop 550. The coaptation-assist device may implement any of the features of coaptation-assist device 520, coaptation-assist device 220A, and/or coaptation-assist device 220B, mutatis mutandis.

Reference is now made to FIGS. 20A-B, which are schematic illustrations of a coaptation-assist device 620 for treating native valve 22, in accordance with an application of the present invention. Other than as described below, coaptation-assist device 620 is identical to coaptation-assist device 520, described hereinabove with reference to FIGS. 18A-F and 19, and like reference numerals refer to like parts. The features of coaptation-assist device 620 may also be implemented in any of the anchor-loop wire loops described herein, mutatis mutandis.

An anchor-loop wire loop 650 of a loop-shaped ventricular anchor 630 of coaptation-assist device 620 includes a distal-most portion 680 that is curved away from a best-fit plane 682 defined by lateral portions 684A and 684B of anchor-loop wire loop 650, when anchor-loop wire loop 650 is unconstrained (by application of any external forces, including by the anatomy or the delivery system), such that distal-most portion 680 is curved away from ventricular wall 27 when anchor-loop wire loop 650 is positioned in ventricle 23. Optionally, a distal-most tip 686 of distal-most portion 680 points partially proximally in a direction toward neo-leaflet 532. This curvature of distal-most portion 680 may help anchor-loop wire loop 650 accommodate different ventricular lengths.

Figure 21:
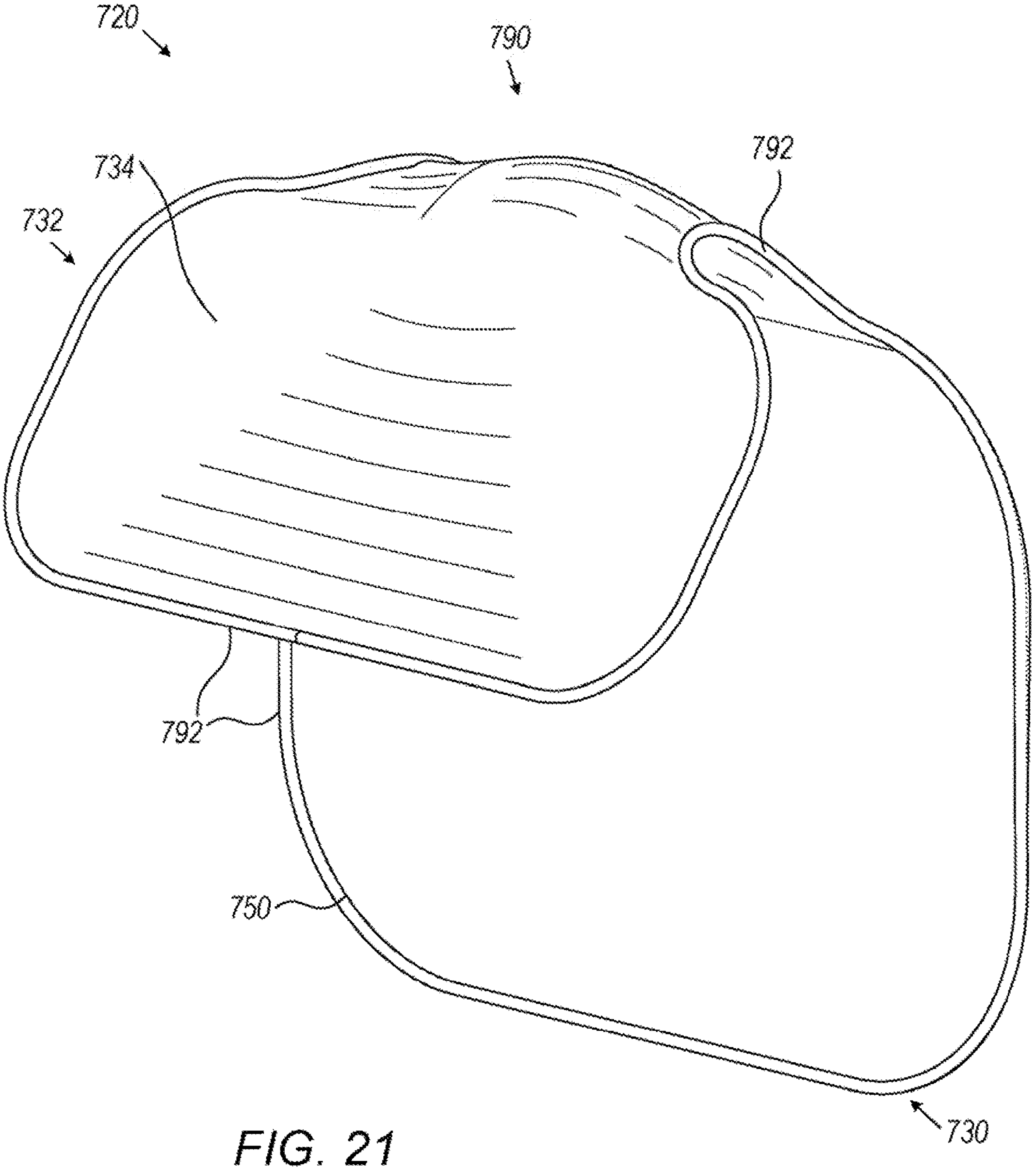
FIG. 21 is a schematic illustration of another coaptation-assist device, in accordance with an application of the present invention.

Reference is now made to FIG. 21, which is a schematic illustration of a coaptation-assist device 720 for treating native valve 22, in accordance with an application of the present invention. Coaptation-assist device 720 may implement any of the features of the other coaptation-assist devices described herein, mutatis mutandis.

Figure 22:
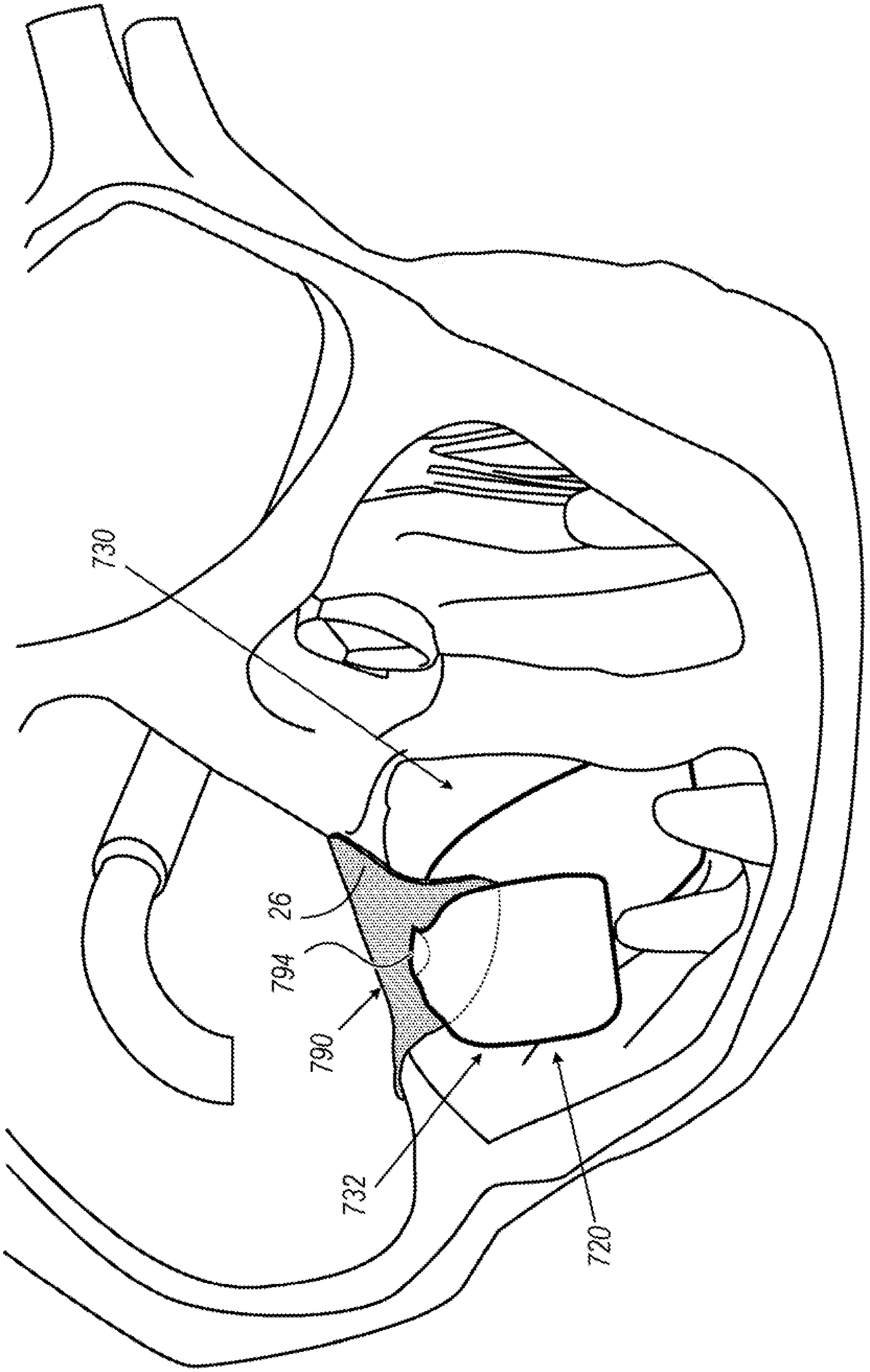
FIG. 22 is a schematic illustration of the coaptation-assist device of FIG. 21 implanted in a native valve, in accordance with an application of the present invention.

Reference is additionally made to FIG. 22, which is a schematic illustration of coaptation-assist device 720 implanted in native valve 22, in accordance with an application of the present invention. In the particular implantation shown in FIG. 22, native valve 22 is the tricuspid valve. FIG. 22 is a cross-sectional view of the heart, with an anterior portion of the heart, including the native anterior leaflet of the tricuspid valve, removed, such that only the septal and posterior leaflets are shown.

Coaptation-assist device 720 comprises a loop-shaped ventricular anchor 730, i.e., a ventricular anchor that has a loop-shaped border, and a neo-leaflet 732, which is supported by loop-shaped ventricular anchor 730. Loop-shaped ventricular anchor 730 is disposed distally to neo-leaflet 732.

Typically, loop-shaped ventricular anchor 730 comprises an anchor-loop wire loop 750 that defines at least a portion of the border of the loop-shaped ventricular anchor. Loop-shaped ventricular anchor 730 and anchor-loop wire loop 750 may implement any of the features of the loop-shaped ventricular anchors and anchor-loop wire loops, respectively, described herein, mutatis mutandis. Typically, loop-shaped ventricular anchor 730 is configured to be atraumatic so as not to penetrate (e.g., pierce) tissue of the surrounding anatomy. To this end, loop-shaped ventricular anchor 730 typically does not comprise any exposed sharp elements that might penetrate tissue.

Anchor-loop wire loop 750 is configured to be positioned in ventricle 23, extending between ventricular apical area 24 (at the bottom of ventricle 23) and subannular surface 25 of target native leaflet 26 of native valve 22. Anchor-loop wire loop 750 is configured to remain anchored in position against surrounding anatomy, including subannular surface 25, ventricular wall 27, and ventricular apical area 24, such as shown in FIG. 22. In other words, anchor-loop wire loop 750 is configured to be secured underneath and behind target native leaflet 26, in contact with subannular surface 25, to be seated apically, and to be stabilized by ventricular wall 27. Typically, anchor-loop wire loop 750 is configured to pass behind or across ventricular papillary muscles 46 of ventricular apical area 24. Optionally, the surrounding anatomy against which anchor-loop wire loop 750 is anchored further includes one or more of the following: a moderator band, one or more chordae tendineae, and one or more papillary muscles on the opposite side of ventricle 23.

Neo-leaflet 732 is configured to at least partially replace function of target native leaflet 26 by providing a surface of coaptation 734 for one or more opposing native leaflets 28 that oppose target native leaflet 26, when anchor-loop wire loop 750 is positioned in ventricle 23, such as shown in FIG. 22. Neo-leaflet 732 is typically configured to cover at least a portion of target native leaflet 26, and may implement any of the features of the neo-leaflets described herein, mutatis mutandis.

Coaptation-assist device 720 further comprises a native-leaflet-crossing portion 790, which is configured to be positioned passing through a puncture through target native leaflet 26 (even though loop-shaped ventricular anchor 730 itself is configured to be atraumatic, i.e., not to penetrate the surrounding ventricular anatomy, as described above). Neo-leaflet 732 is coupled to loop-shaped ventricular anchor 730 via native-leaflet-crossing portion 790. For some applications, coaptation-assist device 720 comprises a coaptation-assist-device wire loop 792 that is shaped so as to at least partially define neo-leaflet 732, loop-shaped ventricular anchor 730, and native-leaflet-crossing portion 790, such as shown.

For some applications, coaptation-assist device 720 can be extended and flattened into an elongate flattened configuration, similar to the flattened configuration of coaptation-assist device 20 shown in FIG. 1E. After being flattened, coaptation-assist device 720 can be crimped and then loaded into delivery tube 304, for delivery as described hereinabove with reference to FIGS. 9A-H, mutatis mutandis.

Unlike in the delivery method described hereinabove with reference to FIGS. 9A-H, during delivery of loop-shaped ventricular anchor 730, the delivery system (e.g., a needle thereof) is used to form a puncture 794 through target native leaflet 26, typically centrally and near the native annulus. Loop-shaped ventricular anchor 730 is passed through puncture 794 from the atrial to the ventricular side of the native leaflet (typically while still disposed in delivery tube 304), and deployed from the delivery tube and allowed to expand in the ventricle. Subsequently, neo-leaflet 732 is deployed from the delivery tube into the ventricle, on the atrial side of the native leaflet, such that the neo-leaflet covers at least a portion of an atrial surface of target native leaflet 26.

FIG. 23 is a schematic illustration of a coaptation-assist device implanted in a native mitral valve 22, in accordance with an application of the present invention.

Although the coaptation-assist devices described herein have been described as configured to treat a native atrioventricular valve, they may alternatively be configured to treat other native valves, such an aortic or pulmonary valve. For some such applications, the loop-shaped ventricular anchor is placed upside-down, with the anchor-loop wire loop placed in the outflow artery, i.e., in the aortic root and in the pulmonary artery, respectively, with the grasper grasping one of the cusps of the native valve.

The scope of the present invention includes embodiments described in the following applications, which are assigned to the assignee of the present application and are incorporated herein by reference. In an embodiment, techniques and apparatus described in one or more of the following applications are combined with techniques and apparatus described herein:

US Patent Application Publication 2016/0302917

US Patent Application Publication 2019/0350705

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A coaptation-assist device for treating a native atrioventricular valve of a subject, the coaptation-assist device comprising:

- a ventricular anchor, which is configured to be positioned in a ventricle, and which comprises:
  - a subannular anchor, which is configured to be anchored in position in a subannular space of a target native leaflet of the native atrioventricular valve; and
  - a ventricular wall anchor, which comprises one or more anchor-loop wire loops, which are configured to be anchored in position against a ventricular wall outside the subannular space; and
- a neo-leaflet, which is supported by the ventricular anchor and is configured to at least partially replace function of the target native leaflet by providing a surface of coaptation for one or more opposing native leaflets that oppose the target native leaflet, when the ventricular anchor is positioned in the ventricle.

2. The coaptation-assist device according to claim 1, wherein the one or more anchor-loop wire loops comprise exactly one anchor-loop wire loop.

3. The coaptation-assist device according to claim 2, wherein the anchor-loop wire loop, when unconstrained, includes a distal-most portion that is curved away from a best-fit plane defined by lateral portions of the anchor-loop wire loop.

4. The coaptation-assist device according to claim 2, wherein the anchor-loop wire loop includes a distal-most portion that is configured to curve away from the ventricular wall when the anchor-loop wire loop is positioned in ventricle.

5. The coaptation-assist device according to claim 1, wherein the one or more anchor-loop wire loops comprise a plurality of linked anchor-loop wire loops.

6. The coaptation-assist device according to claim 1, wherein the one or more anchor-loop wire loops are shaped so as to define a plurality of loop-lobes.

7. The coaptation-assist device according to claim 6, wherein the plurality of loop-lobes comprises three loop-lobes.

8. The coaptation-assist device according to claim 1, wherein the ventricular anchor is configured to remain anchored in position by force applied by the one or more anchor-loop wire loops to surrounding anatomy.

9. The coaptation-assist device according to claim 8, wherein the ventricular anchor is configured to remain anchored in position by radially-outwardly-directed force applied by the one or more anchor-loop wire loops to the surrounding anatomy.

10. The coaptation-assist device according to claim 1, wherein the ventricular anchor is configured to be atraumatic so as not to penetrate tissue of surrounding anatomy.

11. The coaptation-assist device according to claim 1, wherein the coaptation-assist device does not comprise any elements that are configured to penetrate tissue.

12. The coaptation-assist device according to claim 1, wherein the one or more anchor-loop wire loops are configured to be anchored in position against the ventricular wall outside the subannular space, including a ventricular apical area, when the one or more anchor-loop wire loops are positioned in the ventricle.

13. The coaptation-assist device according to claim 1, wherein the one or more anchor-loop wire loops are configured to be anchored in position against the ventricular wall outside the subannular space, and one or more ventricular papillary muscles of a ventricular apical area, when the one or more anchor-loop wire loops are positioned in the ventricle.

14. The coaptation-assist device according to claim 1, wherein the neo-leaflet is configured such that the coaptation surface is generally static throughout a cardiac cycle of the subject upon implantation of the coaptation-assist device in a heart of the subject.

15. The coaptation-assist device according to claim 1, wherein the neo-leaflet is configured such that the coaptation surface moves toward and away from the one or more opposing native leaflets during a cardiac cycle of the subject upon implantation of the coaptation-assist device in a heart of the subject.

16. The coaptation-assist device according to claim 1, further comprising a native-leaflet grasper, which is configured to grasp atrial and ventricular surfaces of the target native leaflet, in order to support the neo-leaflet, and to orient the neo-leaflet with respect to the native atrioventricular valve.

17. The coaptation-assist device according to claim 16, comprising a wire that is shaped so as to at least partially define the ventricular anchor and the native-leaflet grasper.

18. The coaptation-assist device according to claim 16, wherein the native-leaflet grasper is shaped so as to define first and second portions that are configured to grasp the atrial and the ventricular surfaces of the target native leaflet by sandwiching at least a portion of the atrial and the ventricular surfaces of the target native leaflet between the first and the second portions of the native-leaflet grasper.

19. The coaptation-assist device according to claim 18, wherein the first and the second portions are configured to fold toward each other so as to grasp the atrial and the ventricular surfaces of the target native leaflet by sandwiching the at least a portion of the atrial and the ventricular surfaces of the target native leaflet between the first and the second portions of the native-leaflet grasper.

20. The coaptation-assist device according to claim 19, wherein the native-leaflet grasper is shaped so as to further define a third portion at a fold between the first and the second portions of the native-leaflet grasper, and wherein the third portion of the native-leaflet grasper is configured to extend around the free edge of the target native leaflet when the first and the second portions of the native-leaflet grasper sandwich the at least a portion of the atrial and the ventricular surfaces of the target native leaflet.

21. The coaptation-assist device according to claim 16, wherein the native-leaflet grasper comprises one or more supra-annular supports, which are configured to press against an atrial surface of the target native leaflet when the one or more anchor-loop wire loops are positioned in the ventricle.

22. The coaptation-assist device according to claim 1, wherein the native atrioventricular valve is a tricuspid valve, and wherein the neo-leaflet is configured to at least partially replace function of the target native leaflet by providing a surface of coaptation for the one or more opposing native leaflets of the tricuspid valve, when the one or more anchor-loop wire loops are positioned in the ventricle.

23. The coaptation-assist device according to claim 1, wherein the native atrioventricular valve is a mitral valve, and wherein the neo-leaflet is configured to at least partially replace function of the target native leaflet by providing a surface of coaptation for the opposing native leaflet of the mitral valve, when the one or more anchor-loop wire loops are positioned in the ventricle.

24. The coaptation-assist device according to claim 1, wherein the coaptation-assist device is configured such that the coaptation surface of the neo-leaflet crosses from an atrial side to a ventricular side of a native valvular plane, when the one or more anchor-loop wire loops are positioned in the ventricle.

25. The coaptation-assist device according to claim 1, wherein the ventricular wall anchor further comprises an anchor-loop cover attached to the one or more anchor-loop wire loops.

26. The coaptation-assist device according to claim 25, wherein the anchor-loop cover comprises one or more thin sheets of material that extend across a space at least partially surrounded by the one or more anchor-loop wire loops.

27. The coaptation-assist device according to claim 25, wherein the anchor-loop cover comprises a coating on the one or more anchor-loop wire loops.

28. The coaptation-assist device according to claim 1, wherein the neo-leaflet comprises:

a neo-leaflet wire loop that defines at least a portion of a border of the neo-leaflet; and a neo-leaflet cover, which is attached to the neo-leaflet wire loop and provides the surface of coaptation.

29. The coaptation-assist device according to claim 28, wherein the coaptation-assist device is configured such that when unconstrained, an angle is defined between (a) an anchor-loop best-fit plane defined by the one or more anchor-loop wire loops and (b) a neo-leaflet best-fit plane defined by the neo-leaflet wire loop, the angle between 60 and 100 degrees.

30. The coaptation-assist device according to claim 1, further comprising a pouch, which is configured to inflate by blood flow during a cardiac cycle of a heart of the subject, so as to push the coaptation-assist device against one or more of: a ventricular surface of the target native leaflet and an annulus of the native atrioventricular valve, thereby stabilizing the coaptation-assist device with respect to the native atrioventricular valve.

31. The coaptation-assist device according to claim 30, wherein the coaptation-assist device further comprises a native-leaflet grasper, which is configured to grasp atrial and ventricular surfaces of the target native leaflet, in order to support the neo-leaflet, and to orient the neo-leaflet with respect to the native atrioventricular valve, and wherein the pouch is defined by the native-leaflet grasper.

32. The coaptation-assist device according to claim 1, wherein the neo-leaflet is configured such that, upon implantation of the coaptation-assist device in a heart of the subject, the coaptation surface is generally static throughout a cardiac cycle of the subject and the coaptation is provided by motion of the one or more opposing native leaflets against the generally static coaptation surface provided by the neo-leaflet.

33. The coaptation-assist device according to claim 32, further comprising a native-leaflet grasper, which is configured to grasp atrial and ventricular surfaces of the target native leaflet, in order to support the neo-leaflet, and to orient the neo-leaflet with respect to the native atrioventricular valve.

34. A method for treating a native atrioventricular valve of a subject, the method comprising:

positioning a ventricular anchor of a coaptation-assist device in a ventricle, such that (a) a subannular anchor of the ventricular anchor is anchored in position in a subannular space of a target native leaflet of the native atrioventricular valve, and (b) one or more anchor-loop wire loops of a ventricular wall anchor of the ventricular anchor are anchored in position against a ventricular wall outside the subannular space; and positioning a neo-leaflet of the coaptation-assist device such that the neo-leaflet is supported by the ventricular anchor and at least partially replaces function of the target native leaflet by providing a surface of coaptation for one or more opposing native leaflets that oppose the target native leaflet.

35. The method according to claim 34, wherein positioning the neo-leaflet comprises positioning the neo-leaflet such that, upon implantation of the coaptation-assist device in a heart of the subject, the coaptation surface is generally static throughout a cardiac cycle of the subject and the coaptation is provided by motion of the one or more opposing native leaflets against the generally static coaptation surface provided by the neo-leaflet.

36. The method according to claim 35, further comprising positioning a native-leaflet grasper of the coaptation-assist device to grasp atrial and ventricular surfaces of the target native leaflet, in order to support the neo-leaflet, and to orient the neo-leaflet with respect to the native atrioventricular valve.

37. The method according to claim 34, further comprising positioning a native-leaflet grasper of the coaptation-assist device to grasp atrial and ventricular surfaces of the target native leaflet, in order to support the neo-leaflet, and to orient the neo-leaflet with respect to the native atrioventricular valve.

* * * * *